United States Patent
Kaneoya et al.

(10) Patent No.: US 10,544,365 B2
(45) Date of Patent: *Jan. 28, 2020

(54) NEMATIC LIQUID CRYSTAL COMPOSITION

(71) Applicant: DIC Corporation, Tokyo (JP)

(72) Inventors: Masakazu Kaneoya, Kita-adachi-gun (JP); Kiyofumi Takeuchi, Kita-adachi-gun (JP); Masashi Osawa, Kita-adachi-gun (JP); Kenta Tojo, Kita-adachi-gun (JP); Tetsuo Kusumoto, Kita-adachi-gun (JP)

(73) Assignee: DIC CORPORATION, Tokyo (JP)

( * ) Notice: Subject to any disclaimer, the term of this patent is extended or adjusted under 35 U.S.C. 154(b) by 170 days.

This patent is subject to a terminal disclaimer.

(21) Appl. No.: 14/912,262

(22) PCT Filed: Aug. 21, 2014

(86) PCT No.: PCT/JP2014/071903
§ 371 (c)(1),
(2) Date: Feb. 16, 2016

(87) PCT Pub. No.: WO2015/029876
PCT Pub. Date: Mar. 5, 2015

(65) Prior Publication Data
US 2016/0186059 A1 Jun. 30, 2016

(30) Foreign Application Priority Data
Aug. 30, 2013 (JP) .................................. 2013-179541

(51) Int. Cl.
G02F 1/1333 (2006.01)
C09K 19/34 (2006.01)
C09K 19/30 (2006.01)
C09K 19/32 (2006.01)
C07C 43/247 (2006.01)
C07D 309/04 (2006.01)
C07D 319/06 (2006.01)
C09K 19/02 (2006.01)
C09K 19/54 (2006.01)
C09K 19/56 (2006.01)
G02F 1/1337 (2006.01)
C09K 19/12 (2006.01)
C09K 19/04 (2006.01)
G02F 1/00 (2006.01)

(52) U.S. Cl.
CPC ........ *C09K 19/3402* (2013.01); *C07C 43/247* (2013.01); *C07D 309/04* (2013.01); *C07D 319/06* (2013.01); *C09K 19/0208* (2013.01); *C09K 19/3066* (2013.01); *C09K 19/322* (2013.01); *C09K 19/542* (2013.01); *C09K 19/56* (2013.01); *G02F 1/133711* (2013.01); *G02F 1/133788* (2013.01); *C07C 2601/14* (2017.05); *C09K 2019/0466* (2013.01); *C09K 2019/124* (2013.01); *C09K 2019/3025* (2013.01); *C09K 2019/3422* (2013.01); *C09K 2019/548* (2013.01); *G02F 1/0045* (2013.01)

(58) Field of Classification Search
CPC ............ C09K 19/3402; C09K 19/0208; C09K 19/3066; C09K 19/322; C09K 19/542; C09K 19/56; C09K 2019/3422; C09K 2019/548; G02F 1/1333; G02F 1/133711; G02F 1/133788; C07C 43/247; C07D 309/04; C07D 319/06
USPC ...................................................... 252/299.6
See application file for complete search history.

(56) References Cited

U.S. PATENT DOCUMENTS

| | | | |
|---|---|---|---|
| 4,818,431 A | 4/1989 | Eidenschink et al. | |
| 5,032,313 A | 7/1991 | Goto et al. | |
| 5,324,449 A | 6/1994 | Kurmeier et al. | |
| 5,399,292 A | 3/1995 | Buchecker et al. | |
| 5,487,845 A | 1/1996 | Reiffenrath et al. | |

(Continued)

FOREIGN PATENT DOCUMENTS

| | | |
|---|---|---|
| CN | 1184462 A | 6/1998 |
| CN | 102186821 A | 9/2011 |

(Continued)

OTHER PUBLICATIONS

International Search Report dated Nov. 18, 2014, issued in counterpart Application No. PCT/JP2014/071903 (2 pages).

(Continued)

Primary Examiner — Geraldina Visconti
(74) Attorney, Agent, or Firm — Westerman, Hattori, Daniels & Adrian, LLP

(57) ABSTRACT

A liquid crystal composition that has a positive dielectric anisotropy and a sufficiently low viscosity and that causes no display defects when used in liquid crystal display devices is provided without decreasing or increasing the refractive index anisotropy or nematic phase-isotropic liquid phase transition temperature. This liquid crystal composition contains at least one compound selected from compounds represented by general formula (LC0) and at least one compound selected from the group consisting of compounds represented by general formulas (LC1) to (LC5). This liquid crystal composition can be used to provide a reliable liquid crystal display device capable of maintaining a high voltage-holding ratio at high temperatures. This liquid crystal display device is highly practical as a liquid crystal display and is effective in achieving quick response without significantly decreasing the cell gap.

29 Claims, No Drawings

(56) References Cited

U.S. PATENT DOCUMENTS

| | | |
|---|---|---|
| 5,730,904 A | 3/1998 | Bartmann et al. |
| 5,733,477 A | 3/1998 | Kondo et al. |
| 5,800,734 A | 9/1998 | Buchecker et al. |
| 5,858,270 A | 1/1999 | Matsui et al. |
| 5,976,407 A | 11/1999 | Tarumi et al. |
| 6,051,288 A | 4/2000 | Kondo et al. |
| 6,200,654 B1 | 3/2001 | Poetsch et al. |
| 6,207,076 B1 | 3/2001 | Koga et al. |
| 6,210,603 B1 | 4/2001 | Kondo et al. |
| 6,254,941 B1 | 7/2001 | Kondou et al. |
| 6,468,607 B1 | 10/2002 | Takehara et al. |
| 6,579,577 B2 | 6/2003 | Kondo et al. |
| 7,001,646 B2 | 2/2006 | Heckmeier et al. |
| 7,175,891 B2 | 2/2007 | Heckmeier et al. |
| 7,198,827 B1 | 4/2007 | Takeuchi et al. |
| 7,250,198 B2 | 7/2007 | Heckmeier et al. |
| 7,361,388 B2 | 4/2008 | Kirsch et al. |
| 7,604,851 B2 | 10/2009 | Heckmeier et al. |
| 7,674,507 B2 | 3/2010 | Lietzau et al. |
| 7,704,566 B2 | 4/2010 | Heckmeier et al. |
| 7,767,277 B2 | 8/2010 | Lietzau et al. |
| 8,168,083 B2 | 5/2012 | Goebel et al. |
| 8,916,718 B2 | 12/2014 | Tojo et al. |
| 9,039,929 B2 * | 5/2015 | Kaneoya ............ C09K 19/20 252/299.01 |
| 9,079,836 B2 | 7/2015 | Tojo et al. |
| 9,181,484 B2 | 11/2015 | Tojo et al. |
| 9,315,727 B2 | 4/2016 | Tojo et al. |
| 9,321,961 B2 * | 4/2016 | Kaneoya ............ C09K 19/3059 |
| 9,573,923 B2 | 2/2017 | Tojo et al. |
| 9,587,175 B2 * | 3/2017 | Kaneoya ............ C09K 19/20 |
| 9,605,208 B2 * | 3/2017 | Kaneoya ............ C09K 19/20 |
| 9,637,466 B2 | 5/2017 | Tojo et al. |
| 10,000,700 B2 * | 6/2018 | Taniguchi ............ C09K 19/20 |
| 2002/0166994 A1 | 11/2002 | Kondo et al. |
| 2003/0197153 A1 | 10/2003 | Heckmeier et al. |
| 2003/0236304 A1 | 12/2003 | Jolidon et al. |
| 2005/0012073 A1 | 1/2005 | Goulding et al. |
| 2005/0017216 A1 | 1/2005 | Poetsch et al. |
| 2005/0092966 A1 | 5/2005 | Heckmeier et al. |
| 2006/0061699 A1 | 3/2006 | Kirsch et al. |
| 2006/0263542 A1 | 11/2006 | Kirsch et al. |
| 2006/0286308 A1 | 12/2006 | Kirsch et al. |
| 2007/0051919 A1 | 3/2007 | Kondou et al. |
| 2007/0134444 A1 | 6/2007 | Harding et al. |
| 2007/0205396 A1 | 9/2007 | Czanta et al. |
| 2008/0132716 A1 | 6/2008 | Lietzau et al. |
| 2009/0065739 A1 | 3/2009 | Haseba et al. |
| 2009/0103011 A1 | 4/2009 | Bernatz et al. |
| 2009/0230355 A1 | 9/2009 | Czanta et al. |
| 2009/0302273 A1 | 12/2009 | Tanaka |
| 2010/0127211 A1 | 5/2010 | Tanaka |
| 2010/0294991 A1 | 11/2010 | Saito et al. |
| 2010/0308267 A1 | 12/2010 | Wittek et al. |
| 2010/0328600 A1 | 12/2010 | Shimada et al. |
| 2011/0001090 A1 | 1/2011 | Wittek et al. |
| 2011/0024682 A1 | 2/2011 | Czanta et al. |
| 2011/0037024 A1 | 2/2011 | Kobayashi |
| 2011/0037912 A1 | 2/2011 | Saito et al. |
| 2011/0193022 A1 | 8/2011 | Tanaka et al. |
| 2011/0233466 A1 | 9/2011 | Jansen et al. |
| 2011/0253934 A1 | 10/2011 | Lietzau et al. |
| 2011/0291048 A1 | 12/2011 | Hamano et al. |
| 2011/0315924 A1 | 12/2011 | Kojima et al. |
| 2011/0315925 A1 | 12/2011 | Hiraoka et al. |
| 2013/0300996 A1 | 11/2013 | Takeuchi et al. |
| 2013/0306908 A1 | 11/2013 | Jansen et al. |
| 2014/0225036 A1 | 8/2014 | Kaneoya et al. |
| 2014/0275577 A1 | 9/2014 | Tojo et al. |
| 2015/0087847 A1 | 3/2015 | Tojo et al. |
| 2015/0124205 A1 | 5/2015 | Kaneoya et al. |
| 2015/0159086 A1 * | 6/2015 | Kaneoya ............ C09K 19/3059 252/299.62 |
| 2015/0184076 A1 | 7/2015 | Kaneoya et al. |
| 2015/0203757 A1 | 7/2015 | Kaneoya et al. |
| 2015/0218451 A1 | 8/2015 | Kaneoya et al. |
| 2015/0284634 A1 * | 10/2015 | Kaneoya ............ C09K 19/3059 252/299.61 |
| 2015/0322343 A1 * | 11/2015 | Kaneoya ............ C09K 19/322 252/299.62 |
| 2016/0186059 A1 * | 6/2016 | Kaneoya ............ C09K 19/3066 349/124 |

FOREIGN PATENT DOCUMENTS

| | | |
|---|---|---|
| DE | 41 32 006 A1 | 4/1993 |
| DE | 4416256 A1 | 11/1994 |
| DE | 10 2009 009 631 A1 | 9/2009 |
| DE | 102010015824 A1 | 3/2011 |
| DE | 112013004132 B4 | 11/2016 |
| EP | 0 156 554 A2 | 10/1985 |
| EP | 0 882 696 A1 | 12/1998 |
| JP | 2-501311 | 5/1990 |
| JP | 02/233626 A | 9/1990 |
| JP | 2-289529 A | 11/1990 |
| JP | 3-122199 A | 5/1991 |
| JP | 4-501575 A | 3/1992 |
| JP | H05-263461 A | 10/1993 |
| JP | 6-504032 | 5/1994 |
| JP | 6-239776 A | 8/1994 |
| JP | H8-283183 A | 10/1996 |
| JP | 9-157202 A | 6/1997 |
| JP | 10-67988 A | 3/1998 |
| JP | 10-101599 A | 4/1998 |
| JP | 10-130181 A | 5/1998 |
| JP | H10130187 A | 5/1998 |
| JP | 10-204016 A | 8/1998 |
| JP | 11-29771 A | 2/1999 |
| JP | 2000169413 A | 6/2000 |
| JP | 2000-355560 A | 12/2000 |
| JP | 2001-011458 A | 1/2001 |
| JP | 2001-019649 A | 1/2001 |
| JP | 2001-026560 A | 1/2001 |
| JP | 3122199 B2 | 1/2001 |
| JP | 2003-176251 A | 6/2003 |
| JP | 2003-183656 A | 7/2003 |
| JP | 2003286217 A | 10/2003 |
| JP | 2003-533557 A | 11/2003 |
| JP | 2004-529214 A | 9/2004 |
| JP | 2004-352721 A | 12/2004 |
| JP | 2004-355560 A | 12/2004 |
| JP | 2005-517079 A | 6/2005 |
| JP | 2005-220355 A | 8/2005 |
| JP | 2005-232455 A | 9/2005 |
| JP | 2005/529176 A | 9/2005 |
| JP | 2005232214 A | 9/2005 |
| JP | 2005232215 A | 9/2005 |
| JP | 2005250223 A | 9/2005 |
| JP | 2006-515283 A | 5/2006 |
| JP | 2006257274 A | 9/2006 |
| JP | 2006-328400 A | 12/2006 |
| JP | 2007-501301 A | 1/2007 |
| JP | 2007-23071 A | 2/2007 |
| JP | 2007-503485 A | 2/2007 |
| JP | 2007503405 A | 2/2007 |
| JP | 2007503487 A | 2/2007 |
| JP | 2007-51291 A | 3/2007 |
| JP | 2007-070295 A | 3/2007 |
| JP | 2007-177241 A | 7/2007 |
| JP | 2007-277127 A | 10/2007 |
| JP | 2008-69153 A | 3/2008 |
| JP | 2008-222588 A | 9/2008 |
| JP | 2008-545669 A | 12/2008 |
| JP | 2009-067780 A | 4/2009 |
| JP | 2009-84560 A | 4/2009 |
| JP | 2009-179813 A | 8/2009 |
| JP | 2009-185285 A | 8/2009 |
| JP | 2009-215556 A | 9/2009 |
| JP | 2009-292730 A | 12/2009 |
| JP | 2010-500980 A | 1/2010 |
| JP | 2010-275390 A | 12/2010 |
| JP | 2011-037998 A | 2/2011 |
| JP | 2011-136998 A | 7/2011 |
| JP | 2011-148761 A | 8/2011 |

(56) References Cited

FOREIGN PATENT DOCUMENTS

| | | |
|---|---|---|
| JP | 2011-168530 A | 9/2011 |
| JP | 2011-195587 A | 10/2011 |
| JP | 2012-117062 A | 6/2012 |
| JP | 2013-170246 A | 9/2013 |
| JP | 5-382268 B1 | 1/2014 |
| JP | 5435318 B1 | 3/2014 |
| JP | 2014-105178 A | 6/2014 |
| KR | 20060119879 A | 11/2006 |
| WO | 96/11897 A1 | 4/1996 |
| WO | 96/032365 A1 | 10/1996 |
| WO | 96/32365 A1 | 10/1996 |
| WO | 97/37960 A1 | 10/1997 |
| WO | 98/23564 A1 | 6/1998 |
| WO | 03066774 A1 | 8/2003 |
| WO | 2005/019377 A1 | 3/2005 |
| WO | 2008/105286 A1 | 9/2008 |
| WO | 2009/034867 A1 | 3/2009 |
| WO | 2009/125668 A1 | 10/2009 |
| WO | 2009/150963 A1 | 12/2009 |
| WO | 2010/047260 A1 | 4/2010 |
| WO | 2012/043387 A1 | 4/2012 |
| WO | 2012/100809 A1 | 8/2012 |
| WO | 2012/161178 A1 | 11/2012 |
| WO | 2013/018796 A1 | 2/2013 |
| WO | 2013/099754 A1 | 7/2013 |
| WO | 2013/141116 A1 | 9/2013 |
| WO | 2013/172162 A1 | 11/2013 |
| WO | 14/030481 A1 | 2/2014 |
| WO | 2015/029876 A1 | 3/2015 |

OTHER PUBLICATIONS

International Search Report dated Sep. 29, 2015, issued in counterpart International Application No. PCT/JP2015/071323.

Decision to Grant a Patent dated Feb. 26, 2016, issued in counterpart Japanese Patent Application No. 2015-560121, w/English translation.

Non Final Office Action dated Oct. 19, 2017, issued in U.S. Appl. No. 15/320,974.

International Search Report dated Nov. 26, 2013, issued in Application No. PCT/JP2013/073127, counterpart of U.S. Appl. No. 14/425,267/ now U.S. Pat. No. 9,321,961.

International Search Report dated Sep. 17, 2013, issued in Application No. PCT/JP2013/070058, counterpart of U.S. Appl. No. 14/421,015/ now U.S. Pat. No. 9,587,175.

International Search Report dated Sep. 18, 2015, issued in Application No. PCT/JP2012/069461, counterpart of U.S. Appl. No. 14/236,547/ now U.S. Pat. No. 9,039,929.

International Search Report dated Oct. 23, 2013, issued in Application No. PCT/JP2013/073967, counterpart of U.S. Appl. No. 14/436,181.

International Search Report dated Oct. 22, 2013, issued in Application No. PCT/JP2013/073968, counterpart of U.S. Appl. No. 14/436,213.

Notice of Allowance dated Dec. 10, 2018, issued in U.S. Appl. No. 15/328,120 (10 pages).

Notice of Allowance dated Jan. 23, 2019, issued in U.S. Appl. No. 15/328,120 (16 pages).

Resistry(stn) [Online], Oct. 3, 2011 (Oct. 3, 2011), (retrieval date: Mar. 11, 2013 (Mar. 11, 2013)) CAS resistration No. 1334226-61-7 (1 page).

Decision to Grant a Patent dated Apr. 2, 2015, issued in JP2014-556873 (3 pages).

Decision to Grant a Patent dated Apr. 2, 2015, issued in JP2014-556869, with English translation (5 pages).

English translation of International Search Report dated Oct. 7, 2014, issued in PCT/JP2014/068784 (3 pages).

International Search Report dated Oct. 7, 2014, issued in PCT/JP2014/072633, with English translation (4 pages).

English translation of Written Opinion dated Oct. 7, 2014, issued in PCT/JP2014/068784 (4 pages).

Written Opinion dated Oct. 7, 2014, issued in PCT/JP2014/072633 (5 pages).

Notice of Reason for Refusal dated Jan. 29, 2015, issued in JP2014-556873 (7 pages).

Notice of Reason for Refusal dated Jan. 29, 2015, issued in JP2014-556869 (6 pages).

Miroslav Kuchar et al., "Use of Qsar in Design of Antiinflammatory Fluorinated Arylalkanoic Acids", Collection of Czechoslovak Chemical Communications, 1990, vol. 55, No. 1, pp. 296-306.

Non-Final Office Action dated Aug. 12, 2016, issued in U.S. Appl. No. 14/904,226 (18 pages).

Notice of Allowance dated Jan. 17, 2017, issued in U.S. Appl. No. 14/904,226 (14 pages).

Non-Final Office Action dated Jul. 6, 2016, issued in U.S. Appl. No. 14/907,034 (8 pages).

Notice of Allowance dated Oct. 12, 2016, issued in U.S. Appl. No. 14/907,034 (7 pages).

\* cited by examiner

NEMATIC LIQUID CRYSTAL COMPOSITION

TECHNICAL FIELD

The present invention relates to nematic liquid crystal compositions that exhibit a positive dielectric anisotropy ($\Delta\varepsilon$) and that are useful as electro-optical liquid crystal display materials.

BACKGROUND ART

Liquid crystal display devices are used in applications such as watches, calculators, measuring instruments, automotive instrument panels, word processors, electronic organizers, printers, computers, televisions, clocks, and advertisement boards. Typical liquid crystal display modes include twisted nematic (TN), super-twisted nematic (STN), and other modes based on thin-film transistors (TFTs), such as VA, which is characterized by vertical alignment, and in-plane switching (IPS)/FFS, which is characterized by horizontal alignment. Liquid crystal compositions used in liquid crystal display devices are required to be stable to external factors such as moisture, air, heat, and light, to exhibit a liquid crystal phase over a wider temperature range centered on room temperature, and to have low viscosity and low driving voltage. In addition, liquid crystal compositions are composed of several to tens of compounds to optimize properties such as dielectric anisotropy ($\Delta\varepsilon$) and refractive index anisotropy ($\Delta n$) depending on the specific display device.

Whereas liquid crystal compositions of negative $\Delta\varepsilon$ are used in vertical-alignment displays, liquid crystal compositions of positive $\Delta\varepsilon$ are used in horizontal-alignment displays such as TN, STN, and IPS displays. Recently, a driving mode has been reported in which a liquid crystal composition of positive $\Delta\varepsilon$ is vertically aligned when no voltage is applied and is driven by applying an IPS/FFS electric field, boosting the need for liquid crystal compositions of positive $\Delta\varepsilon$. Liquid crystal compositions are also required to have low driving voltage, high response speed, and a wide operating temperature range in all driving modes. Specifically, liquid crystal compositions are required to have a positive $\Delta\varepsilon$ large in absolute value, a low viscosity ($\eta$), and a high nematic phase-isotropic liquid phase transition temperature ($T_{ni}$). The $\Delta n$ of liquid crystal compositions also needs to be adjusted to an appropriate range depending on the cell gap by taking into account the product of $\Delta n$ and the cell gap (d), i.e., $\Delta n \times d$. Liquid crystal compositions used in applications such as televisions are also required to have a low $\gamma_1$ since quick response is of a higher priority in these applications.

There are disclosed liquid crystal compositions containing compounds represented by formulas (A-1) and (A-2), which are liquid crystal compounds of positive $\Delta\varepsilon$ (PTLs 1 to 4). These liquid crystal compositions, however, fail to provide sufficiently low viscosity. Also disclosed are compounds represented by general formulas (A-3) and (A-4), which have a —CF$_2$O— or —OCF$_2$— linking group, and liquid crystal compositions containing such compounds (PTLs 5 to 21). Again, these liquid crystal compositions fail to provide sufficiently low viscosity.

[Chem. 1]

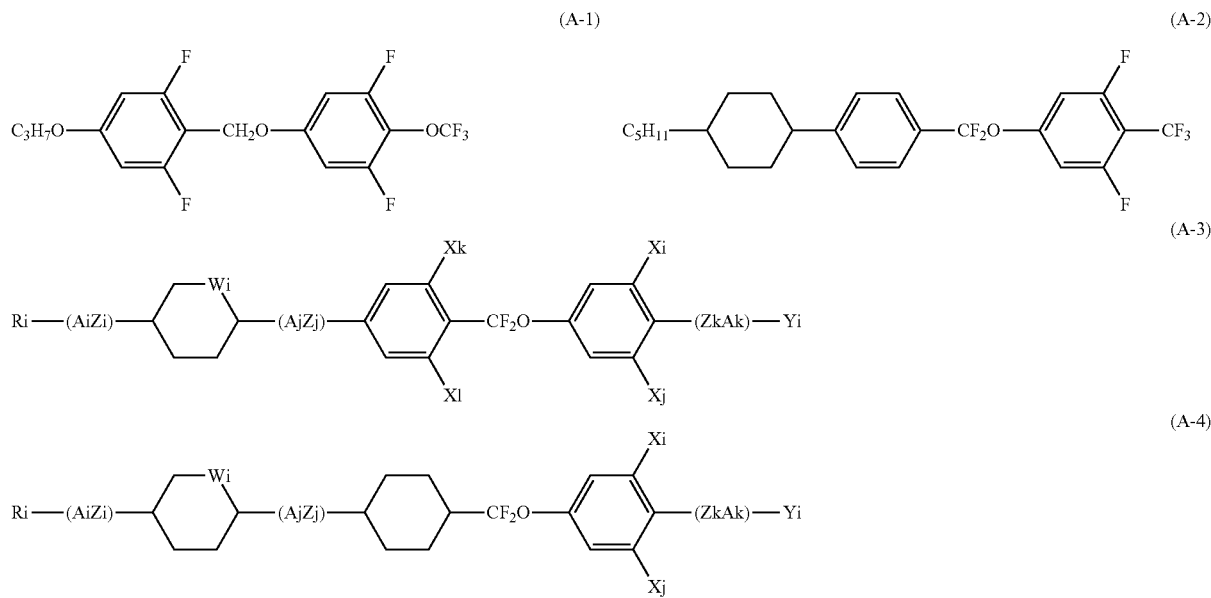

CITATION LIST

Patent Literature

PTL 1: WO96/032365
PTL 2: Japanese Unexamined Patent Application Publication No. 09-157202
PTL 3: WO98/023564
PTL 4: Japanese Unexamined Patent Application Publication No. 2003-183656
PTL 5: Japanese Unexamined Patent Application Publication N Y. 2-789529
PTL 6: Japanese Patent No. 3122199
PTL 7: WO96/011897
PTL 8: WO97/037960

PTL 9: Japanese Unexamined Patent Application Publication No 10-204016
PTL 10: Japanese Unexamined Patent Application Publication No. 2008-69153
PTL 11: US-4818431
PTL 12: DE4132006
PTL 13: U.S. Pat. No. 7,361,388
PTL 14: U.S. Pat. No. 7,674,507
PTL 15: U.S. Pat. No. 7,767,277
PTL 16: Japanese Unexamined Patent Application Publication (Translation of PCT Application) No. 2006-515283
PTL 17: Japanese Unexamined Patent Application Publication (Translation of PCT Application) No. 2008-545669
PTL 18: Japanese Unexamined Patent Application Publication (Translation of PCT Application) No. 2010-500980
PTL 19: EP-156554
PTL 20: Japanese Unexamined Patent Application Publication No. 2011-136998
PTL 21: U.S. Pat. No. 7,361,388
PTL 22: Japanese Unexamined Patent Application Publication No. 10-67988
PTL 23: Japanese Unexamined Patent Application Publication No. 11-29771.
PTL 24: Japanese Unexamined Patent Application Publication No. 2003-176251
PTL 25: Japanese Unexamined Patent Application Publication (Translation of PCT Application) No. 2003-533557
PTL 26: Japanese Unexamined Patent Application Publication (Translation of PCT Application) No. 2004-529214
PTL 27: Japanese Unexamined Patent Application Publication No. 2005-220355
PTL 28: Japanese Unexamined Patent Application Publication No. 2005-232455
PTL 29: Japanese Unexamined Patent Application Publication No. 2006-328400
PTL 30: Japanese Unexamined Patent Application Publication No. 2007-51291
PTL 31: Japanese Unexamined Patent Application Publication (Translation of PCT Application) No. 2007-501301
PTL 32: Japanese Unexamined Patent Application Publication (Translation of PCT Application) No. 2007-503485
PTL 33: Japanese Unexamined. Patent Application Publication No. 2009-84560
PTL 34: Japanese Unexamined Patent Application Publication No. 2009-179813
PTL 35: Japanese Unexamined Patent Application Publication No. 2009-185285
PTL 36: Japanese Unexamined Patent Application Publication No. 2010-275390
PTL 37: Japanese Unexamined Patent Application Publication No. 2012-117062
PTL 38: U.S. Pat. No. 5,976,407
PTL 39: U.S. Pat. No. 7,001,646
PTL 40: U.S. Pat. No. 7,175,891
PTL 41: TS-7250198
PTL 42: U.S. Pat. No. 7,604,851
PTL 43: U.S. Pat. No. 7,704,566
PTL 44: U.S. Pat. No. 8,168,083
PTL 45: US-2010/0308267
PTL 46: US-2011/0024682
PTL 47: US-2011/0315924.

SUMMARY OF INVENTION

Technical Problem

An object of the present invention is to provide a liquid crystal composition having a positive dielectric anisotropy ($\Delta\varepsilon$) and a sufficiently low viscosity (q) while adjusting the refractive index anisotropy ($\Delta n$) to the desired level and maintaining an appropriate nematic phase temperature range without decreasing the nematic phase-isotropic liquid phase transition temperature ($T_{ni}$) or increasing the lower temperature limit of the nematic phase.

Solution to Problem

The inventors have researched various fluorobenzenes and have discovered that the foregoing object can be achieved by the use of a particular combination of compounds, which has led to the present invention.

The present invention provides a liquid crystal composition having a positive dielectric anisotropy and a liquid crystal display device including the liquid crystal composition. This liquid crystal composition contains at least one compound represented by general formula (LC0).

[Chem. 2]

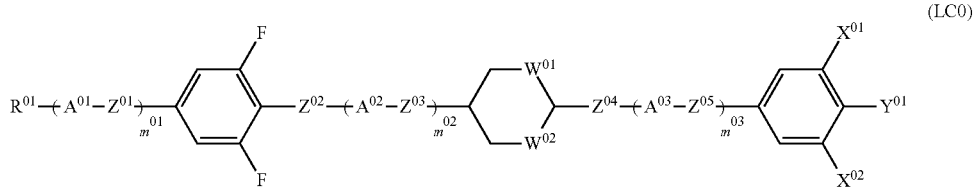

(LC0)

In the formula, $R^{01}$ is an alkyl group of 1 to 15 carbon atoms, where at least one —$CH_2$— of the alkyl group is optionally replaced by —O—, —CH=CH—, —CO—, —OCO—, —COO—, —C≡C—, —$CF_2$O— or —O$CF_2$— such that no oxygen atoms are directly adjacent to each other, and at least one hydrogen atom of the alkyl group is optionally replaced by halogen.

$A^{01}$ to $A^{03}$ are each independently any of the following structures.

[Chem. 3]

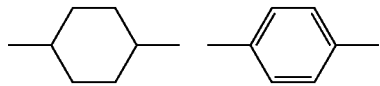

-continued

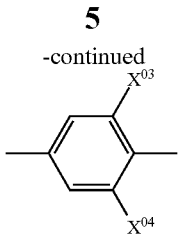

(In the structures, at least one —CH$_2$— of the cyclohexane ring is optionally replaced by —O— such that no oxygen atoms are directly adjacent to each other, at least one —CH═ of each benzene ring is optionally replaced by —N═ such that no nitrogen atoms are directly adjacent to each other, and X$^{03}$ and X$^{04}$ are each independently —H, —Cl, —F, —CF$_3$, or —OCF$_3$.)

In the formula, partial structural formula (LC0-Ph) may be formula (LC0-Np).

[Chem. 4]

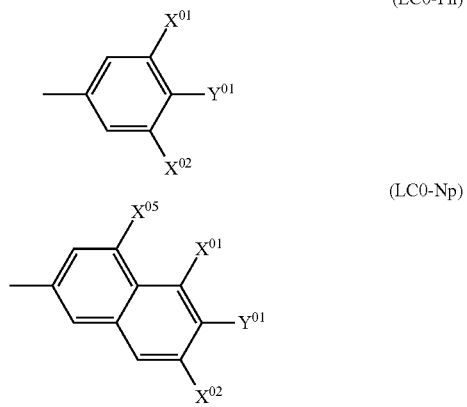

X$^{01}$, X$^{02}$ and X$^{05}$ are each independently hydrogen or fluorine.

Y$^{01}$ is —Cl, —F, —OCHF$_2$, —CF$_3$, —OCF$_3$, or a fluorinated alkyl, alkoxy, alkenyl, or alkenyloxy group of 2 to 5 carbon atoms.

Z$^{01}$ to Z$^{05}$ are each independently a single bond, —CH═CH—, —C≡C—, —CH$_2$CH$_2$—, —(CH$_2$)$_4$—, —OCH$_2$—, —CH$_2$O—, —OCF$_2$—, or —CF$_2$O—, where at least one of Z$^{01}$ to Z$^{05}$ present is —OCH$_2$—, —OCF$_2$—, or —CF$_2$O—.

W$^{01}$ and W$^{02}$ are each independently —CH$_2$— or —O—.

m$^{01}$ to m$^{03}$ are each independently an integer of 0 to 2. m$^{01}$+m$^{02}$+m$^{03}$ is 0, 1, or 2. A plurality of A$^{01}$, A$^{02}$, A$^{03}$, Z$^{01}$, Z$^{03}$, and/or Z$^{05}$, if present, may be the same or different.

Advantageous Effects of Invention

The liquid crystal composition according to the present invention has the advantage of exhibiting a positive Δε large in absolute value. The liquid crystal composition also has a low η and a low rotational viscosity (γ$_1$) and exhibits a stable liquid crystal phase over a wide temperature range because of its good liquid crystallinity. This liquid crystal composition is also chemically stable to factors such as heat, light, and moisture and has good phase stability at low temperature because of its good solubility, thereby serving as a practical and reliable liquid crystal composition requiring low driving voltage.

DESCRIPTION OF EMBODIMENTS

A liquid crystal composition according to the present invention contains at least one compound represented by general formula (LC0).

[Chem. 5]

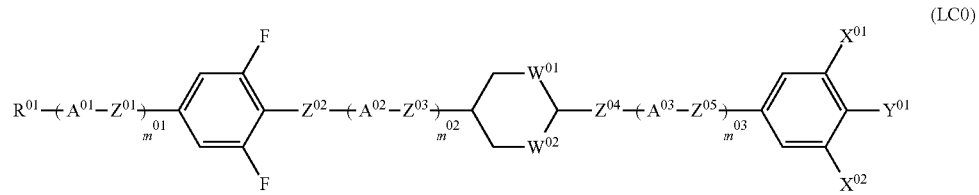

In general formula (LC0), R$^{01}$ is preferably an alkyl group of 1 to 8 carbon atoms, an alkenyl group of 2 to 8 carbon atoms, or an alkoxy group of 1 to 8 carbon atoms and is preferably linear. If R$^{01}$ is an alkenyl group, it is preferably selected from the groups represented by formulas (R1) to (R5) (where the black dots are linkages to the ring). These are preferred if A$^{01}$ is trans-1,4-cyclohexylene, and formulas (R1), (R2), and (R4) are more preferred.

[Chem. 6]

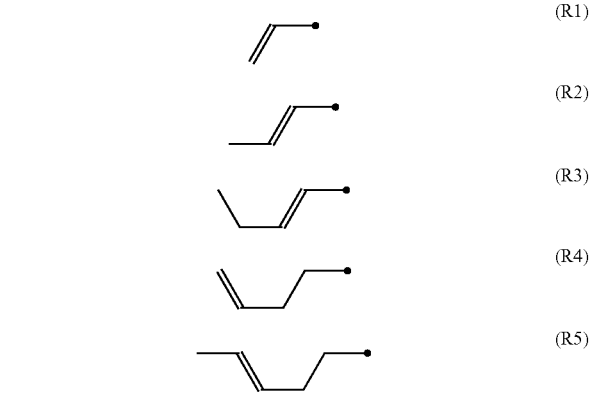

A$^{01}$ to A$^{03}$ are each independently trans-1,4-cyclohexylene, 1,4-phenylene, 3-fluoro-1,4-phenylene, 3,5-difluoro-1,4-phenylene, or tetrahydropyran. To achieve the object of the present invention, it is preferred that the liquid crystal composition contain at least one compound selected from the group consisting of these compounds.

General formula (LC0) has partial structure (LC0-Ph).

[Chem. 7]

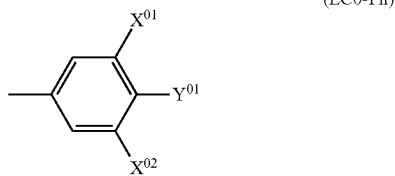
(LC0-Ph)

Partial structure (LC0-Ph) is preferably selected from those represented by the following formulas.

[Chem. 8]

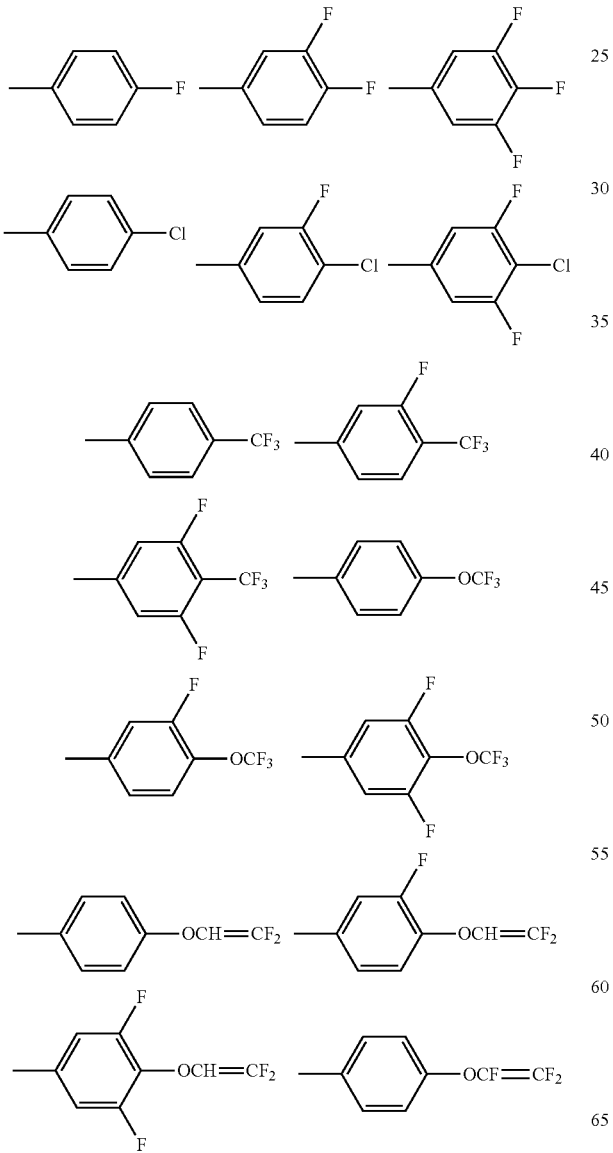

-continued

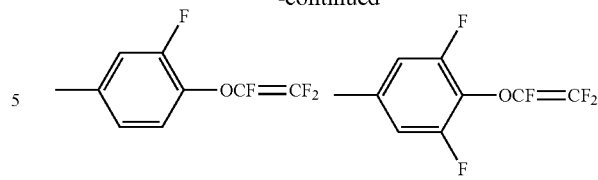

$Z^{01}$-$Z^{05}$ are preferably each independently a single bond, —CH=CH—, —C≡C—, —CH$_2$CH$_2$—, —OCF$_2$—, or —CF$_2$O—. At least one of $Z^{01}$ to $Z^{05}$ present is —OCH$_2$—, —OCF$_2$—, or —CF$_2$O—. Preferably, one of $Z^{02}$ to $Z^{05}$ is —OCF$_2$, —CF$_2$O—, or —OCH$_2$—, and more preferably, the remainder is a single bond, —OCF$_2$—, —CF$_2$O—, or —OCH$_2$—.

In the formula, partial structural formula (LC0-Ph) may be formula (LC0-Np).

[Chem. 9]

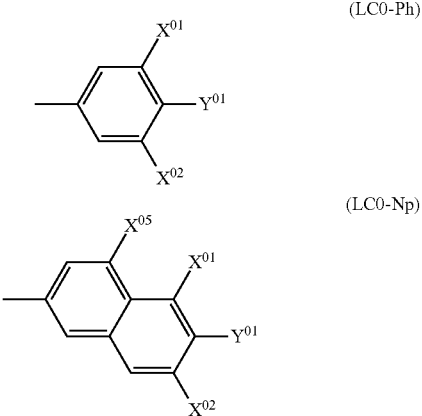

(In the formulas, $X^{01}$, $X^{02}$, and $X^{05}$ are each independently hydrogen or fluorine, and $Y^{01}$ is —Cl, —F, —OCHF$_2$, —CF$_3$, —OCF$_3$, or a fluorinated alkyl, alkoxy, alkenyl, or alkenyloxy of 2 to 5 carbon atoms.)

$X^{01}$ to $X^{05}$ are preferably F, which results in a significantly low viscosity (η) for a larger or similar dielectric anisotropy (Δε). Preferably, there are 2 to 7 F substituents in general formula (LC0), including the two already shown in general formula (LC0).

It is particularly preferred to use a combination of compounds where $Y^{01}$ is F, CF$_3$, OCF$_3$, —OCF=CF$_2$, or —OCH=CF$_2$, which lowers the lower temperature limit of the nematic phase and improves the low-temperature operation and storage stability of the liquid crystal composition.

$m^{01}$ to $m^{03}$ may each independently be an integer of 0 to 2. It is particularly preferred to use a combination of a compound where $m^{01}$+$m^{02}$+$m^{03}$ is 0 and a compound where $m^{01}$+$m^{02}$+$m^{03}$ is 1.

The compound represented by general formula (LC0) is preferably a compound satisfying at least one of the following conditions.

a compound where $Z^{01}$ is present and is —OCH$_2$—, —OCF$_2$—, or —CF$_2$O— a compound where $Z^{02}$ is —OCH$_2$—, —OCF$_2$—, or —CF$_2$O— a compound where $Z^{03}$ is present and is —OCH$_2$—, —OCF$_2$—, or —CF$_2$O— a compound where $Z^{04}$ is —OCH$_2$—, —OCF$_2$—, or —CF$_2$O— a compound where $Z^{05}$ is present and is —OCH$_2$—, —OCF$_2$—, or —CF$_2$O— a compound where both $W^{01}$ and $W^{02}$ are —CH$_2$—
a compound where one of $W^{01}$ and $W^{02}$ is —O—
a compound where both $W^{01}$ and $W^{02}$ are —O—
a compound where $m^{01}+m^{02}+m^{03}$ is 0
a compound where $m^{01}$ is 0, $m^{02}$ is 0, and $m^{03}$ is 1
a compound where $m^{01}$ is 0, $m^{02}$ is 1, and $m^{03}$ is 0
a compound where $m^{01}$ is 1, $m^{02}$ is 0, and $m^{03}$ is 0
a compound where $m^{01}$ is 1, $m^{02}$ is 0, and $m^{03}$ is 1
a compound where $m^{01}$ is 1, $m^{02}$ is 1, and $m^{03}$ is 0
a compound where $m^{01}$ is 0, $m^{02}$ is 1, and $m^{03}$ is 1
a compound where $m^{01}$ is 2, one $Z^{01}$ is —OCH$_2$—, —OCF$_2$—, or —CF$_2$O—, and the other $Z^{01}$ is a single bond
a compound where $m^{02}$ is 1 or 2, one of $Z^{02}$ and $Z^{03}$ is —OCH$_2$—, —OCF$_2$—, or —CF$_2$O—, and the remainder is a single bond
a compound where $m^{03}$ is 1 or 2, one of $Z^{04}$ and $Z^{05}$ is —OCH$_2$—, —OCF$_2$—, or —CF$_2$O—, and the remainder is a single bond More preferably, the liquid crystal compound represented by general formula (LC0) is a compound represented by any of general formulas (LC0-a) to (LC0-d) below (where $R^{01}$, $A^{01}$ to $A^{03}$, $Z^{01}$ to $Z^{05}$, $X^{01}$, $X^{02}$, and $Y^{01}$ are as defined in general formula (LC0), and if two or more are present, each may be the same or different). The liquid crystal composition according to the present invention preferably contains, as the compound represented by general formula (LC0), at least one of compounds represented by (LC0-a) to (LC0-d).

[Chem. 10]

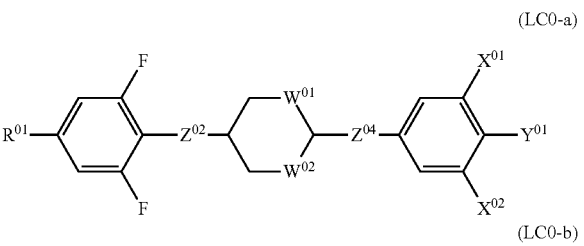

(LC0-a)

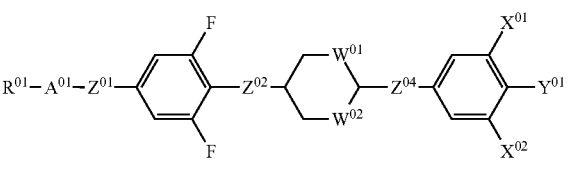

(LC0-b)

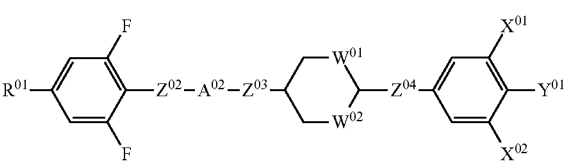

(LC0-c)

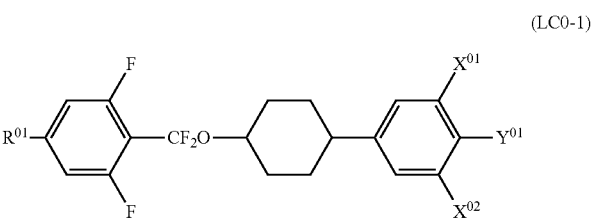

(LC0-d)

Even more preferably, the compound represented by general formula (LC0) is a compound represented by any of general formulas (LC0-1) to (LC0-74) below. In particular, compounds represented by general formulas (LC0-1) to (LC0-9) are preferred since they have a large dielectric anisotropy ($\Delta\varepsilon$), a significantly low viscosity ($\eta$), and good general formula (LC0-10) to (LC0-67) are preferred since they have a large dielectric anisotropy ($\Delta\varepsilon$), a relatively low viscosity ($\eta$), and a high nematic phase-isotropic liquid phase transition temperature ($T_{ni}$).

Still more preferably, the liquid crystal composition containing the compound represented by general formula (LC0) satisfies at least one of the following conditions.

containing a compound represented by any of general formulas (LC0-2) to (LC0-9) in an amount of at most 40% by mass containing a compound represented by any of general formulas (LC0-10) to (LC0-18) in an amount of at most 60% by mass containing a compound represented by any of general formulas (LC0-28) to (LC0-38) in an amount of at most 60% by mass containing a compound represented by any of general formulas (LC0-48) to (LC0-51) in an amount of at most 30% by mass containing a compound represented by any of general formulas (LC0-52) and (LC0-53) in an amount of at most 40% by mass containing a compound represented by any of general formulas (LC0-56) to (LC0-59) in an amount of at most 50% by mass containing a compound represented by any of general formulas (LC0-60) to (LC0-67) in an amount of at most 20% by mass containing a compound represented by any of general formulas (LC0-68) to (LC0-74) in an amount of at most 15% by mass containing at least one compound selected from the group consisting of compounds represented by general formulas (LC0-2) to (LC0-5), (LC0-7), (LC0-11) to (LC0-15), (LC0-17), (LC0-18), (LC0-20), (LC0-28) to (LC0-30), (LC0-34), (LC0-35), (LC0-39), (LC0-41), (LC0-45), (LC0-46), (LC0-56) to (LC0-61), (LC0-68), and (LC0-74)

[Chem. 11]

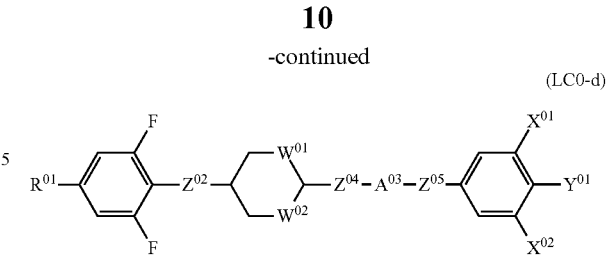

(LC0-1) (LC0-2)

-continued (LC0-3), (LC0-4), (LC0-5), (LC0-6), (LC0-7), (LC0-8), (LC0-9)

[Chem. 12]

(LC0-10), (LC0-11), (LC0-12), (LC0-13), (LC0-14), (LC0-15), (LC0-16), (LC0-17)

-continued
(LC0-18)
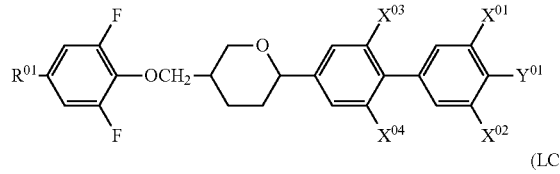
(LC0-19)
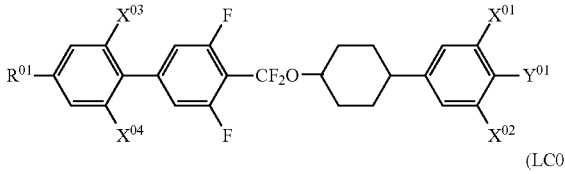
(LC0-20)
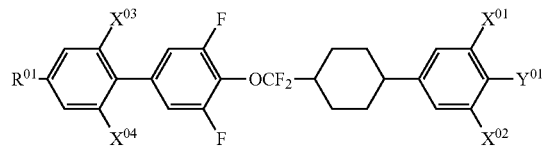
(LC0-21)
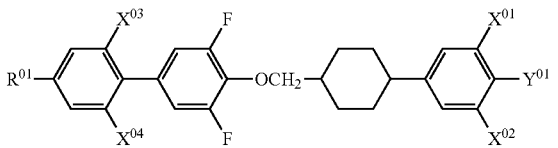
(LC0-22)
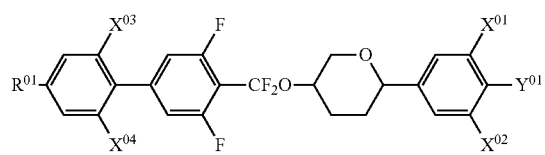
(LC0-23)
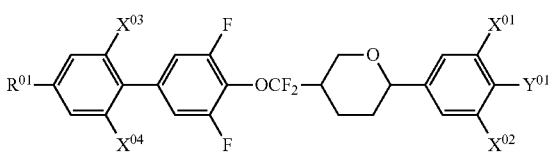
(LC0-24)
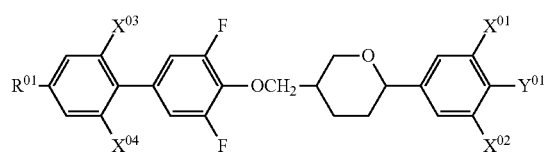
(LC0-25)
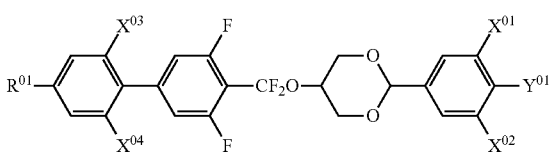
(LC0-26)
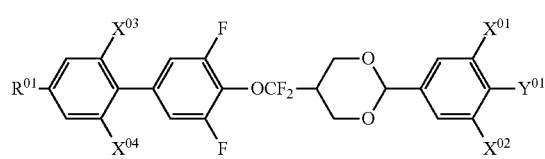
(LC0-27)
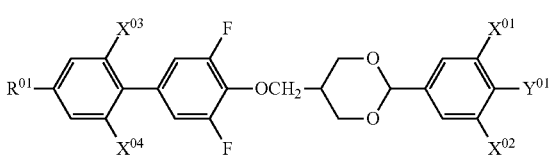
[Chem. 13]
(LC0-28)
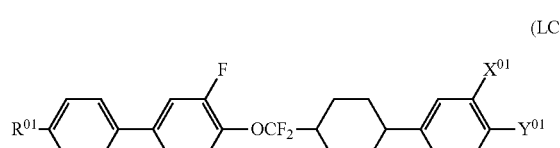
(LC0-29)
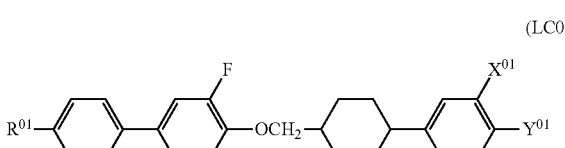
(LC0-30)
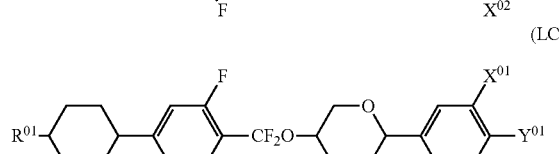
(LC0-31)
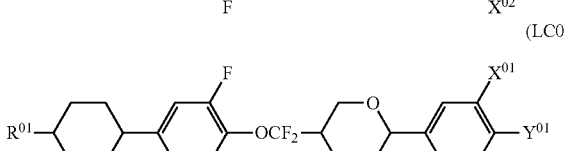
(LC0-32)
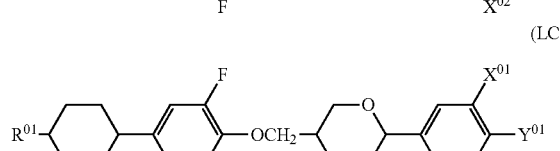
(LC0-33)
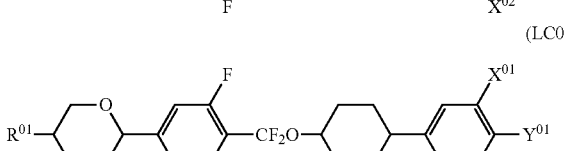
(LC0-34)
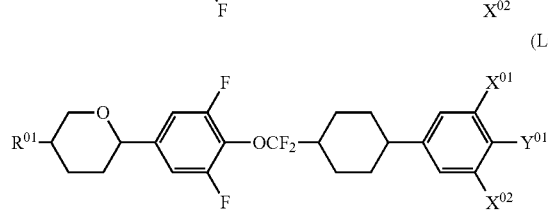
(LC0-35)
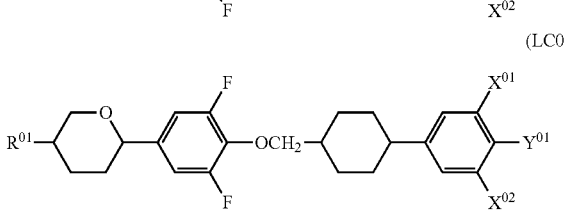

-continued
(LC0-36)
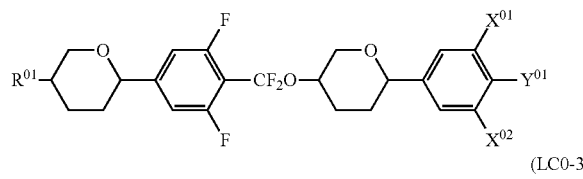
(LC0-37)
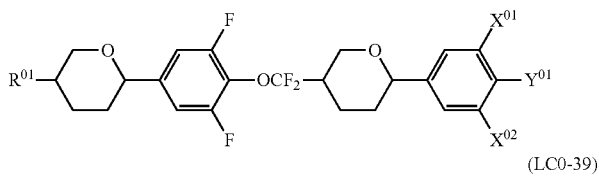
(LC0-38)
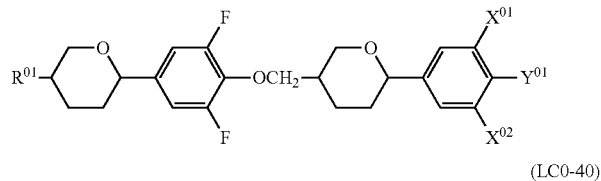
(LC0-39)
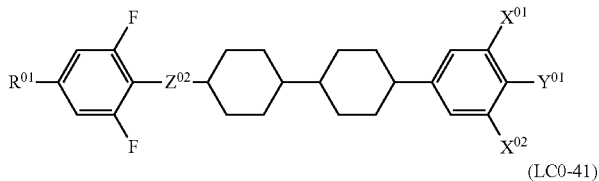
(LC0-40)
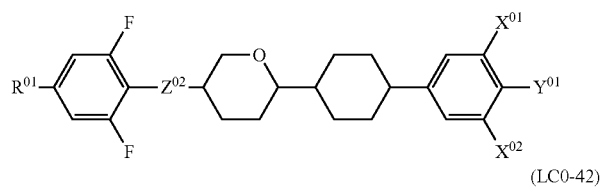
(LC0-41)
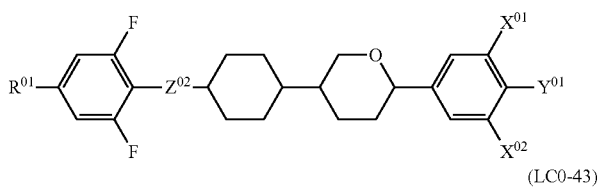
(LC0-42)
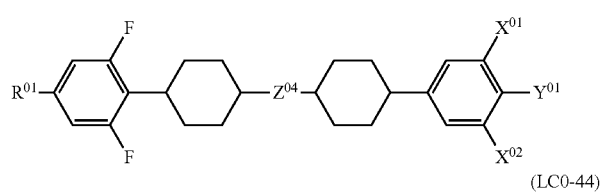
(LC0-43)
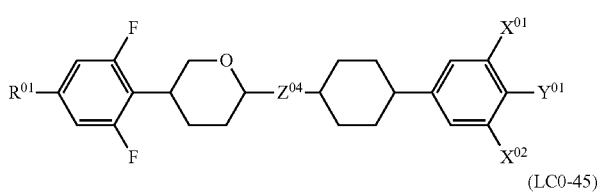
(LC0-44)
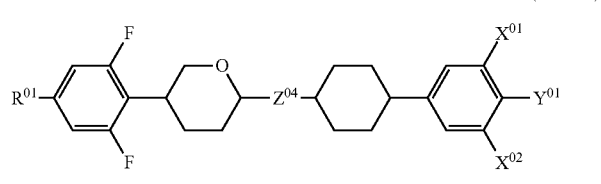
(LC0-45)
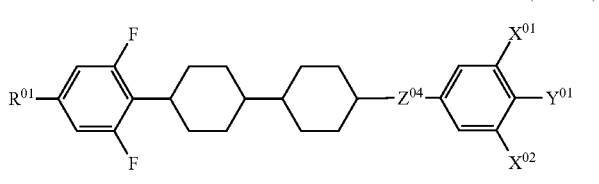
(LC0-46)
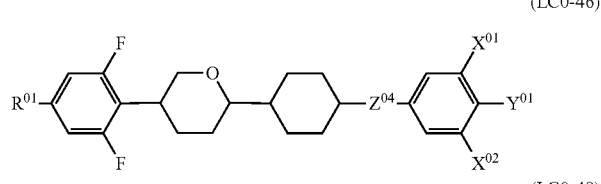
(LC0-47)
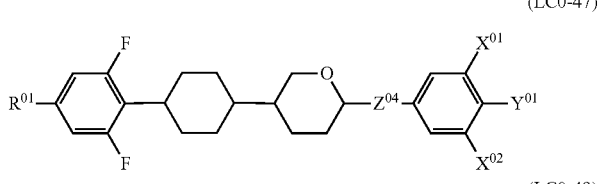
(LC0-48)
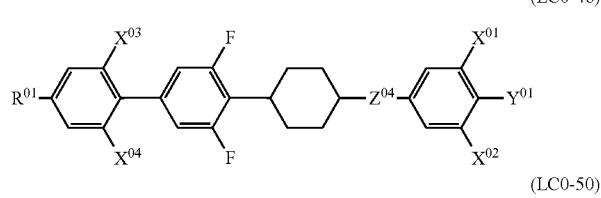
(LC0-49)
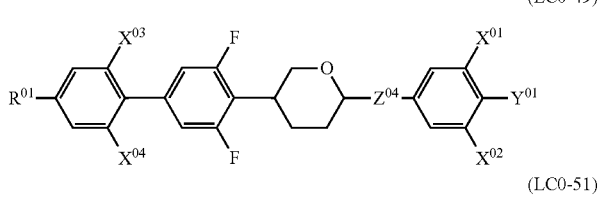
(LC0-50)
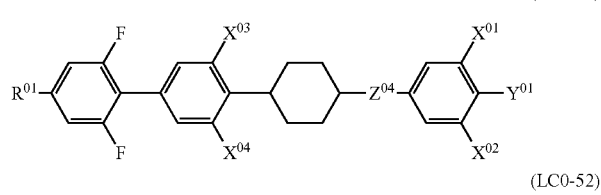
(LC0-51)
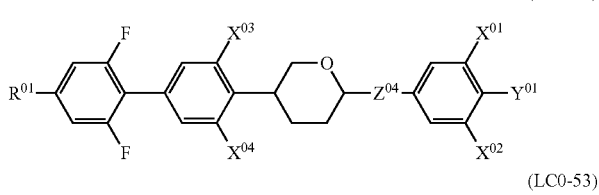
(LC0-52)
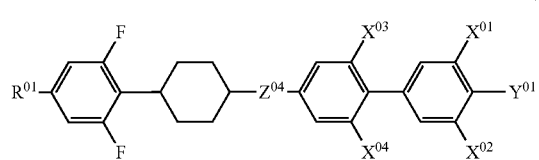
(LC0-53)
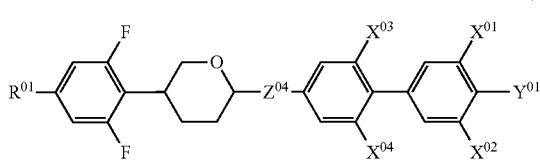

(LC0-54)
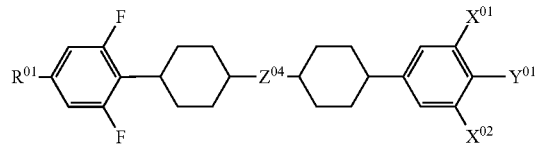
(LC0-55)
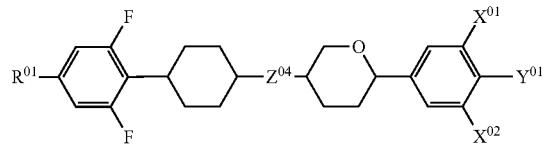
[Chem. 14]
(LC0-56)
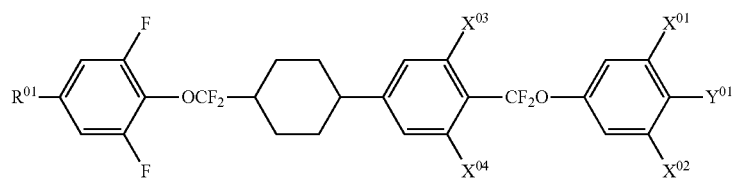
(LC0-57)
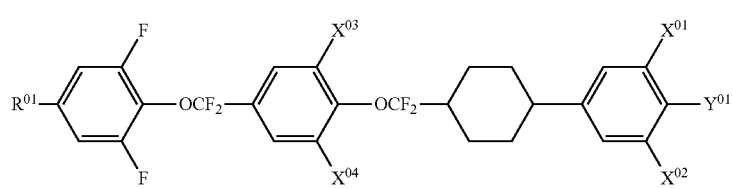
(LC0-58)
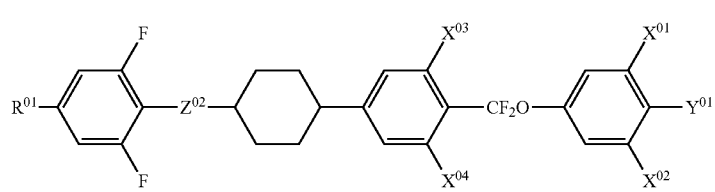
(LC0-59)
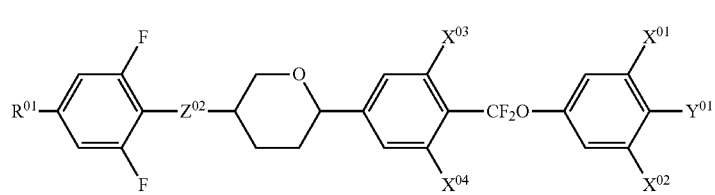
(LC0-68)
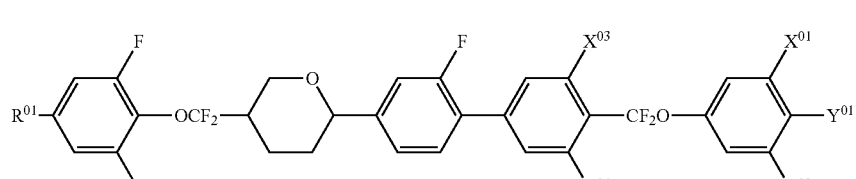
(LC0-69)
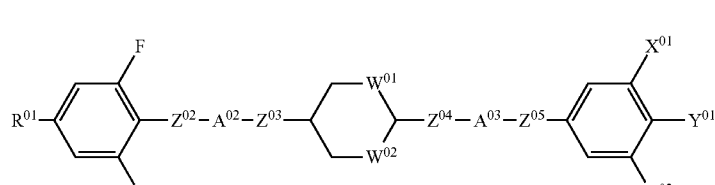
(LC0-70)
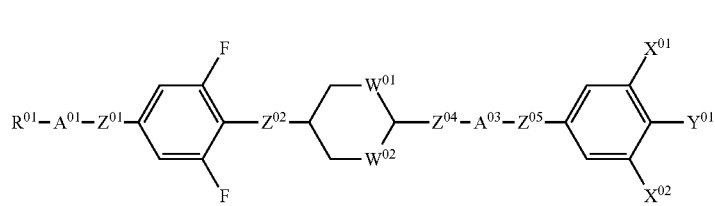

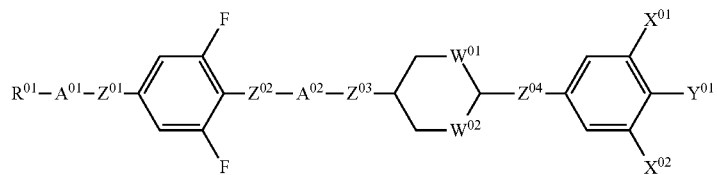
(LC0-71)

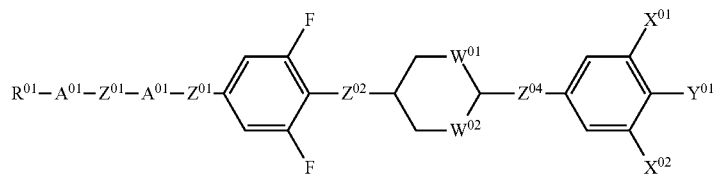
(LC0-72)

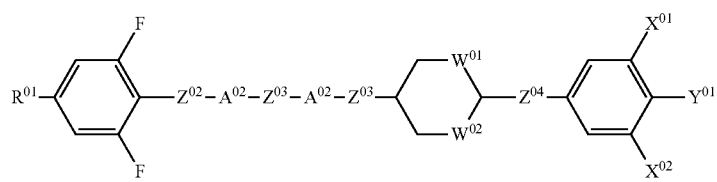
(LC0-73)

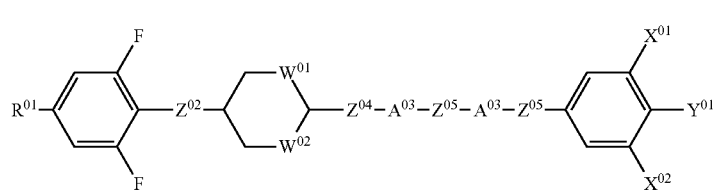
(LC0-74)

(In the formulas, $R^{01}$, $A^{01}$ to $A^{03}$, $Z^{01}$ to $Z^{01}$, $X^{01}$ to $X^{04}$, $W^{01}$, $W^{02}$, and $Y^{01}$ are as defined in Claim 1.)

Preferably, a compound of general formula (LC0) where $R^{01}$ is an alkyl group of 1 to 5 carbon atoms or an alkenyl group of 2 to 5 carbon atoms and $Y^{01}$ is —Cl, —F, —OCHF$_2$, —CF$_3$, —OCF$_3$, —CF$_2$CF$_3$, —CHFCF$_3$, —OCF$_2$CF$_3$, —OCHFCF$_3$, —OCF=CF$_2$, or —OCH=CF$_2$ is present in an amount of at most 70% by mass.

The liquid crystal composition according to the present invention preferably further contains at least one compound selected from the group consisting of compounds represented by general formulas (LC1) to (LC5). Particularly preferred is a liquid crystal composition containing at least one compound represented by general formula (LC0) and satisfying at least one of the following conditions.

containing a compound represented by general formula (LC1) in an amount of at most 20% by mass containing a compound represented by general formula (LC2) in an amount of at most 40% by mass containing a compound represented by general formula (LC3) in an amount of at most 50% by mass containing a compound represented by general formula (LC4) in an amount of at most 60% by mass containing a compound represented by general formula (LC5) in an amount of at most 75% by mass

[Chem. 15]

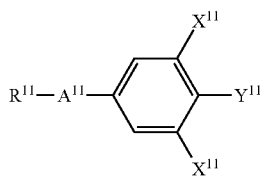
(LC1)

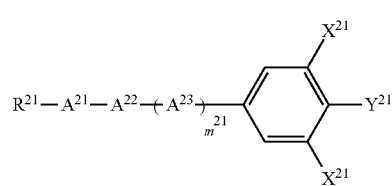
(LC2)

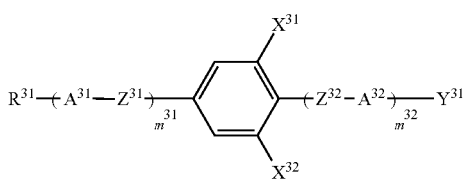
(LC3)

-continued (LC4)

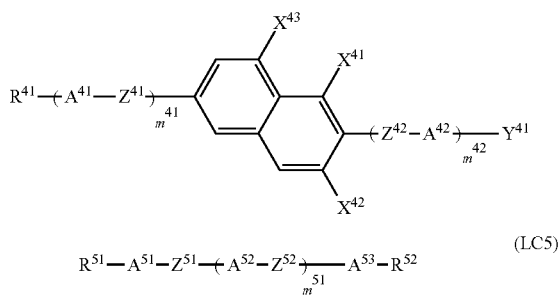

(LC5)

$$R^{51}-A^{51}-Z^{51}-(A^{52}-Z^{52})_{m^{51}}-A^{53}-R^{52}$$

In the formulas, $R^{11}$ to $R^{41}$ are each independently an alkyl group of 1 to 15 carbon atoms, where at least one —$CH_2$— of the alkyl group is optionally replaced by —O—, —CH=CH—, —CO—, —OCO—, —COO—, —C≡C—, —$CF_2O$—, or —$OCF_2$— such that no oxygen atoms are directly adjacent to each other, and at least one hydrogen atom of the alkyl group is optionally replaced by halogen. $R^{51}$ and $R^{52}$ are each independently an alkyl group of 1 to 15 carbon atoms, where at least one —$CH_2$— of the alkyl group is optionally replaced by —O—, —CH=CH—, —CO—, —OCO—, —COO—, or —C≡C— such that no oxygen atoms are directly adjacent to each other. If $A^{51}$ or $A^{53}$, described later, is a cyclohexane ring, $R^{51}$ or $R^{52}$ may be —$OCF_3$, —$CF_3$, —OCF=$CF_2$, or —OCH=$CF_2$. $A^{11}$ to $A^{42}$ are each independently any of the following structures.

[Chem. 16]

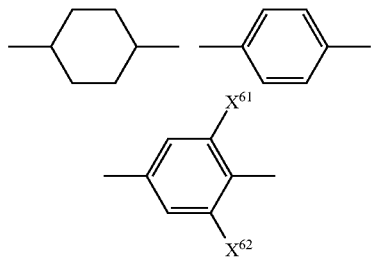

(In the structures, at least one —$CH_2$— of the cyclohexane ring is optionally replaced by —O— such that no oxygen atoms are directly adjacent to each other, at least one —CH= of each benzene ring is optionally replaced by —N= such that no nitrogen atoms are directly adjacent to each other, and $X^{61}$ and $X^{62}$ are each independently —H, —Cl, —F, —$CF_3$, or —$OCF_3$.) $A^{51}$ to $A^{53}$ are each independently any of the following structures.

[Chem. 17]

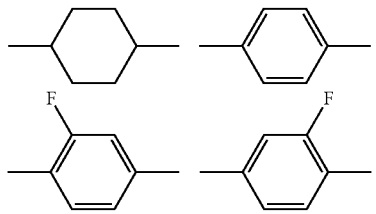

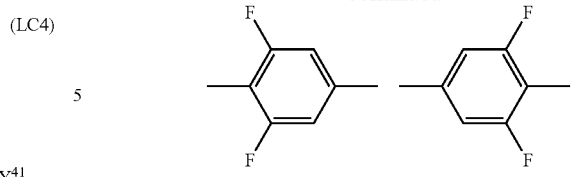

(In the formulas, at least one —$CH_2CH_2$— of the cyclohexane ring is optionally replaced by —CH=CH—, —$CF_2O$—, or —$OCF_2$—, and at least one —CH= of each benzene ring is optionally replaced by —N= such that no nitrogen atoms are directly adjacent to each other). $X^{11}$ to $X^{43}$ are each independently —H, —Cl, —F, —$CF_3$, or —$OCF_3$. $Y^{11}$ to $Y^{41}$ are —Cl, —F, —$CF_3$, —$OCF_3$, —$CF_2CF_3$, —$CHFCF_3$, —$OCF_2CF_3$, —$OCHFCF_3$, or —OCF=$CF_2$. $Z^{31}$ to $Z^{42}$ are each independently a single bond, —CH=CH—, —C≡C—, —$CH_2CH_2$—, —$(CH_2)_4$—, —$OCH_2$—, —$CH_2O$—, —$OCF_2$—, or —$CF_2O$—, where at least one of $Z^{31}$ and $Z^{32}$ present is not a single bond. $Z^{51}$ and $Z^{52}$ are each independently a single bond, —CH=CH—, —C≡C—, —$CH_2CH_2$—, —$(CH_2)_4$—, —$OCH_2$—, —$CH_2O$—, —$OCF_2$—, or —$CF_2O$—. $m^{11}$ to $m^{51}$ are each independently an integer of 0 to 3. $m^{31}+m^{32}$ and $m^{41}+m^{42}$ are each independently 1, 2, 3, or 4. A plurality of $A^{23}$, $A^{31}$, $A^{32}$, $A^{41}$, $A^{42}$, $A^{52}$, $Z^{31}$, $Z^{32}$, $Z^{41}$, $Z^{42}$, and/or $Z^{52}$, if present, may be the same or different. Compounds represented by general formula (LC0) are excluded.

In general formulas (LC1) to (LC5), $R^{11}$ to $R^{41}$ are each independently an alkyl group of 1 to 15 carbon atoms, where at least one —$CH_2$— of the alkyl group is optionally replaced by —O—, —CH=CH—, —CO—, —OCO—, —COO—, —C≡C—, —$CF_2O$—, or —$OCF_2$— such that no oxygen atoms are directly adjacent to each other, and at least one hydrogen atom of the alkyl group is optionally replaced by halogen. $R^{11}$ to $R^{41}$ are preferably an alkyl group of 1 to 8 carbon atoms, an alkenyl group of 2 to 8 carbon atoms, or an alkoxy group of 1 to 8 carbon atoms and are preferably linear. $R^{51}$ and $R^{52}$ are each independently an alkyl group of 1 to 15 carbon atoms, where at least one —$CH_2$— of the alkyl group is optionally replaced by —O—, —CH=CH—, —CO—, —OCO—, —COO—, or —C≡C— such that no oxygen atoms are directly adjacent to each other. $R^{51}$ and $R^{52}$ are preferably an alkyl group of 1 to 8 carbon atoms, an alkenyl group of 2 to 8 carbon atoms, or an alkoxy group of 1 to 8 carbon atoms and are preferably linear. If $R^{11}$ to $R^{52}$ are alkenyl groups, they are preferably selected from the groups represented by formulas (R1) to (R5).

[Chem. 18]

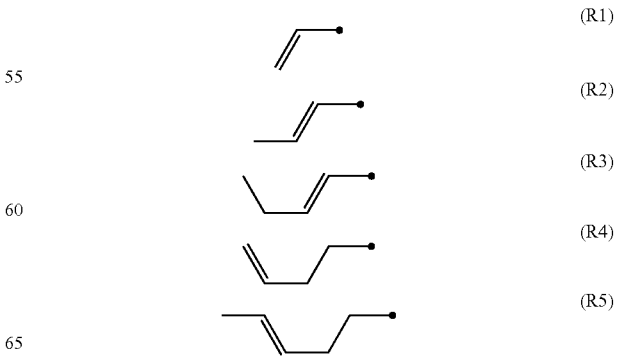

(In the formulas, the black dots are linkages to the ring.)

$A^{11}$ to $A^{42}$ are each independently trans-1,4-cyclohexylene, 1,4-phenylene, 3-fluoro-1,4-phenylene, 3,5-difluoro-1,4-phenylene, or tetrahydropyran. If any of $A^{11}$ to $A^{42}$ is tetrahydropyran, $A^{11}$, $A^{21}$, or $A^{31}$ is preferably tetrahydropyran. $A^{51}$ to $A^{53}$ are preferably each independently trans-1,4-cyclohexylene, 1,4-phenylene, 2-fluoro-1,4-phenylene, or 3-fluoro-1,4-phenylene.

$X^{11}$ to $X^{43}$ are preferably each independently hydrogen or fluorine. $Y^{11}$ to $Y^{41}$ are preferably —F, —$CF_3$, or —$OCF_3$. $Z^{31}$ to $Z^{42}$ are preferably each independently a single bond, —CH=CH—, —C≡C—, —$CH_2CH_2$—, —$(CH_2)_4$—, —$OCH_2$—, —$CH_2O$—, —$OCF_2$—, or —$CF_2O$—, where at least one of $Z^{31}$ and $Z^{32}$ present is not a single bond. If $m^{42}$ is 0, $Z^{41}$ is each independently a single bond, —CH=CH—, —C≡C—, —$CH_2CH_2$—, or —$(CH_2)_4$—. $Z^{51}$ and $Z^{52}$ are preferably each independently a single bond, —CH=CH—, —C≡C—, —$CH_2CH_2$—, —$(CH_2)_4$—, —$OCH_2$—, —$CH_2O$—, —$OCF_2$—, or —$CF_2O$—, more preferably a single bond, —$CH_2CH_2$—, —$OCF_2$—, or —$CF_2O$—, even more preferably a single bond. $m^{21}$ is preferably an integer of 0 or 1. $m^{31}$ to $m^4$ are preferably each independently an integer of 0 to 2, and $m^{31}+m^{32}$ and $m^{41}+m^{42}$ are preferably each independently 1, 2, or 3. $m^{51}$ is preferably an integer of 1 or 2. A plurality of $A^{23}$, $A^{31}$, $A^{32}$, $A^{41}$, $A^{42}$, $A^{52}$, $Z^{31}$, $Z^{32}$, $Z^{41}$, $Z^{42}$, and/or $Z^{52}$, if present, may be the same or different.

The compound represented by general formula (LC1) is preferably a compound represented by any of general formulas (LC1-1) to (LC1-4).

[Chem. 19]

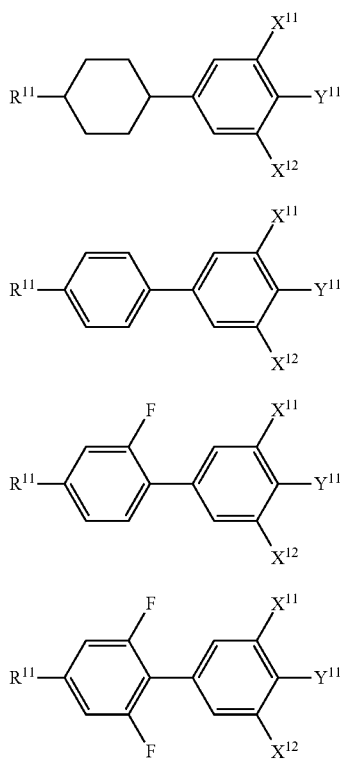

(In the formulas, $R^{11}$ is an alkyl group of 1 to 15 carbon atoms, where at least one —$CH_2$— of the alkyl group is optionally replaced by —O—, —CH=CH—, —CO—, —OCO—, —COO—, —C≡C—, —$CF_2O$—, or —$OCF_2$— such that no oxygen atoms are directly adjacent to each other, and at least one hydrogen atom of the alkyl group is optionally replaced by halogen; $X^{11}$ and $X^{12}$ are each independently —H, —Cl, —F, —$CF_3$, or —$OCF_3$; and $Y^1$ is —Cl, —F, —$CF_3$, —$OCF_3$, —$CF_2CF_3$, —$CHFCF_3$, —$OCF_2CF_3$, —$OCHFCF_3$, or —OCF=$CF_2$.)

The compound represented by general formula (LC2) is preferably a compound represented by any of general formulas (LC2-1) to (LC2-14).

[Chem. 20]

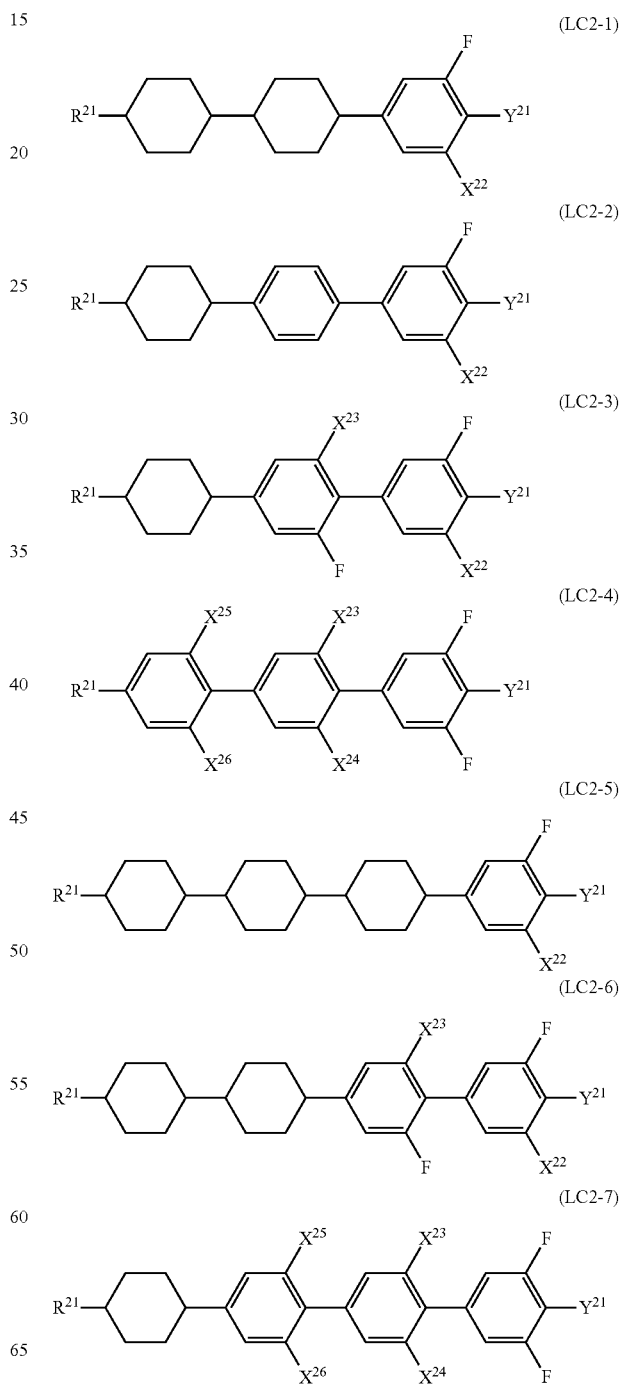

-continued

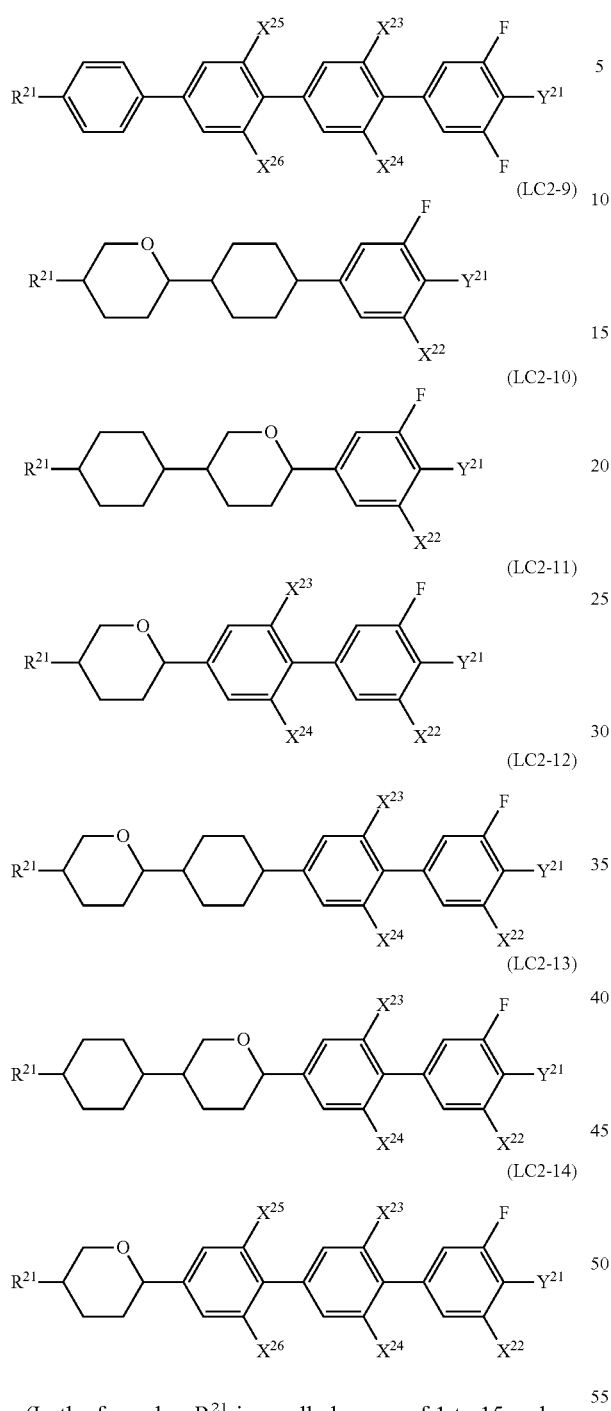

(In the formulas, $R^{21}$ is an alkyl group of 1 to 15 carbon atoms, where at least one —CH$_2$— of the alkyl group is optionally replaced by —O—, —CH=CH—, —CO—, —OCO—, —COO—, —C≡C—, —CF$_2$O—, or —OCF$_2$— such that no oxygen atoms are directly adjacent to each other, and at least one hydrogen atom of the alkyl group is optionally replaced by halogen; $X^{22}$ to $X^{26}$ are each independently —H, —Cl, —F, —CF$_3$, or —OCF$_3$; and $Y^{21}$ is —Cl, —F, —CF$_3$, —OCF$_3$, —CF$_2$CF$_3$, —CHFCF$_3$, —OCF$_2$CF$_3$, —OCHFCF$_3$, or —OCF=CF$_2$.)

The compound represented by general formula (LC3) is preferably a compound selected from the group consisting of compounds represented by general formulas (LC3-1) to (LC3-32) and/or the group consisting of compounds represented by general formulas (LC3-0-1) to (LC3-0-97).

[Chem. 21]

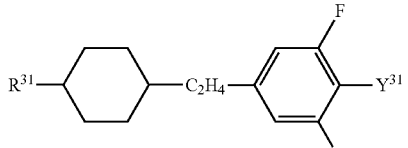
(LC3-1)

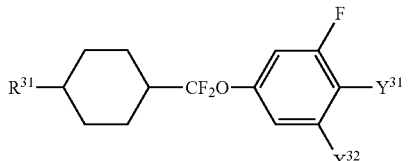
(LC3-2)

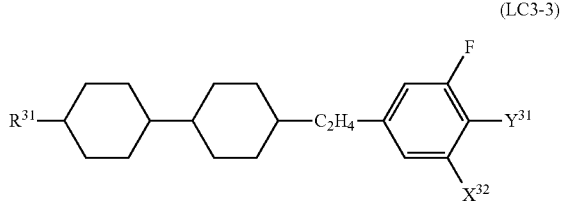
(LC3-3)

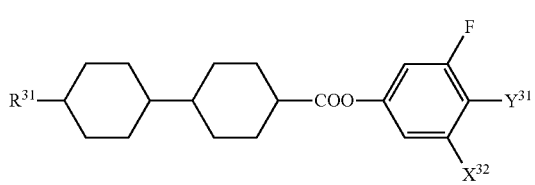
(LC3-4)

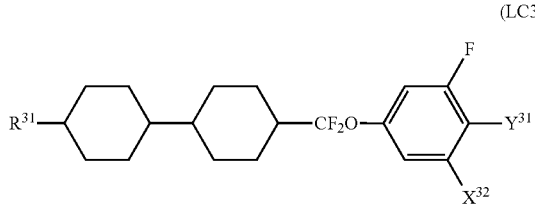
(LC3-5)

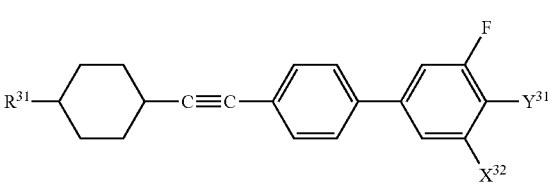
(LC3-6)

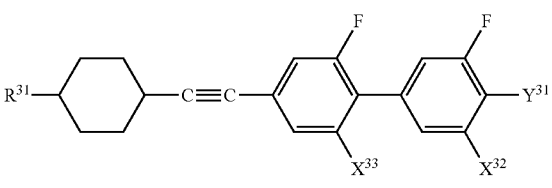
(LC3-7)

-continued
(LC3-8)
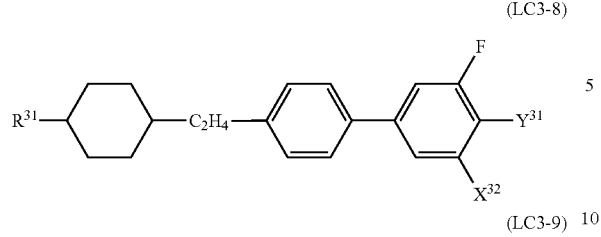
(LC3-9)
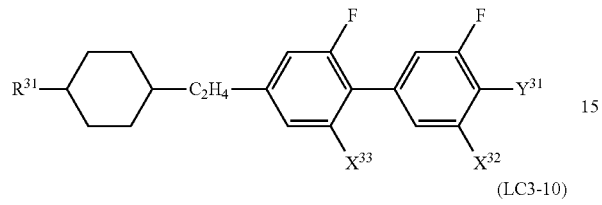
(LC3-10)
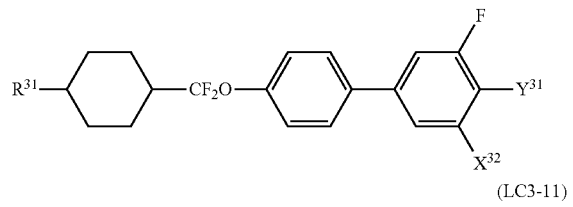
(LC3-11)
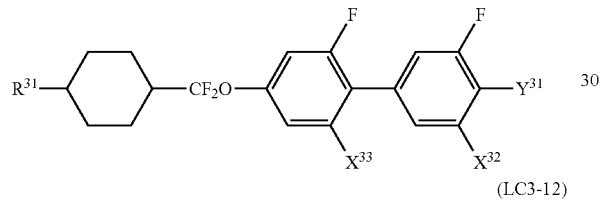
(LC3-12)
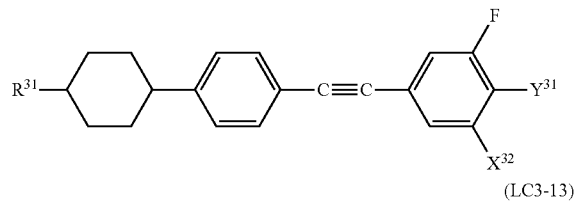
(LC3-13)
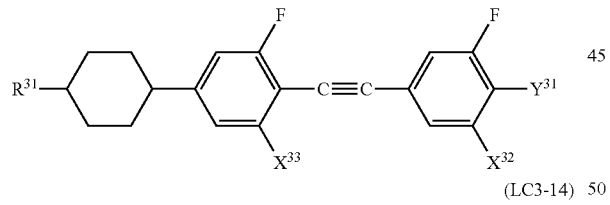
(LC3-14)
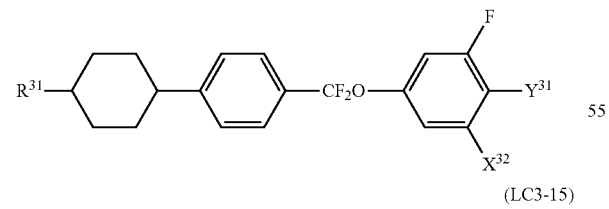
(LC3-15)
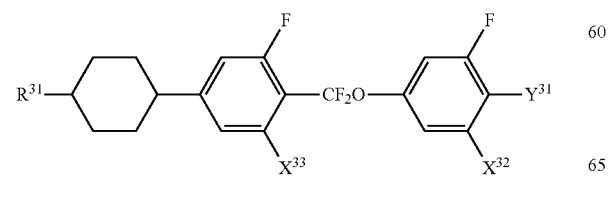
[Chem. 22]
-continued
(LC3-16)
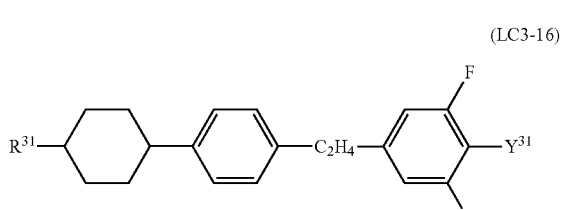
(LC3-17)
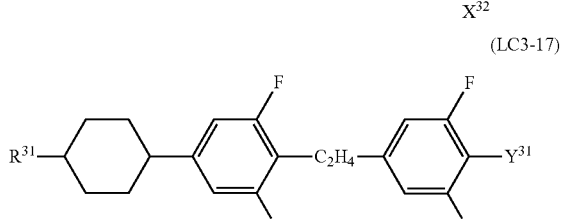
(LC3-18)
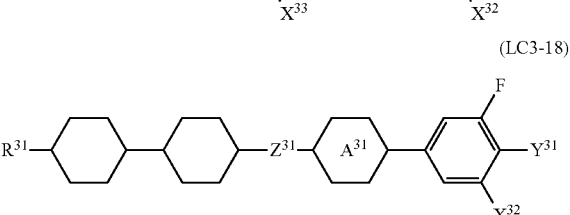
(LC3-19)
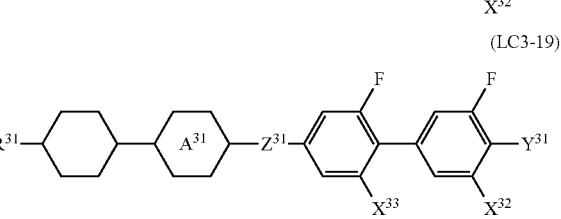
(LC3-20)
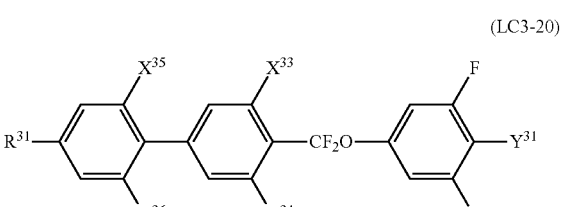
(LC3-21)
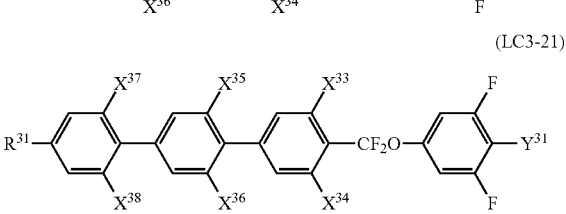
(LC3-22)
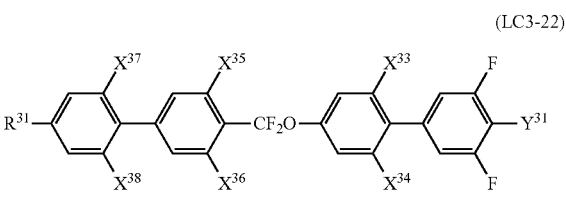
(LC3-23)
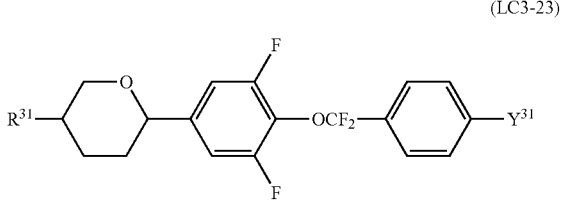

-continued
(LC3-24)
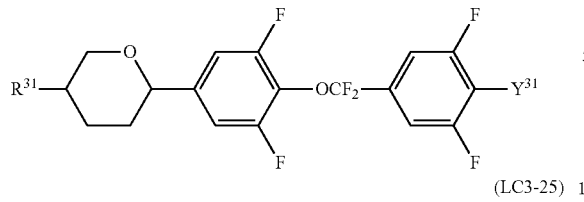
(LC3-25)
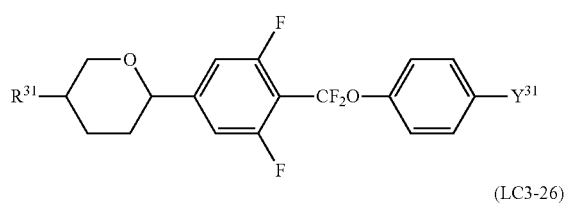
(LC3-26)
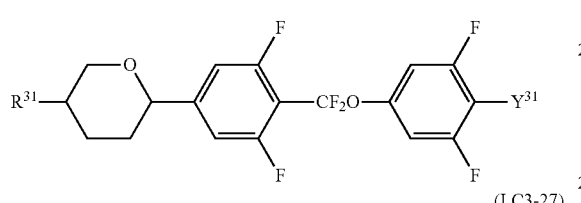
(LC3-27)
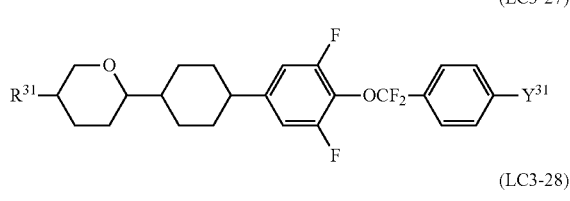
(LC3-28)
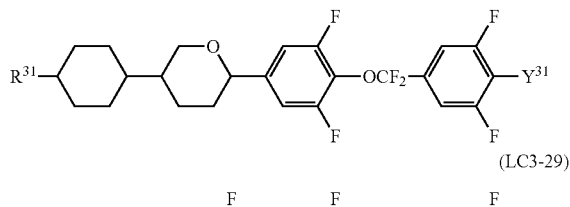
(LC3-29)
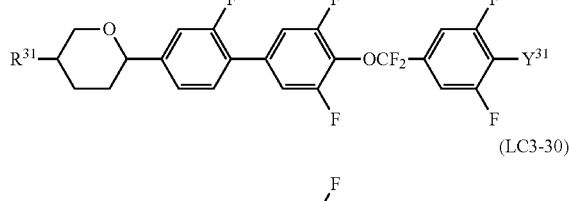
(LC3-30)
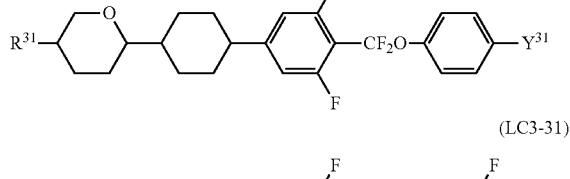
(LC3-31)
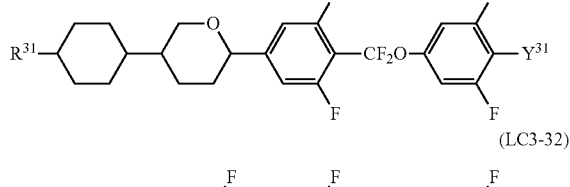
(LC3-32)
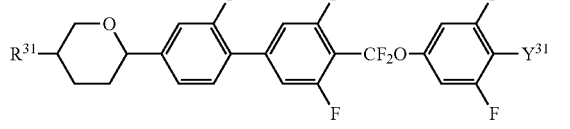
-continued
[Chem. 23]
(LC3-0-1)
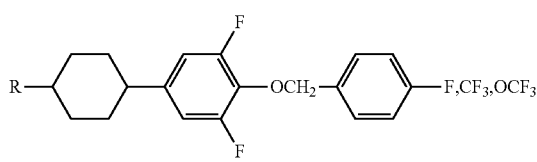
(LC3-0-2)
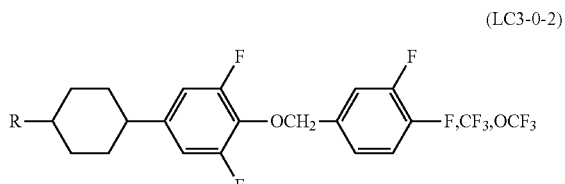
(LC3-0-3)
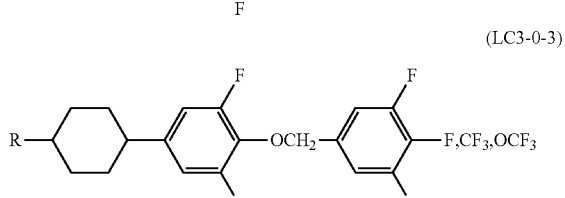
(LC3-0-4)
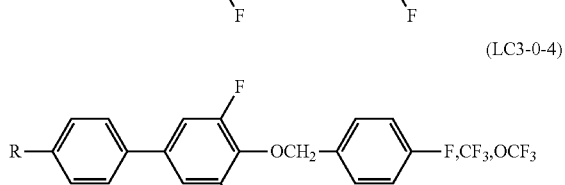
(LC3-0-5)
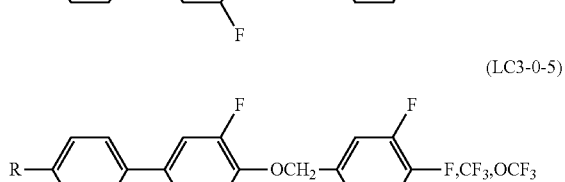
(LC3-0-6)
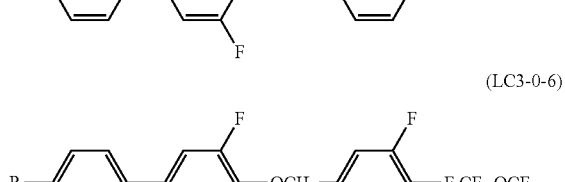
(LC3-0-7)
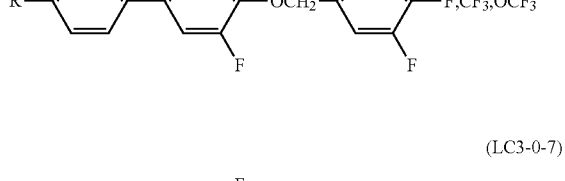
(LC3-0-8)
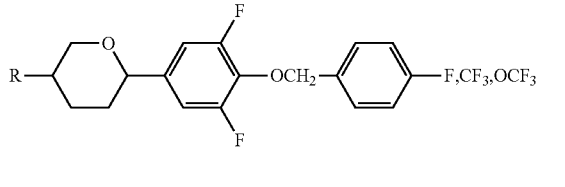
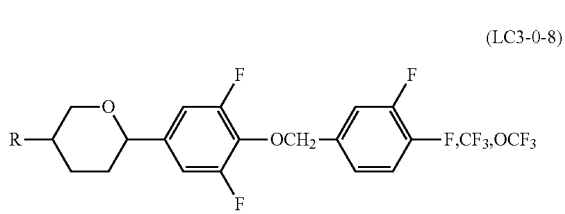

-continued
(LC3-0-9)
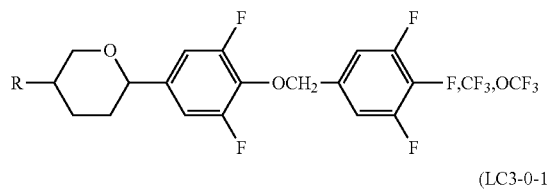
(LC3-0-10)
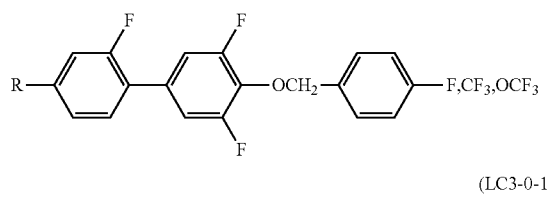
(LC3-0-11)
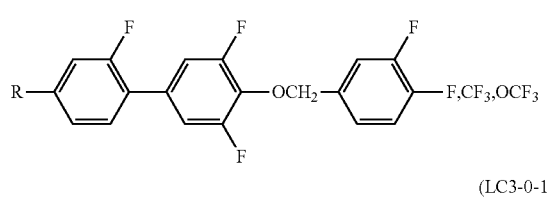
(LC3-0-12)
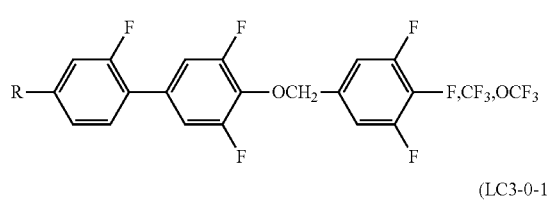
(LC3-0-13)
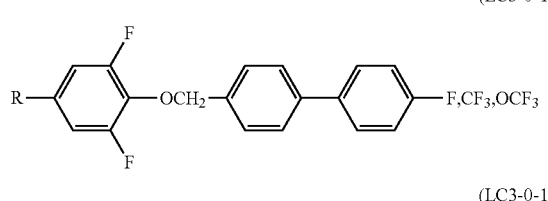
(LC3-0-14)
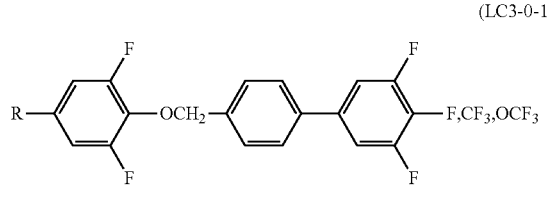
(LC3-0-15)
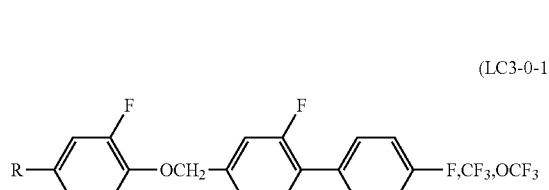
(LC3-0-16)
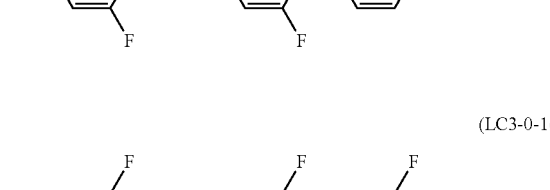
[Chem. 24]
-continued
(LC3-0-17)
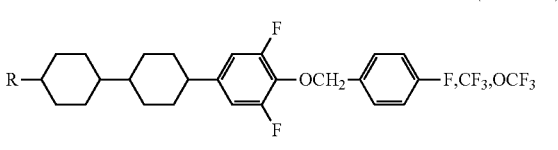
(LC3-0-18)
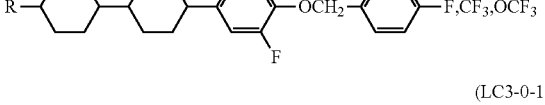
(LC3-0-19)
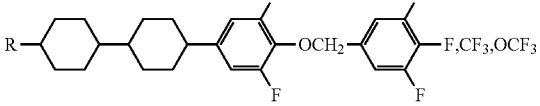
(LC3-0-20)
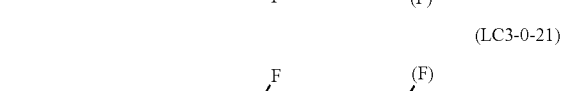
(LC3-0-21)
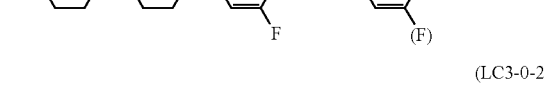
(LC3-0-22)
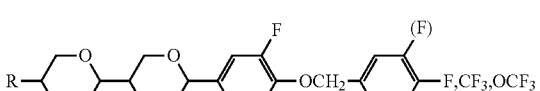
(LC3-0-23)
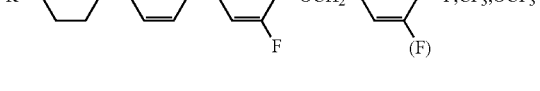
(LC3-0-24)
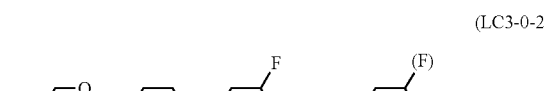
(LC3-0-25)
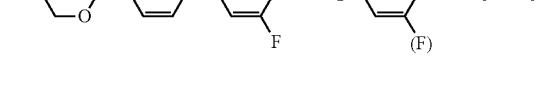

(LC3-0-26) 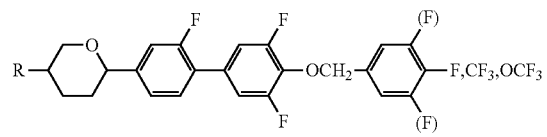
(LC3-0-27) 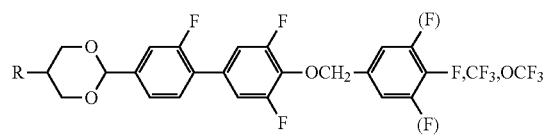
(LC3-0-28) 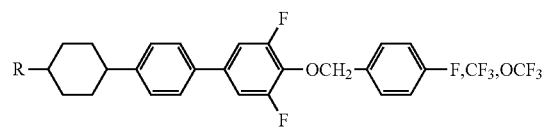
(LC3-0-29) 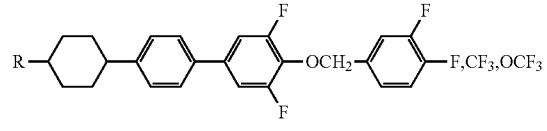
(LC3-0-30) 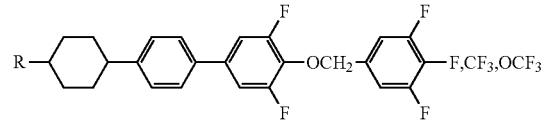
(LC3-0-31) 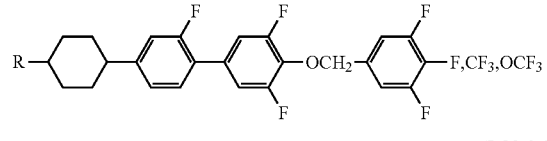
(LC3-0-32) 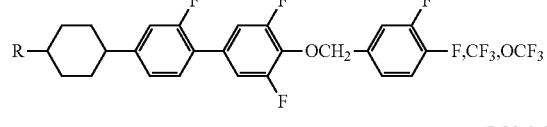
(LC3-0-33) 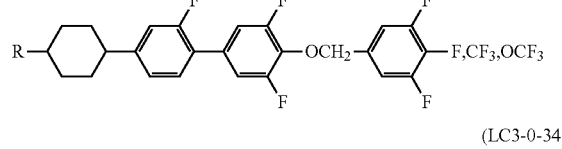
(LC3-0-34) 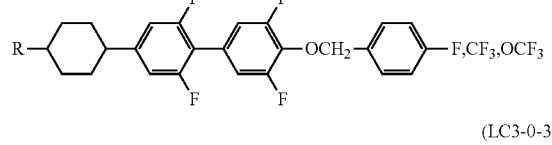
(LC3-0-35) 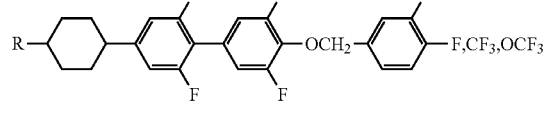
(LC3-0-36) 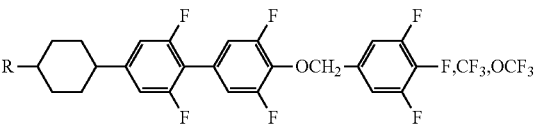
(LC3-0-37) 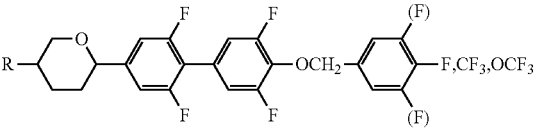
(LC3-0-38) 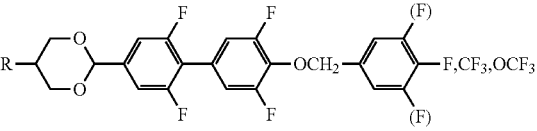
(LC3-0-39) 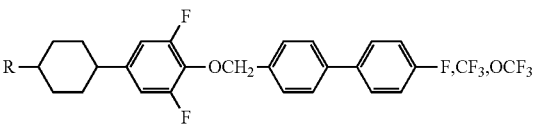
(LC3-0-40) 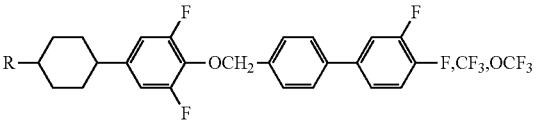
(LC3-0-41) 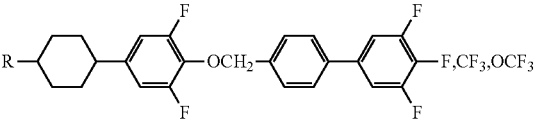
(LC3-0-42) 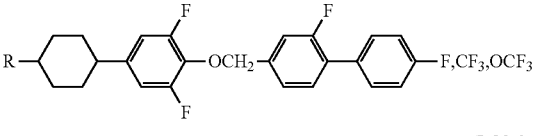
(LC3-0-43) 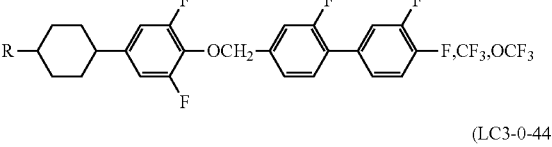
(LC3-0-44) 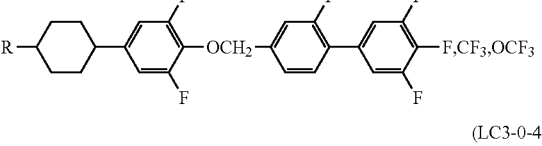
(LC3-0-45) 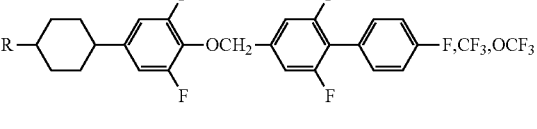

(LC3-0-46)
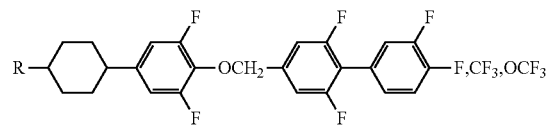
(LC3-0-47)
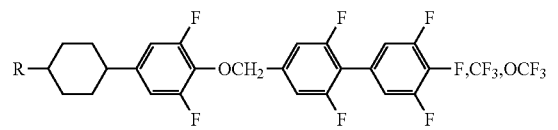
(LC3-0-48)
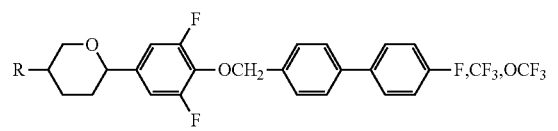
(LC3-0-49)
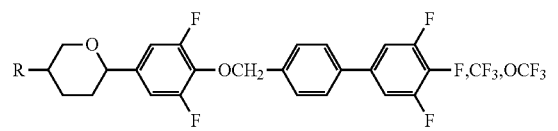
(LC3-0-50)
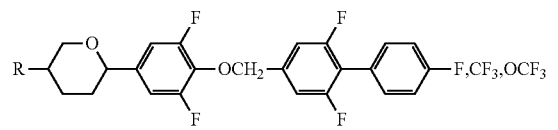
[Chem. 25]
(LC3-0-51)
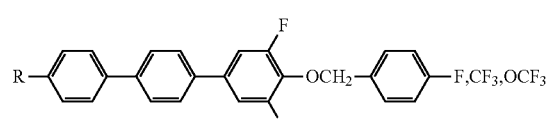
(LC3-0-52)
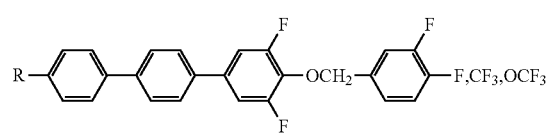
(LC3-0-53)
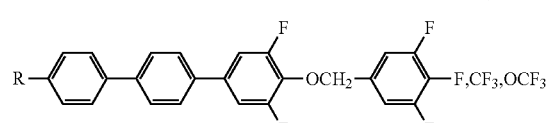
(LC3-0-54)
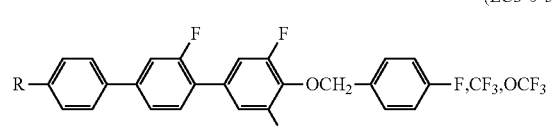
(LC3-0-55)
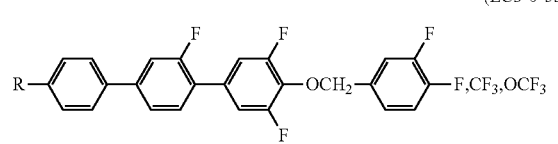
(LC3-0-56)
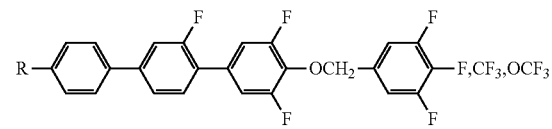
(LC3-0-57)
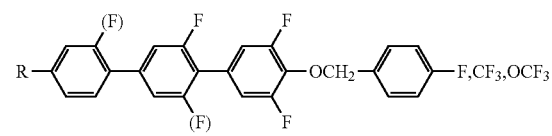
(LC3-0-58)
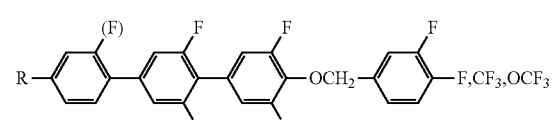
(LC3-0-59)
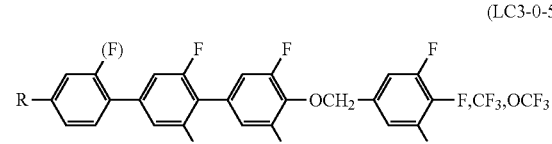
(LC3-0-60)
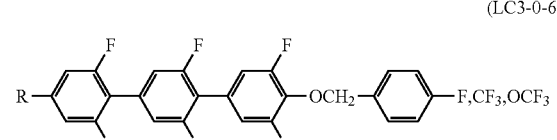
(LC3-0-61)
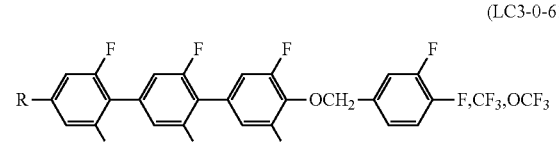
(LC3-0-62)
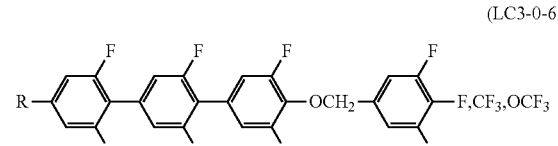
(LC3-0-63)
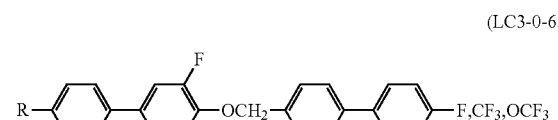
(LC3-0-64)
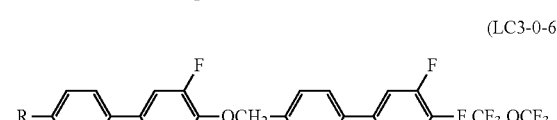
(LC3-0-65)

(LC3-0-66) ... (LC3-0-85)

[Chemical structure diagrams of compounds LC3-0-66 through LC3-0-85, each showing variations of fluorinated biphenyl/terphenyl structures with R group, OCH₂ linker, and terminal F, CF₃, OCF₃ groups]

(LC3-0-86)
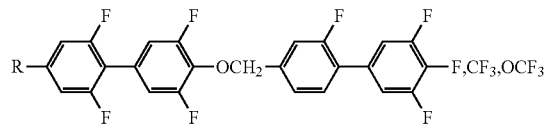

(LC3-0-87)
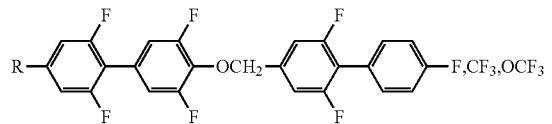

(LC3-0-88)
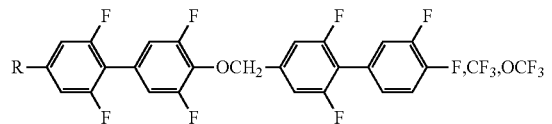

(LC3-0-89)
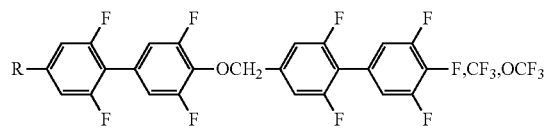

[Chem. 26]

(LC3-0-90)
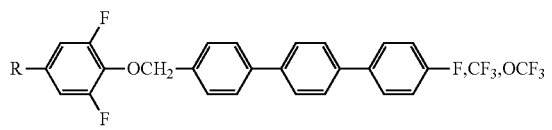

(LC3-0-91)
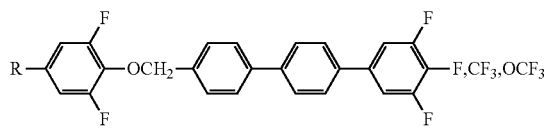

(LC3-0-92)
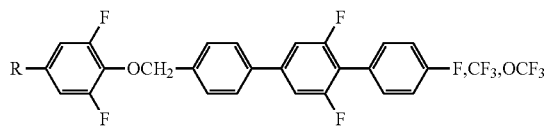

(LC3-0-93)
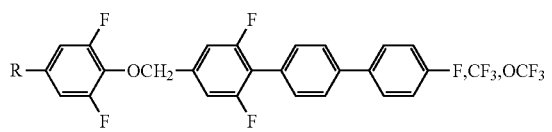

(LC3-0-94)
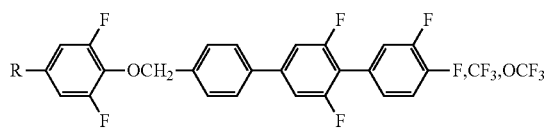

(LC3-0-95)
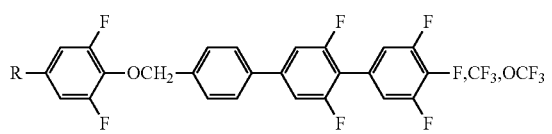

(LC3-0-96)
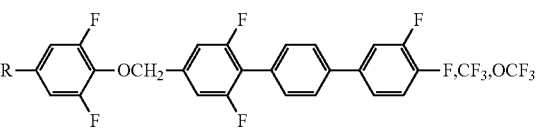

(LC3-0-97)
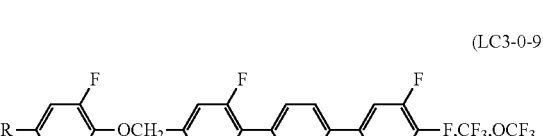

(In the formulas, R is as defined for $R^{31}$ in general formula (LC3); $X^{33}$, $X^{34}$, $X^{35}$, $X^{36}$, $X^{37}$, and $X^{38}$ are each independently H, Cl, F, $CF_3$, or $OCF_3$; $X^{32}$, $R^{31}$, and $R^{31}$ are an alkyl group of 1 to 15 carbon atoms, where at least one —$CH_2$— of the alkyl group is optionally replaced by —O—, —CH=CH—, —CO—, —OCO—, —COO—, —C≡C—, —$CF_2$O—, or —$OCF_2$— such that no oxygen atoms are directly adjacent to each other, and at least one hydrogen atom of the alkyl group is optionally replaced by halogen; $X^{32}$ is —H, —Cl, —F, —$CF_3$, or —$OCF_3$; $Y^{31}$ is —Cl, —F, —$CF_3$, —$OCF_3$, —$CF_2CF_3$, —$CHFCF_3$, —$OCF_2CF_3$, —$OCHFCF_3$, or —OCF=$CF_2$; and —F, $CF_3$, and $OCF_3$ are —F, —$CF_3$, or —$OCF_3$.)

The compound represented by general formula (LC4) is preferably a compound represented by any of general formulas (LC4-1) to (LC4-32).

[Chem. 27]

(LC-4-1)
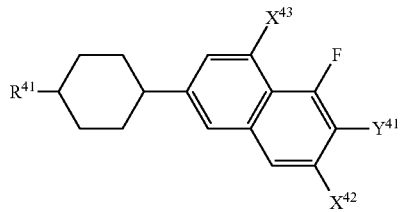

(LC-4-2)
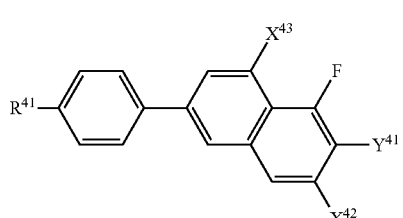

(LC-4-3)
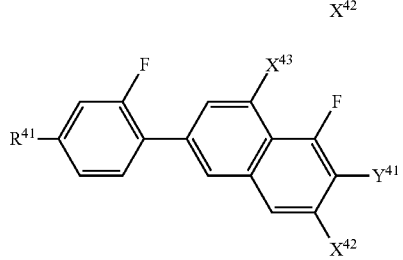

(LC-4-4)
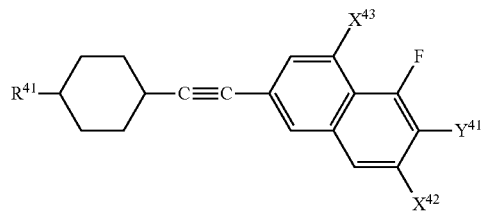
(LC-4-5)
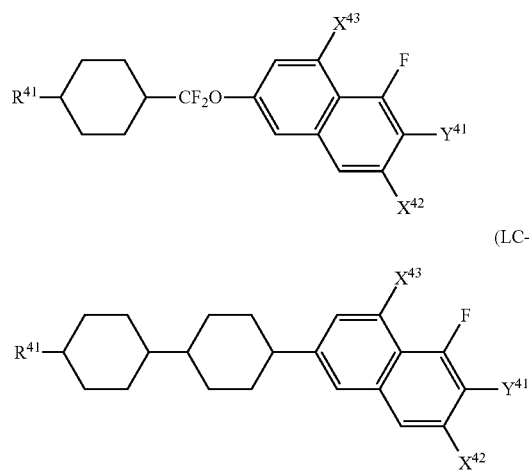
(LC-4-6)
(LC-4-7)
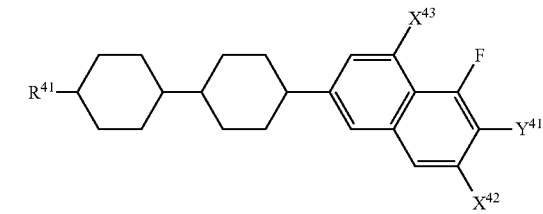
(LC-4-8)
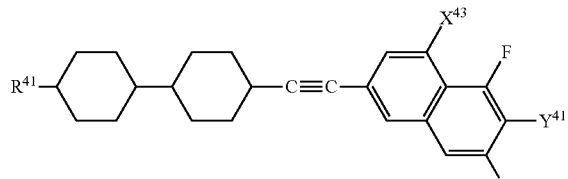
(LC-4-9)
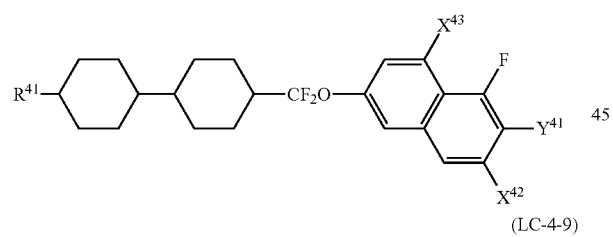
(LC-4-10)
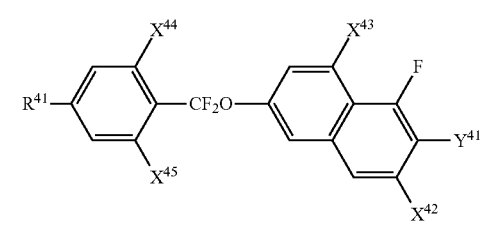
(LC-4-11)
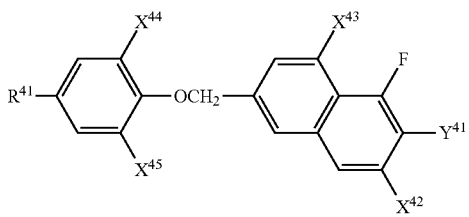
(LC-4-12)
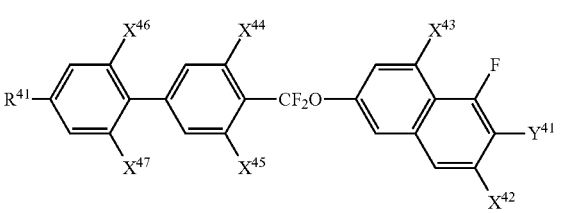
(LC-4-13)
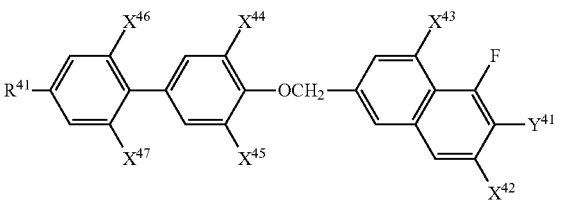
(LC-4-14)
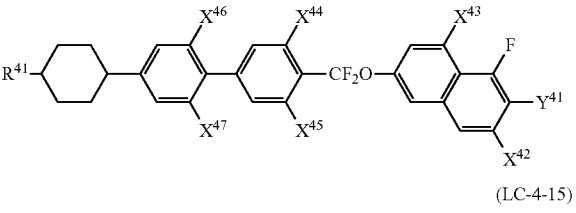
(LC-4-15)
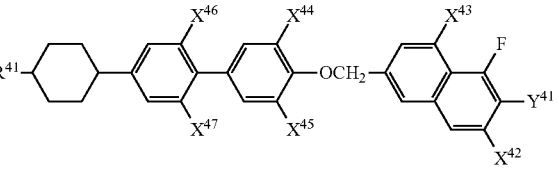
(LC-4-16)
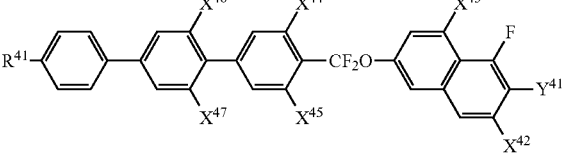
(LC-4-17)
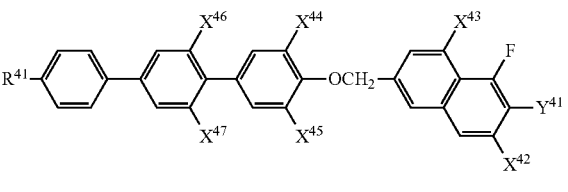

(LC-4-18) 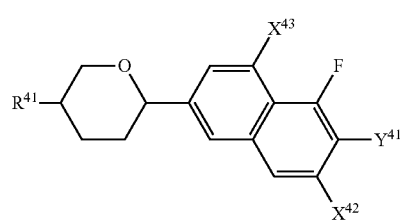
(LC-4-19) 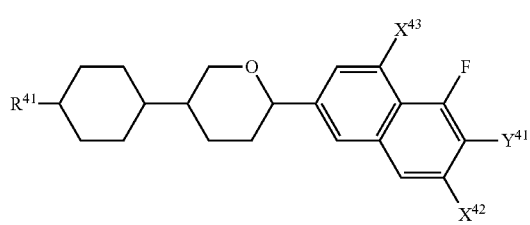
(LC-4-20) 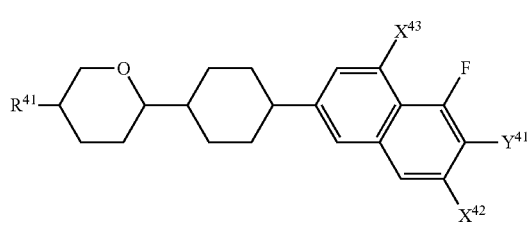
(LC-4-21) 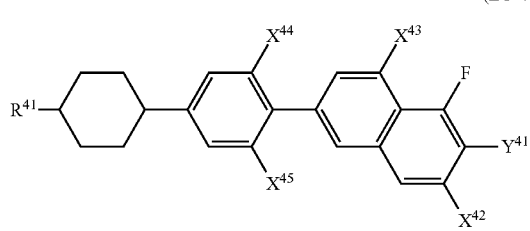
(LC-4-22) 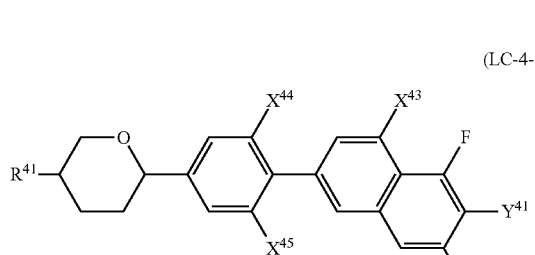
(LC-4-23) 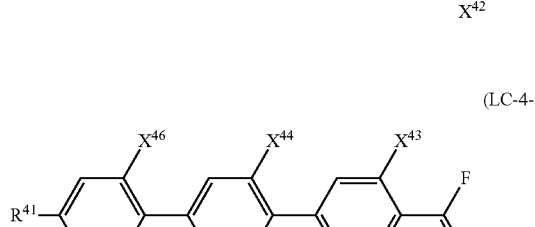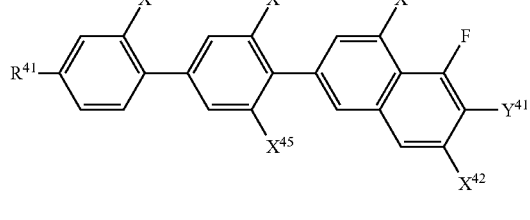
(LC-4-24) 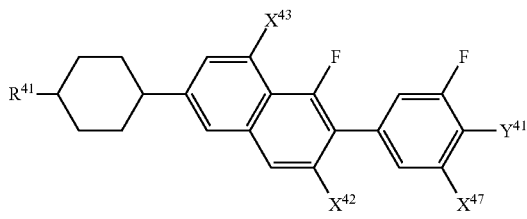
(LC-4-25) 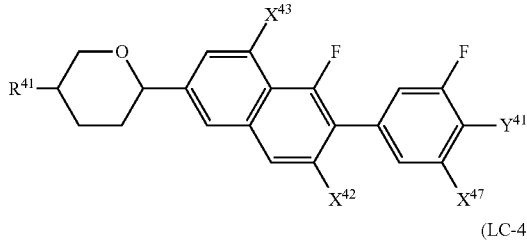
(LC-4-26) 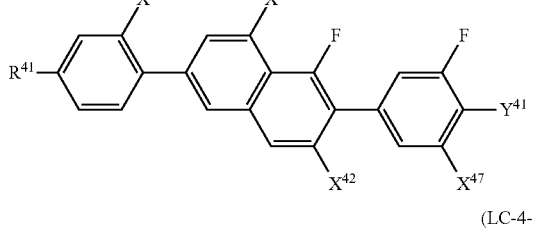
(LC-4-27) 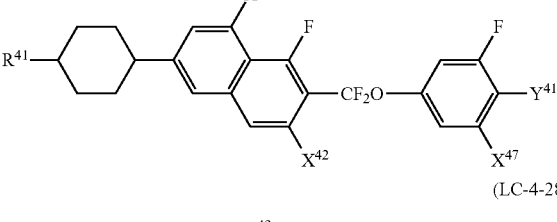
(LC-4-28) 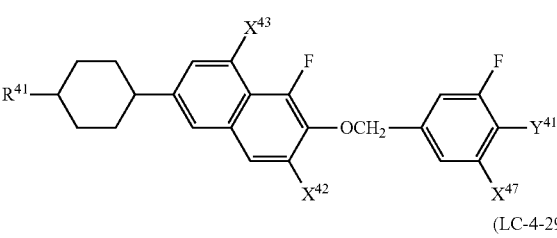
(LC-4-29) 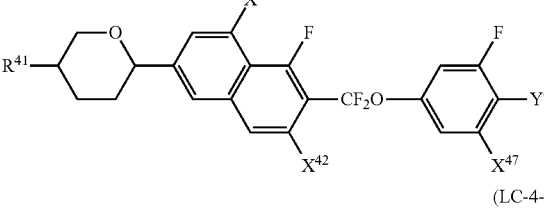
(LC-4-30) 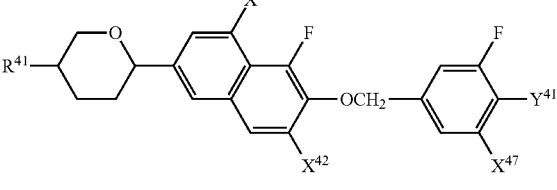

(LC-4-31)

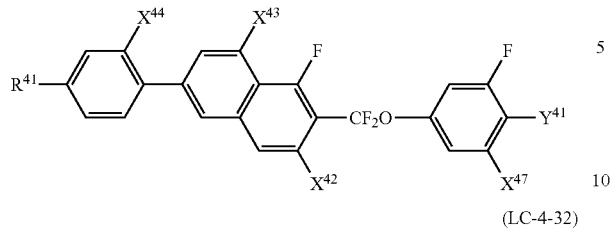

(LC-4-32)

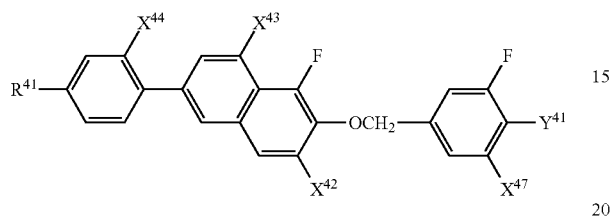

(In the formulas, $X^{44}$, $X^{45}$, $X^{46}$, and $X^{47}$ are each independently H, Cl, F, $CF_3$, or $OCF_3$; $R^{41}$ is an alkyl group of 1 to 15 carbon atoms, where at least one —$CH_2$— of the alkyl group is optionally replaced by —O—, —CH=CH—, —CO—, —OCO—, —COO—, —C≡C—, —$CF_2O$—, or —$OCF_2$— such that no oxygen atoms are directly adjacent to each other, and at least one hydrogen atom of the alkyl group is optionally replaced by halogen; $X^{42}$ and $X^{43}$ are each independently —H, —Cl, —F, —$CF_3$, or —$OCF_3$; and $Y^{41}$ is —Cl, —F, —$CF_3$, —$OCF_3$, —$CF_2CF_3$, —$CHFCF_3$, —$OCF_2CF_3$, —$OCHFCF_3$, or —$OCF=CF_2$.)

The compound represented by general formula (LC5) is preferably a compound represented by any of general formulas (LC5-1) to (LC5-26).

[Chem. 29]

(LC5-1)

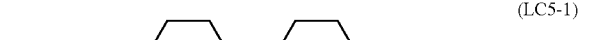

(LC5-2)

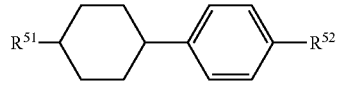

(LC5-3)

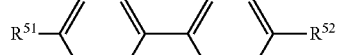

(LC5-4)

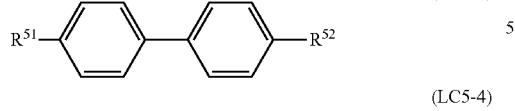

(LC5-5)

(LC5-6)

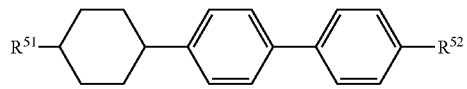

(LC5-7)

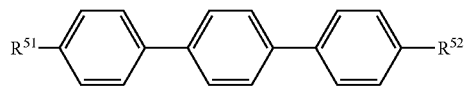

(LC5-8)

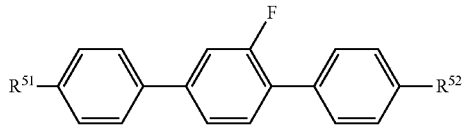

(LC5-9)

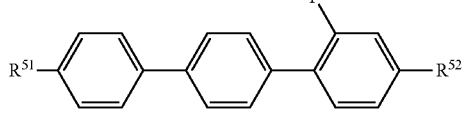

(LC5-10)

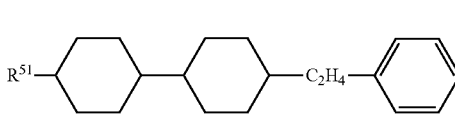

(LC5-11)

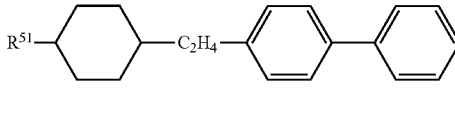

(LC5-12)

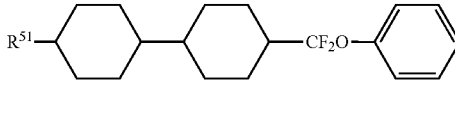

(LC5-13)

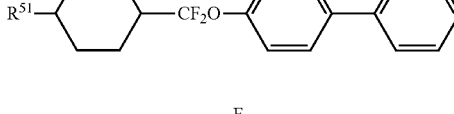

(LC5-14)

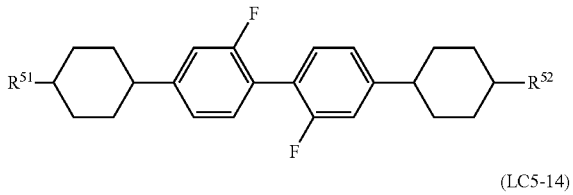

(LC5-15)

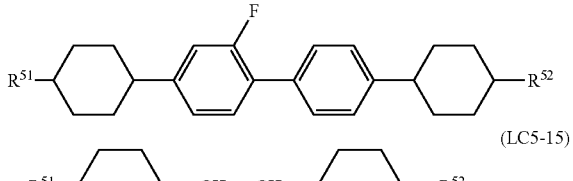

(LC5-16)

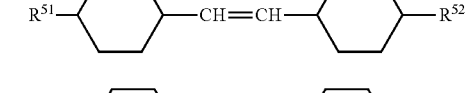

(LC5-17)

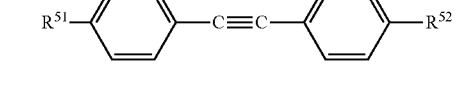

(LC5-18)

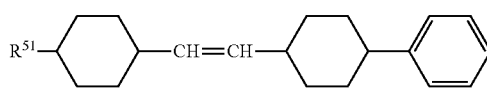

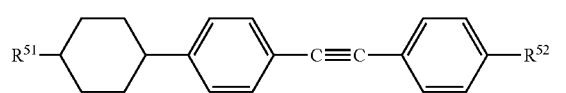

-continued (LC5-19)
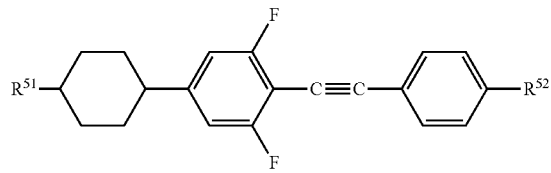

(LC5-20)
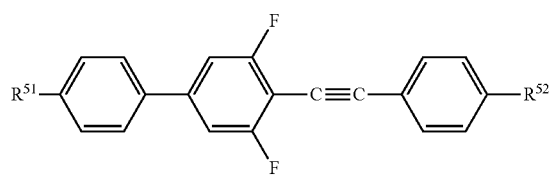

(LC5-21)
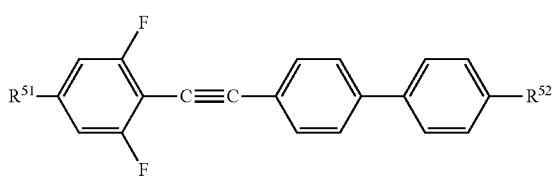

(LC5-22)
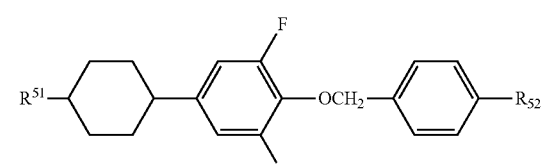

(LC5-23)
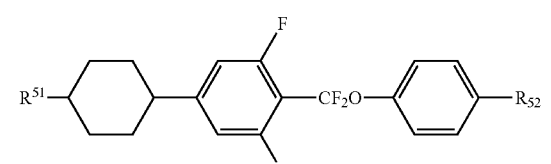

(LC5-24)
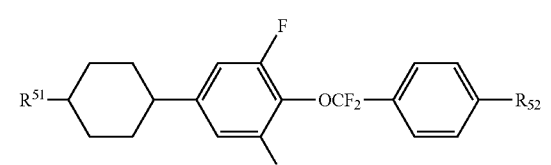

(LC5-25)
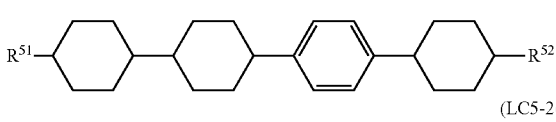

(LC5-26)
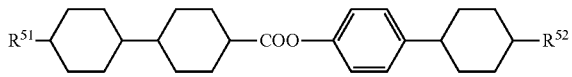

(In the formulas, $R^{51}$ and $R^{52}$ are each independently an alkyl group of 1 to 15 carbon atoms, where at least one —$CH_2$— of the alkyl group is optionally replaced by —O—, —CH=CH—, —CO—, —OCO—, —COO—, or —C≡C— such that no oxygen atoms are directly adjacent to each other.) Preferably, the liquid crystal composition according to the present invention contains at least one compound represented by general formula (LC5). The compound represented by general formula (LC5) is preferably present in an amount of 20% to 80% by mass, more preferably 30% to 70% by mass.

More preferably, the liquid crystal composition according to the present invention contains, as the compound represented by general formula (LC5), at least one compound selected from the group consisting of the following compounds in an amount of at most 70% by mass.

[Chem. 30]

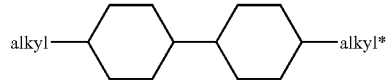
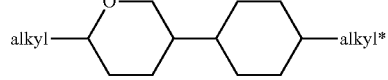
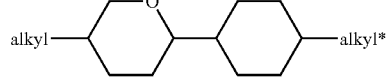
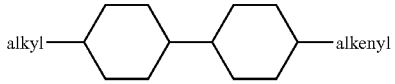
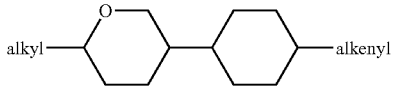
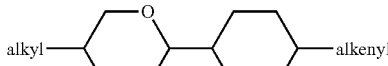
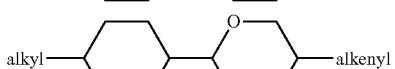
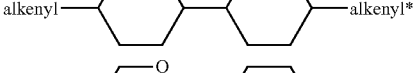
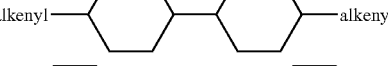
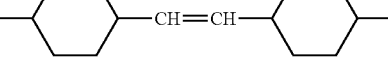
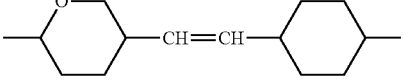
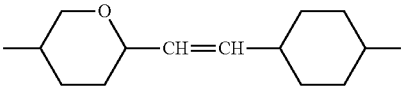
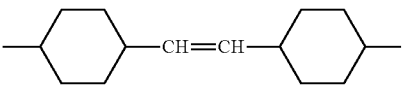

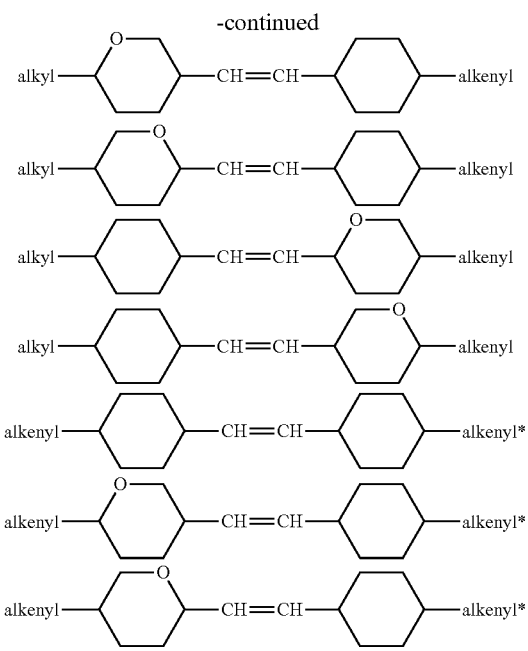

(In the formulas, alkyl and alkyl* are each independently an alkyl or alkoxy group of 1 to 5 carbon atoms; and alkenyl and alkenyl* are each independently an alkenyl or alkenyloxy group of 2 to 5 carbon atoms having the following formula.)

The liquid crystal composition according to the present invention preferably has a viscosity η of 20 mPa·s or less at 20° C.

The liquid crystal composition according to the present invention may contain at least one optically active compound. The optically active compound may be any optically active compound that allows liquid crystal molecules to be aligned in a twisted configuration. Since the twist generally varies depending on temperature, a plurality of optically active compounds may be used to achieve the desired temperature dependence. It is preferred to select and use optically active compounds having a strong twist effect to avoid a detrimental effect on properties such as the temperature range of the nematic liquid crystal phase and viscosity. As such optically active compounds, the liquid crystal composition according to the present invention preferably contains liquid crystals such as cholesteryl nonanoate and compounds represented by general formulas (Ch-1) to (Ch-6).

[Chem. 31]

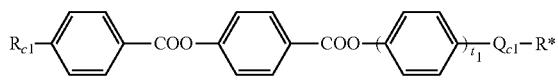
(Ch-1)

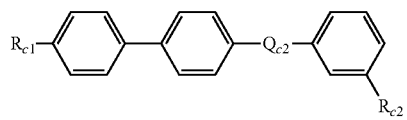
(Ch-2)

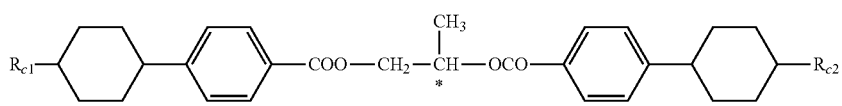
(Ch-3)

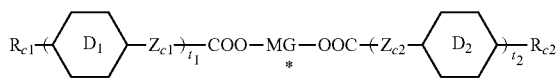
(Ch-4)

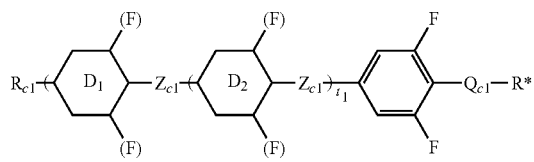
(Ch-5)

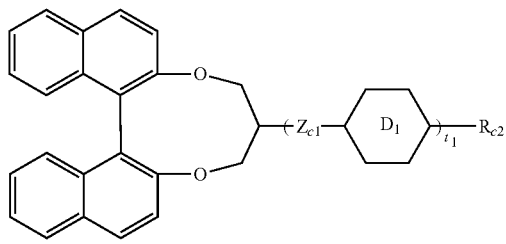
(Ch-6)

In the formulas, $R_{c1}$, $R_{c2}$, and R* are each independently an alkyl group of 1 to 15 carbon atoms, where at least one —$CH_2$— of the alkyl group is optionally replaced by —O—, —CH=CH—, —CO—, —OCO—, —COO—, —C≡C—, —$CF_2$O—, or —O$CF_2$— such that no oxygen atoms are directly adjacent to each other, and at least one hydrogen atom of the alkyl group is optionally replaced by halogen, with the proviso that R* has at least one optically active branched-chain group or halogen substituent. $Z_{c1}$ and $Z_{c2}$ are each independently a single bond, —CH=CH—, —C≡C—, —$CH_2CH_2$—, —$(CH_2)_4$—, —COO—, —OCO—, —$OCH_2$—, —$CH_2O$—, —$OCF_2$—, or —$CF_2O$—. $D_1$ and $D_2$ are a cyclohexane or benzene ring, where at least one —$CH_2$— of the cyclohexane ring is optionally replaced by —O— such that no oxygen atoms are directly adjacent to each other, at least one —$CH_2CH_2$— of the ring is optionally replaced by —CH=CH—, —$CF_2O$—, or —$OCF_2$—, at least one —CH= of the benzene ring is optionally replaced by —N= such that no nitrogen atoms are directly adjacent to each other, and at least one hydrogen atom of the ring is optionally replaced by F, Cl, or $CH_3$. $t_1$ and $t_2$ are 0, 1, 2, or 3. MG*, $Q_{c1}$, and $Q_{c2}$ are any of the following structures.

[Chem. 32]

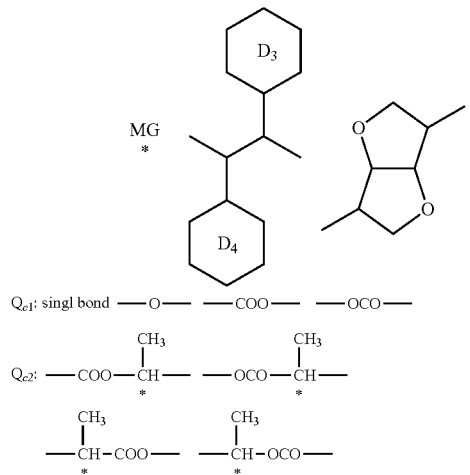

(In the formulas, $D_3$ and $D_4$ are a cyclohexane or benzene ring, where at least one —$CH_2$— of the cyclohexane ring is optionally replaced by —O— such that no oxygen atoms are directly adjacent to each other, at least one —$CH_2CH_2$— of the ring is optionally replaced by —CH=CH—, —$CF_2O$—, or —$OCF_2$—, at least one —CH= of the benzene ring is optionally replaced by —N= such that no nitrogen atoms are directly adjacent to each other, and at least one hydrogen atom of the ring is optionally replaced by F, Cl, or $CH_3$.)

The liquid crystal composition according to the present invention may contain at least one polymerizable compound. The polymerizable compound is preferably a discotic liquid crystal compound having a benzene derivative, triphenylene derivative, truxene derivative, phthalocyanine derivative, or cyclohexane derivative backbone in the center of the molecule and linear alkyl, linear alkoxy, or substituted benzoyloxy side chains extending radially from the backbone.

Specifically, the polymerizable compound is preferably a polymerizable compound represented by general formula (PC).

[Chem. 33]

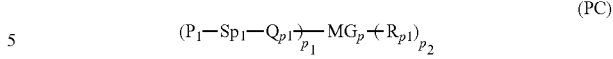

(In the formula, $P_1$ is a polymerizable functional group; $Sp_1$ is a spacer group of 0 to 20 carbon atoms; $Q_{p1}$ is a single bond, —O—, —NH—, —NHCOO—, —OCONH—, —CH=CH—, —CO—, —COO—, —OCO—, —OCOO—, —OOCO—, —CH=CH—, —CH=CH—COO—, —OCO—CH=CH—, or —C≡C—; $p_1$ and $p_2$ are each independently 1, 2, or 3; $MG_p$ is a mesogenic group or mesogenic supporting group; and $R_{p1}$ is halogen, cyano, or an alkyl group of 1 to 25 carbon atoms, where at least one $CH_2$ moiety of the alkyl group is optionally replaced by —O—, —S—, —NH—, —N($CH_3$)—, —CO—, —COO—, —OCO—, —OCOO—, —SCO—, —COS—, or —C≡C— such that no oxygen atoms are directly adjacent to each other, or $R_{p1}$ may be $P_2$—$S_{p2}$-$Q_{p2}$-, where $P_2$, $Sp_2$, and $Q_{p2}$ are each independently as defined for $P_1$, $Sp_1$, and $Q_{p1}$.)

More preferably, the polymerizable compound is a polymerizable compound of general formula (PC) where $MG_p$ is represented by the following structure.

[Chem. 34]

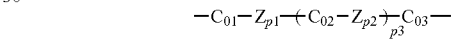

(In the formula, $C_{01}$ to $C_{03}$ are each independently 1,4-phenylene, 1,4-cyclohexylene, 1,4-cyclohexenyl, tetrahydropyran-2,5-diyl, 1,3-dioxane-2,5-diyl, tetrahydrothiopyran-2,5-diyl, 1,4-bicyclo(2,2,2)octylene, decahydronaphthalene-2,6-diyl, pyridine-2,5-diyl, pyrimidine-2,5-diyl, pyrazine-2,5-diyl, 1,2,3,4-tetrahydronaphthalene-2,6-diyl, 2,6-naphthylene, phenanthrene-2,7-diyl, 9,10-dihydrophenanthrene-2,7-diyl, 1,2,3,4,4a,9,10a-octahydrophenanthrene-2,7-diyl, or fluorene-2,7-diyl, where 1,4-phenylene, 1,2,3,4-tetrahydronaphthalene-2,6-diyl, 2,6-naphthylene, phenanthrene-2,7-diyl, 9,10-dihydrophenanthrene-2,7-diyl, 1,2,3,4,4a,9,10a-octahydrophenanthrene-2,7-diyl, and fluorene-2,7-diyl are optionally substituted by at least one F, Cl, $CF_3$, $OCF_3$, or cyano group, at least one alkyl, alkoxy, alkanoyl, or alkanoyloxy group of 1 to 8 carbon atoms, or at least one alkenyl, alkenyloxy, alkenoyl, or alkenoyloxy group of 2 to 8 carbon atoms; $Z_{p1}$ and $Z_{p2}$ are each independently —COO—, —OCO—, —$CH_2CH_2$—, —$OCH_2$—, —$CH_2O$—, —CH=CH—, —C≡C—, —CH=CHCOO—, —OCOCH=CH—, —$CH_2CH_2$COO—, —$CH_2CH_2$OCO—, —COO$CH_2CH_2$—, —OCO$CH_2CH_2$—, —CONH—, —NHCO—, or a single bond; and $p_3$ is 0, 1, or 2.)

If $Sp_1$ and $Sp_2$ are each independently an alkylene group, the alkylene group is optionally substituted by at least one halogen or CN group, where at least one $CH_2$ of that group is optionally replaced by —O—, —S—, —NH—, —N($CH_3$)—, —CO—, —COO—, —OCO—, —OCOO—, —SCO—, —COS—, or —C≡C— such that no oxygen atoms are directly adjacent to each other. $P_1$ and $P_2$ are preferably each independently any of the following general formulas.

[Chem. 35]

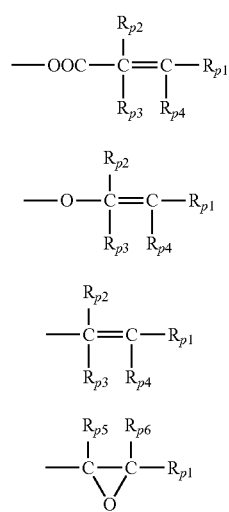

(PCO-a)
(PCO-b)
(PCO-c)
(PCO-d)

(In the formulas, $R_{p2}$ to $R_{p6}$ are each independently hydrogen, halogen, or an alkyl group of 1 to 5 carbon atoms.)

More specifically, the polymerizable compound of general formula (PC) is preferably a polymerizable compound represented by any of general formulas (PC0-1) to (PC0-6).

[Chem. 36]

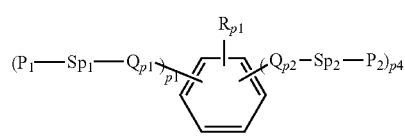 (PCO-1)

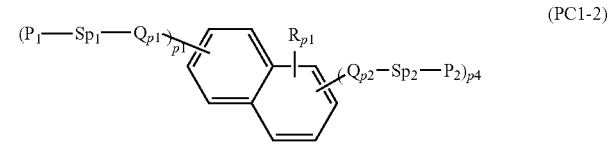 (PCO-2)

$P_1-Sp_1-Q_{p1}-MG_p-Q_{p2}-Sp_2-P_2$ (PCO-3)

$P_1-Q_{p1}-MG_p-Q_{p2}-P_2$ (PCO-4)

$P_1-Sp_1-Q_{p1}-MG_p-R_{p1}$ (PCO-5)

$P_1-Q_{p1}-MG_p-R_{p1}$ (PCO-6)

(In the formulas, $p_4$ are each independently 1, 2, or 3.)
Even more specifically, the polymerizable compound of general formula (PC) is preferably a polymerizable compound represented by any of general formulas (PC1-1) to (PC1-9).

[Chem. 37]

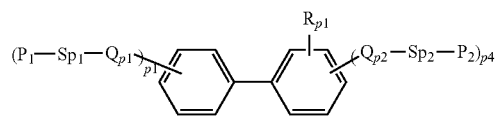 (PC1-1)

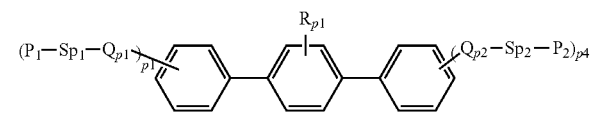 (PC1-2)

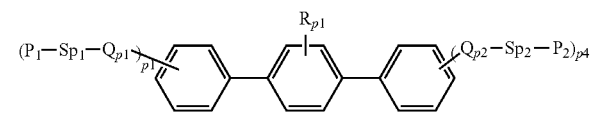 (PC1-3)

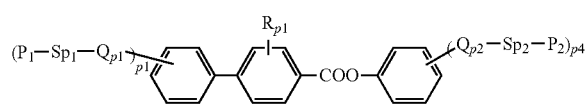 (PC1-4)

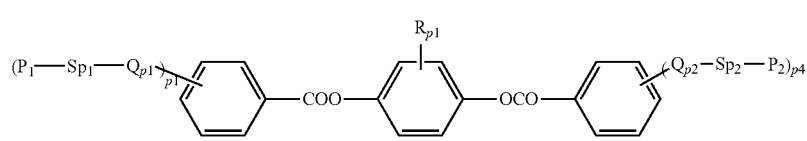 (PC1-5)

(PC1-6)

(PC1-7)

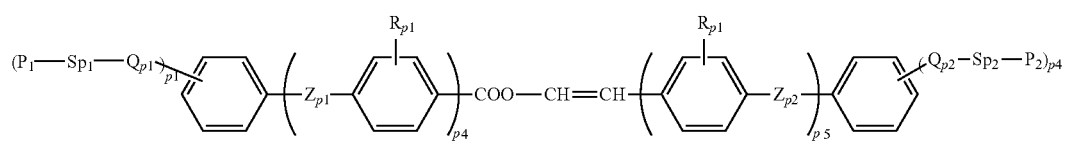 (PC1-8)

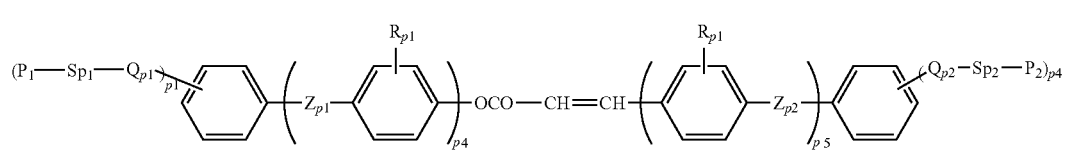 (PC1-9)

(In the formulas, $p_5$ is 0, 1, 2, 3, or 4.) In particular, $Sp_1$, $Sp_2$, $Q_{p1}$, and $Q_{p2}$ are preferably a single bond; $P_1$ and $P_2$ are preferably formula (PC0-a), more preferably acryloyloxy or methacryloyloxy; $p_1+p_4$ is preferably 2, 3, or 4; and $R_{p1}$ is preferably H, F, $CF_3$, $OCF_3$, $CH_3$, or $OCH_3$. More preferred are compounds represented by general formulas (PC1-2), (PC1-3), (PC1-4), and (PC1-8).

Also preferred are discotic liquid crystal compounds of general formula (PC) where $MG_p$ is represented by general formula (PC1)-9.

[Chem. 38]

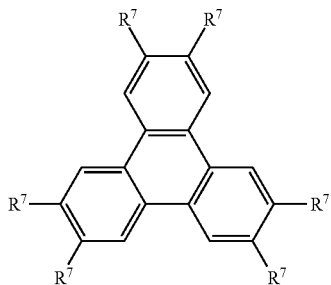

(PC1)-9

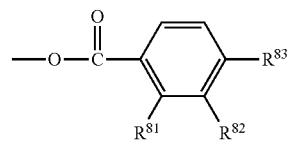

(PC1-e)

(In the formulas, $R_7$ is each independently $P_1$-$Sp_1$-$Q_{p1}$ or a substituent of general formula (PC1-e), where $R^{81}$ and $R^{82}$ are each independently hydrogen, halogen, or methyl, and $R_{83}$ is an alkoxy group of 1 to 20 carbon atoms, where at least one hydrogen atom of the alkoxy group is replaced by a substituent represented by any of general formulas (PC0-a) to (PC0-d) above.)

The polymerizable compound is preferably present in an amount of 0.05% to 2.0% by mass.

The polymerizable compound present in the liquid crystal composition according to the present invention is polymerized to fabricate a liquid crystal display device. In this process, it is desirable to reduce the content of the unpolymerized component to the desired level or lower. The liquid crystal composition preferably contains a compound of general formula (LC0) having a partial structure containing biphenyl and/or terphenyl. More specifically, compounds represented by general formulas (LC0-10) to (LC0-27), (LC0-48) to (LC0-53), and (LC0-60) to (LC0-68) are preferred, and at least one of them is preferably present in an amount of 0.1% to 40% by mass. It is also preferred to use a combination of compounds selected from the group consisting of polymerizable compounds represented by general formulas (PC1-1) to (PC1-3), (PC1-8), and (PC1-9).

The liquid crystal composition may further contain at least one antioxidant and may further contain at least one UV absorber. The antioxidant is preferably selected from those represented by general formulas (E-1) and (E-2).

[Chem. 39]

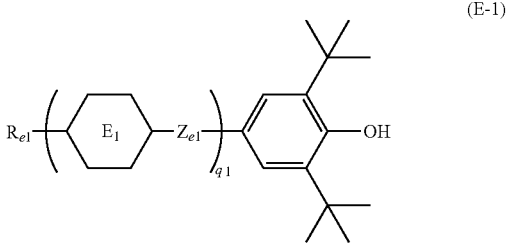

(E-1)

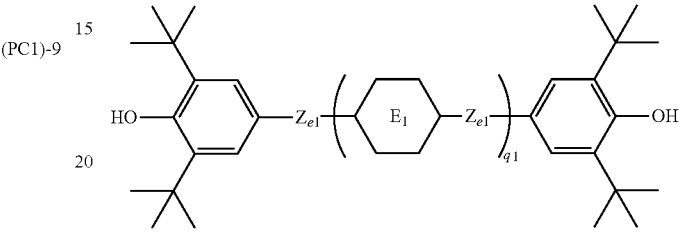

(E-2)

(In the formulas, $R_{e1}$ is an alkyl group of 1 to 15 carbon atoms, where at least one —$CH_2$— of the alkyl group is optionally replaced by —O—, —CH=CH—, —CO—, —OCO—, —COO—, —C≡C—, —$CF_2$O—, or —$OCF_2$— such that no oxygen atoms are directly adjacent to each other, and at least one hydrogen atom of the alkyl group is optionally replaced by halogen;

$Z_{e1}$ and $Z_{e2}$ are each independently a single bond, —CH=CH—, —C≡C—, —$CH_2CH_2$—, —$(CH_2)_4$—, —COO—, —OCO—, —$OCH_2$—, —$CH_2O$—, —$OCF_2$—, or —$CF_2O$—;

$E_1$ is a cyclohexane or benzene ring, where at least one —$CH_2$— of the cyclohexane ring is optionally replaced by —O— such that no oxygen atoms are directly adjacent to each other, at least one —$CH_2CH_2$— of the ring is optionally replaced by —CH=CH—, —$CF_2O$—, or —$OCF_2$—, at least one —CH= of the benzene ring is optionally replaced by —N= such that no nitrogen atoms are directly adjacent to each other, and at least one hydrogen atom of the ring is optionally replaced by F, Cl, or $CH_3$; and $q_1$ is 0, 1, 2, or 3.)

The liquid crystal composition according to the present invention can be used for liquid crystal display devices, particularly active-matrix liquid crystal display devices such as TN, OCB, ECB, IPS, and VA-IPS liquid crystal display devices (including those with FFS electrodes). VA-IPS is a mode in which a liquid crystal material of positive dielectric anisotropy (Δε>0) is aligned perpendicular to a substrate surface when no voltage is applied and liquid crystal molecules are driven by pixel electrodes and a common electrode disposed on the same substrate surface. This mode, in which liquid crystal molecules are aligned along a curved electric field generated by the pixel electrodes and the common electrode, facilitates pixel division and the formation of multiple domains and also provides the advantage of quick response. This mode is known under various names, such as EOC and VA-IPS, as disclosed in the following non-patent literature: Proc. 13th IDW, 97 (1997), Proc. 13th IDW, 175 (1997), SID Sym. Digest, 319 (1998), SID Sym. Digest, 838 (1998), SID Sym. Digest, 1085 (1998), SID Sym. Digest, 334 (2000), and Eurodisplay Proc., 142 (2009). In the present invention, this mode is hereinafter abbreviated as "VA-IPS".

In general, the threshold voltage (Vc) of Fréedericksz transition in TN and ECB is given by the following equation.

$$V_C = \frac{\Pi d_{cell}}{d_{cell} + \langle r1 \rangle} \sqrt{\frac{K11}{\Delta\varepsilon}} \quad \text{[Math. 1]}$$

The threshold voltage (Vc) of Fréedericksz transition in IPS is given by the following equation.

$$V_C = \frac{\Pi d_{gap}}{d_{cell} + \langle r2 \rangle} \sqrt{\frac{K22}{\Delta\varepsilon}} \quad \text{[Math. 2]}$$

The threshold voltage (Vc) of Fréedericksz transition in VA is given by the following equation.

$$V_C = \frac{\Pi d_{cell}}{d_{cell} - \langle r3 \rangle} \sqrt{\frac{K33}{|\Delta\varepsilon|}} \quad \text{[Math. 3]}$$

(In the equations, Vc is the Fréedericksz transition (V); Π is the circular constant; $d_{cell}$ is the distance (μm) between first and second substrates; $d_{gap}$ is the distance (μm) between pixel electrodes and a common electrode; $d_{ITO}$ is the width (μm) of the pixel electrodes and/or the common electrode; <r1>, <r2>, and <r3> are extrapolation lengths (μm); K11 is the splay elastic constant (N); K22 is the twist elastic constant (N); K33 is the bend elastic constant (N); and Δε is the dielectric anisotropy.)

The inventors have found that Math. 4 below applies to VA-IPS.

$$V_C \propto \frac{d_{gap} - \langle r' \rangle}{d_{ITO} + \langle r \rangle} \frac{\Pi d_{cell}}{d_{cell} - \langle r3 \rangle} \sqrt{\frac{K33}{|\Delta\varepsilon|}} \quad \text{[Math. 4]}$$

(In the equation, Vc is the Fréedericksz transition (V); Π is the circular constant; $d_{cell}$ is the distance (μm) between first and second substrates; $d_{gap}$ is the distance (μm) between pixel electrodes and a common electrode; $d_{ITO}$ is the width (μm) of the pixel electrodes and/or the common electrode; <r>, <r'>, and <r3> are extrapolation lengths (μm); K33 is the bend elastic constant (N); and Δε is the dielectric anisotropy.) Math. 4 suggests that a cell configuration having a smaller $d_{gap}$ and a larger $d_{ITO}$ allows for a lower driving voltage and that a liquid crystal composition having a Δε larger in absolute value and a smaller K33 allows for a lower driving voltage.

A liquid crystal display device can be fabricated using the liquid crystal composition according to the present invention by aligning liquid crystal molecules along a substrate surface by rubbing using compounds such as polyimides and polyamides. A liquid crystal display device can also be fabricated by photoalignment using compounds such as chalcones, cinnamates, and cinnamoyl compounds. A new alignment technique that can be used involves incorporating a polymerizable liquid crystal compound into an alignment layer and polymerizing the polymerizable liquid crystal compound.

The properties, such as Δε, K11, and K33, of the liquid crystal composition according to the present invention can be adjusted to the preferred levels.

The product (Δn·d) of the refractive index anisotropy (Δn) of a liquid crystal composition and the distance (d) between first and second substrates of a display is closely related to viewing angle characteristics and response speed. The distance (d) therefore tends to become smaller, i.e., 3 to 4 μm. The product (Δn·d) is preferably 0.31 to 0.33 for TN, ECB, and IPS (in which liquid crystal molecules are aligned substantially parallel to a substrate surface when no voltage is applied). For VA-IPS, in which liquid crystal molecules are aligned perpendicular to both substrates, the product (Δn·d) is preferably 0.20 to 0.59, more preferably 0.30 to 0.40. The appropriate product (Δn·d) thus depends on the mode of the specific display device. The refractive index anisotropy (Δn) of liquid crystal compositions suitable for various modes ranges from 0.070 to 0.110, from 0.100 to 0.140, or from 0.130 to 0.180. Liquid crystal compositions having refractive index anisotropies (Δn) within such different ranges can be prepared.

A liquid crystal composition according to the present invention containing a polymerizable compound represented by general formula (PC) can be used to provide a polymer-stabilized TN, OCB, ECB, IPS, or VA-IPS liquid crystal display device by polymerizing the polymerizable compound present in the liquid crystal composition with or without the application of voltage. Specifically, a liquid crystal display device can be fabricated by placing the liquid crystal composition containing the polymerizable compound between two substrates and polymerizing the polymerizable compound present in the liquid crystal composition by means of energy such as UV radiation with or without the application of voltage. The polymerization of the polymerizable compound in the liquid crystal display device allows the alignment of liquid crystal molecules to be memorized, thereby improving the stability of the alignment. This also contributes to improved response speed.

EXAMPLES

The present invention is further illustrated by the following examples, although these examples are not intended to limit the present invention. In the compositions of the following Examples and Comparative Example, percentages are by mass.

The physical properties of liquid crystal compositions are denoted as follows:

$T_{N-I}$: nematic phase-isotropic liquid phase transition temperature (° C.)

T-n: lower temperature limit of nematic phase (° C.)

$\varepsilon\perp$: dielectric constant in direction perpendicular to long molecular axis at 25° C.

Δε: dielectric anisotropy at 25° C.

$n_o$: ordinary refractive index at 25° C.

Δn: refractive index anisotropy at 25° C.

Vth: applied voltage (V) in 6 μm thick cell that exhibits change in transmittance of 10% at 25° C. upon application of rectangular wave at frequency of 1 KHz $\eta_{20}$: bulk viscosity at 20° C. (mPa·s)

$\gamma_1$: rotational viscosity (mPa·s)

Compounds are represented by the following abbreviations.

TABLE 1

| | | | | | |
|---|---|---|---|---|---|
| n | $C_nH_{2n+1}$— | -2- | —$CH_2CH_2$— | —F | —F |
| m | —$C_mH_{2m+1}$ | -d- | —CH=CH— | —Cl | —Cl |
| nO | $C_nH_{2n+1}$O— | -T- | —C≡C— | —CN | —C≡N |
| Om | —O$C_mH_{2m+1}$ | -1O- | —$CH_2$O— | —CFFF | —$CF_3$ |
| ndm- | $C_nH_{2n+1}$—CH=CH—$(CH_2)_{m-1}$— | -O1- | —O$CH_2$— | —CFF | —$CHF_2$ |
| -ndm | —$(CH_2)_{n-1}$—CH=CH—$C_mH_{2m+1}$ | -CFFO- | —$CF_2$O— | —OCFFF | —$OCF_3$ |
| ndmO- | $C_nH_{2n+1}$—CH=CH—$(CH_2)_{m-1}$—O— | -OCFF- | —O$CF_2$— | —OCFF | —$OCHF_2$ |
| -Ondm | —O—$(CH_2)_{n-1}$—CH=CH—$C_mH_{2m+1}$ | -V- | —CO— | —OCFFCFFF | —$OCF2CF_3$ |
| | | -VO- | —COO— | —CFFCFFF | —$CF2CF_3$ |
| | | -OV- | —OCO— | —OCF=CFF | —OCF=$CF_2$ |
| | | | | —OCH=CFF | —OCH=$CF_2$ |

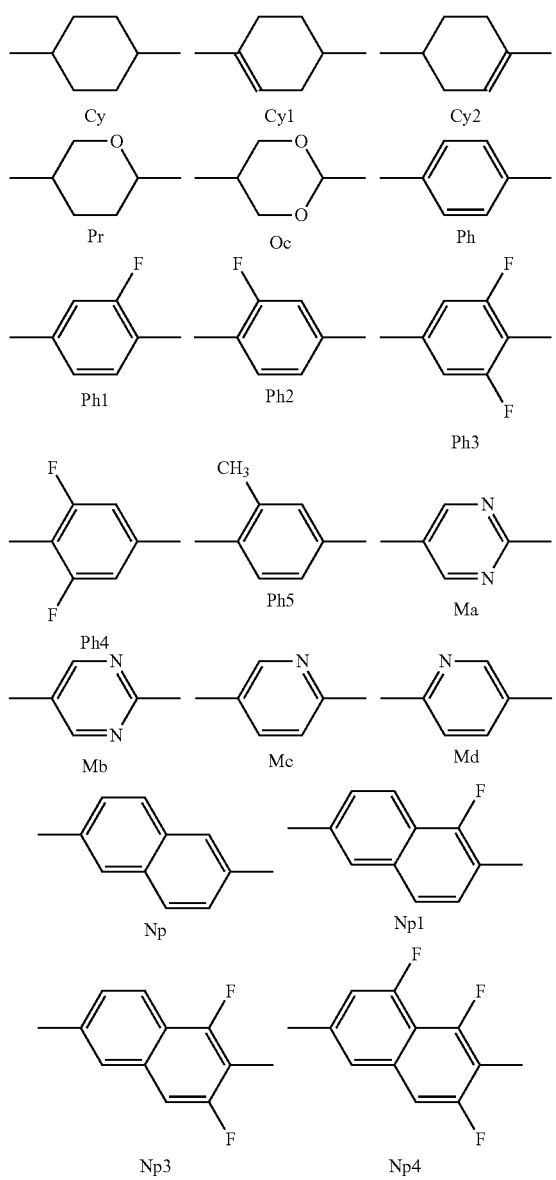

[Chem. 40]

(Example 1) (Comparative Example 1)

The resulting liquid crystal compositions and the physical properties thereof are shown below.

TABLE 2

| Component | Ex-1 | Ref-1 |
|---|---|---|
| 3-Ph3-O1-Cy-Ph-OCFFF | 10.0 | |
| 3-Ph3-O1-Cy-Ph3-F | 15.0 | |
| 3-Ph3-OCFF-Cy-Ph3-F | 5.0 | |
| 3-Ph-O1-Cy-Ph-OCFFF | | 10.0 |
| 3-Ph3-1O-Cy-Ph3-F | | 15.0 |
| 3-Ph-OCFF-Cy-Ph3-F | | 5.0 |
| 1d1-Cy-Cy-2 | 10.0 | 10.0 |
| 0d3-Cy-Cy-3 | 15.0 | 15.0 |
| 2-Cy-Cy-Ph-1 | 8.0 | 8.0 |
| 3-Cy-Cy-Ph-1 | 7.0 | 7.0 |
| 3-Cy-Ph1-Ph3-CFFO-Ph3-F | 5.0 | 5.0 |
| 3-Ph-Ph-Ph3-CFFO-Ph3-F | 5.0 | 5.0 |
| 3-Cy-Cy-Ph3-OCFFF | 5.0 | 5.0 |
| 5-Cy-Cy-Ph3-OCFFF | 5.0 | 5.0 |
| 2-Cy-Cy-Ph3-Ph3-F | 4.0 | 4.0 |
| 3-Cy-Cy-Ph3-Ph3-F | 3.0 | 3.0 |
| 5-Cy-Cy-Ph3-Ph3-F | 3.0 | 3.0 |
| total | 100.0 | 100.0 |
| Tni (° C.) | 73.7 | 71.4 |
| T-n (° C.) | −38.0 | −36.0 |
| Vth (volt) | 1.39 | 1.38 |
| Δε | 10.0 | 9.8 |
| Δn | 0.087 | 0.088 |
| η20° C. (mPa·s) | 14.5 | 20.3 |

Ex-1 is a liquid crystal composition containing compounds represented by general formula (LC0) in the present invention. Ref-1 is a liquid crystal composition containing no compound represented by general formula (LC0) in the present invention. The $γ_1$ of Ex-1 was 74 mPa·s, whereas the $γ_1$ of Ref-1 was 96 mPa·s. The results show that Ex-1 had a much lower viscosity than Ref-1, which contained compounds differing in partial structure from compounds represented by general formula (LC0), demonstrating the superiority of the combination according to the present invention.

Example 2

Liquid crystal compositions containing compounds of general formula (LC5) and the physical properties thereof are shown below.

TABLE 3

| Conponent | Mix-A | Mix-B |
|---|---|---|
| 0d1-Cy-Cy-3 | 10.0 | 10.0 |
| od1-Cy-Cy-1d1 | 10.0 | 20.0 |
| 3-Cy-d-Cy-1d1 | 10.0 | 20.0 |
| 3-Pr-Cy-2 | 10.0 | |
| 3-Pr-Cy-1d1 | 10.0 | 20.0 |

TABLE 3-continued

| Conponent | Mix-A | Mix-B |
|---|---|---|
| 3-Pr-d-Cy-3d0 | 10.0 | 20.0 |
| 5-Ph-Ph-1 | 10.0 | |
| 3-Cy-Cy-Ph-1 | 15.0 | 10.0 |
| 1-Ph-Ph1-Ph-3d0 | 15.0 | |
| total | 100.0 | 100.0 |
| Tni (° C.) | 78.9 | 78.0 |
| Δε | 0.1 | 0.1 |
| Δn | 0.104 | 0.063 |
| η20° C. (mPa · s) | 9.3 | 7.1 |

Liquid crystal compositions prepared using Mix-A and Mix-B and the physical properties thereof are shown below.

TABLE 4

| Mix-A | 35.0 |
|---|---|
| 3-Cy-Cy-Ph3-OCFFF | 5.0 |
| 3-Pr-Ph1-Ph3-CFFO-Ph3-F | 5.0 |
| 3-Ph3-O1-Cy-Ph-OCFFF | 7.0 |
| 3-Ph3-OCFF-Cy-Ph3-OCFFF | 8.0 |
| 3-Ph3-OCFF-Pr-Ph3-F | 5.0 |
| 3-Ph3-OCFF-Cy-Ph3-Ph3-OCFFF | 8.0 |
| 3-Ph-Ph3-OCFF-Cy-Ph3-F | 8.0 |
| 3-Pr-Ph3-O1-Cy-Ph3-F | 7.0 |
| 3-Ph3-OCFF-Cy-Pr-Ph3-F | 7.0 |
| 3-Ph3-OCFF-Cy-Ph1-Ph3-CFFO-Ph3-F | 5.0 |
| total | 100.0 |
| Tni (° C.) | 89.7 |
| T-n (° C.) | −43.0 |
| Vth (volt) | 1.09 |
| Δε | 14.8 |
| Δn | 0.108 |
| η20° C. (mPa · s) | 15.4 |

Example 3

The resulting liquid crystal composition and the physical properties thereof are shown below.

TABLE 5

| Mix-A | 50.0 |
|---|---|
| 3-Ph3-O1-Cy-Ph-OCFFF | 10.0 |
| 3-Ph3-O1-Cy-Ph3-Ph3-F | 5.0 |
| 3-Ph3-OCFF-Cy-Ph3-Ph3-F | 5.0 |
| 3-Ph3-OCFF-Cy-Ph3-CFFO-Ph3-F | 5.0 |
| 3-Ph3-OCFF-Pr-Ph3-CFFO-Ph3-F | 5.0 |
| 3-Ph3-OCFF-Cy-Ph3-Ph3-OCFFF | 5.0 |
| 3-Pr-Ph3-OCFF-Cy-Ph3-F | 5.0 |
| 3-Pr-Ph3-O1-Cy-Ph3-F | 5.0 |
| 3-Ph3-O1-Cy-Np3-F | 5.0 |
| total | 100.0 |
| Tni (° C.) | 74.0 |
| T-n (° C.) | −42.0 |
| Vth (volt) | 1.15 |
| Δε | 13.2 |
| Δn | 0.102 |
| η20° C. (mPa · s) | 15.5 |

Example 4

The resulting liquid crystal composition and the physical properties thereof are shown below.

TABLE 6

| Mix-A | 45.0 |
|---|---|
| 3-Ph-Ph1-Ph3-F | 5.0 |
| 3-Pr-Ph1-Ph3-CFFO-Ph3-F | 5.0 |
| 3-Ph3-OCFF-Cy-Ph3-OCFFF | 5.0 |
| 3-Ph3-O1-Cy-Ph3-Ph3-F | 7.0 |
| 3-Ph3-OCFF-Cy-Ph3-Ph3-F | 8.0 |
| 3-Ph3-OCFF-Cy-Ph3-CFFO-Ph3-F | 5.0 |
| 3-Ph3-OCFF-Pr-Ph3-CFFO-Ph3-F | 5.0 |
| 3-Ph3-OCFF-Cy-Ph3-Ph3-OCFFF | 5.0 |
| 3-Ph-Ph3-OCFF-Cy-Ph3-F | 5.0 |
| 3-Pr-Ph3-OCFF-Cy-Ph3-F | 5.0 |
| total | 100.0 |
| Tni (° C.) | 79.8 |
| T-n (° C.) | −41.0 |
| Vth (volt) | 1.04 |
| Δε | 17.1 |
| Δn | 0.110 |
| η20° C. (mPa · s) | 18.4 |

Example 5

The resulting liquid crystal composition and the physical properties thereof are shown below.

TABLE 7

| Mix-A | 55.0 |
|---|---|
| 3-Cy-Cy-CFFO-Ph3-F | 10.0 |
| 3-Cy-Pr-Ph3-F | 10.0 |
| 3-Ph3-OCFF-Cy-Ph3-OCFFF | 10.0 |
| 3-Ph3-OCFF-Pr-Ph3-F | 10.0 |
| 3-Ph3-OCFF-Cy-Ph1-Ph3-CFFO-Ph3-F | 5.0 |
| total | 100.0 |
| Tni (° C.) | 75.0 |
| T-n (° C.) | −39.0 |
| Vth (volt) | 1.62 |
| Δε | 7.7 |
| Δn | 0.102 |
| η20° C. (mPa · s) | 10.8 |

Example 6

The resulting liquid crystal composition and the physical properties thereof are shown below.

TABLE 8

| Mix-A | 45.0 |
|---|---|
| 3-Cy-Ph1-Ph3-CFFO-Ph3-F | 5.0 |
| 3-Cy-Ph-Ph3-F | 5.0 |
| 3-Ph-Ph1-Ph3-F | 5.0 |
| 3-Pr-Ph-Ph3-F | 5.0 |
| 3-Pr-Ph1-Ph3-CFFO-Ph3-F | 5.0 |
| 3-Ph3-OCFF-Cy-Ph3-OCFFF | 5.0 |
| 3-Ph3-OCFF-Cy-Ph3-Ph3-OCFFF | 5.0 |
| 3-Ph-Ph3-OCFF-Cy-Ph3-F | 5.0 |
| 3-Ph3-OCFF-Cy-Pr-Ph3-F | 5.0 |
| 3-Ph3-O1-Cy-Np3-F | 5.0 |
| 3-Ph3-OCFF-Cy-Ph1-Ph3-CFFO-Ph3-F | 5.0 |
| total | 100.0 |
| Tni (° C.) | 86.5 |
| T-n (° C.) | −47.0 |
| Vth (volt) | 1.13 |
| Δε | 13.4 |
| Δn | 0.125 |
| η20° C. (mPa · s) | 19.1 |

Example 7

The resulting liquid crystal composition and the physical properties thereof are shown below.

TABLE 9

| | |
|---|---|
| Mix-B | 40.0 |
| 3-Cy-Cy-CFFO-Ph3-F | 10.0 |
| 3-Cy-Ph1-Ph3-CFFO-Ph3-F | 5.0 |
| 3-Cy-Ph-Ph3-F | 5.0 |
| 3-Cy-Cy-Ph3-OCFFF | 5.0 |
| 3-Cy-Pr-Ph3-F | 10.0 |
| 3-Pr-Ph-Ph3-F | 5.0 |
| 3-Pr-Cy-CFFO-Ph3-F | 5.0 |
| 5-Pr-Oc-Ph3-CFFO-Ph3-F | 5.0 |
| 3-Pr-Ph3-O1-Cy-Ph3-F | 5.0 |
| 3-Ph3-OCFF-Cy-Pr-Ph3-F | 5.0 |
| total | 100.0 |
| Tni (° C.) | 81.2 |
| T-n (° C.) | −41.0 |
| Vth (volt) | 1.44 |
| Δε | 9.8 |
| Δn | 0.078 |
| η20° C. (mPa · s) | 17.8 |

Example 8

The resulting liquid crystal composition and the physical properties thereof are shown below.

TABLE 10

| | |
|---|---|
| Mix-B | 45.0 |
| 3-Cy-Cy-CFFO-Ph3-F | 10.0 |
| 3-Cy-Pr-Ph3-F | 10.0 |
| 3-Pr-Cy-CFFO-Ph3-F | 10.0 |
| 3-Ph3-O1-Cy-Ph-OCFFF | 5.0 |
| 3-Pr-Ph3-OCFF-Cy-Ph3-F | 10.0 |
| 3-Pr-Ph3-O1-Cy-Ph3-F | 10.0 |
| total | 100.0 |
| Tni (° C.) | 80.9 |
| T-n (° C.) | −39.0 |
| Vth (volt) | 1.61 |
| Δε | 8.0 |
| Δn | 0.067 |
| η20° C. (mPa · s) | 13.7 |

Example 9

The resulting liquid crystal composition and the physical properties thereof are shown below.

TABLE 11

| | |
|---|---|
| Mix-B | 50.0 |
| 3-Ph3—O1-Cy-Ph—OCFFF | 5.0 |
| 3-Ph3—OCFF-Cy-Ph3—OCFFF | 10.0 |
| 3-Ph3—OCFF—Pr—Ph3—F | 5.0 |
| 3-Ph3—OCFF-Cy-Ph3—CFFO—Ph3—F | 5.0 |
| 3-Ph3—OCFF—Pr—Ph3—CFFO—Ph3—F | 5.0 |
| 3-Ph—Ph3—OCFF-Cy-Ph3—F | 8.0 |
| 3-Pr—Ph3—OCFF-Cy-Ph3—F | 7.0 |
| 3-Pr—Ph3—O1-Cy-Ph3—F | 5.0 |
| total | 100.0 |
| Tni(° C.) | 71.7 |
| T-n (° C.) | −39.0 |
| Vth (volt) | 1.33 |
| Δε | 11.1 |
| Δn | 0.081 |
| η20° C. (mPa · s) | 9.7 |

Example 10

The resulting liquid crystal composition and the physical properties thereof are shown below.

TABLE 12

| | |
|---|---|
| Mix-B | 40.0 |
| 3-Cy-Ph3—O1—Ph3—F | 5.0 |
| 3-Ph—Ph3—O1—Ph3—F | 5.0 |
| 3-Cy-Ph3—O1—Ph3—Ph—OCFFF | 10.0 |
| 1d1-Cy-Cy-Ph3—O1—Ph3—F | 10.0 |
| 3-Ph3—O1-Cy-Ph—OCFFF | 5.0 |
| 3-Ph3—OCFF-Cy-Ph3—OCFFF | 5.0 |
| 3-Ph3—OCFF—Pr—Ph3—F | 5.0 |
| 3-Ph—Ph3—OCFF-Cy-Ph3—F | 5.0 |
| 3-Pr—Ph3—OCFF-Cy-Ph3—F | 5.0 |
| 3-Pr—Ph3—O1-Cy-Ph3—F | 5.0 |
| total | 100.0 |
| Tni(° C.) | 76.9 |
| T-n (° C.) | −45.0 |
| Vth (volt) | 1.40 |
| Δε | 9.9 |
| Δn | 0.081 |
| η20° C. (mPa · s) | 10.8 |

Example 11

The resulting liquid crystal composition and the physical properties thereof are shown below.

TABLE 13

| | |
|---|---|
| Mix-B | 50.0 |
| 3-Cy-Ph3—O1—Ph3—F | 5.0 |
| 1d1-Cy-Cy-Ph3—O1—Ph3—F | 10.0 |
| 3-Ph3—O1-Cy-Ph—OCFFF | 5.0 |
| 3-Ph3—OCFF—Pr—Ph3—F | 5.0 |
| 3-Ph3—OCFF-Cy-Ph3—Ph3—F | 5.0 |
| 3-Ph3—OCFF-Cy-Ph3—CFFO—Ph3—F | 5.0 |
| 3-Ph3—OCFF—Pr—Ph3—CFFO—Ph3—F | 5.0 |
| 3-Pr—Ph3—OCFF-Cy-Ph3—F | 5.0 |
| 3-Pr—Ph3—O1-Cy-Ph3—F | 5.0 |
| total | 100.0 |
| Tni(° C.) | 75.3 |
| T-n (° C.) | −44.0 |
| Vth (volt) | 1.37 |
| Δε | 11.1 |
| Δn | 0.074 |
| η20° C. (mPa · s) | 11.8 |

Example 12

The resulting liquid crystal composition and the physical properties thereof are shown below.

TABLE 14

| | |
|---|---|
| Mix-A | 80.0 |
| 3-Cy-Ph1—Ph3—O1—Ph3—F | 5.0 |
| 3-Ph—Ph1—Ph3—O1—Ph3—F | 5.0 |
| 3-Cy-Ph1—Ph3—O1—Ph3—OCFFF | 5.0 |
| 3-Pr—Ph1—Ph3—O1—Ph3—F | 5.0 |
| 3-Ph—Ph1—Np3—F | 5.0 |
| 3-Ph3—O1—Ph—Np3—F | 5.0 |
| 3-Ph—Ph3—OCFF-Cy-Ph3—F | 5.0 |
| 3-Ph3—O1-Cy-Np3—F | 5.0 |
| total | 100.0 |
| Tni(° C.) | 90.6 |
| T-n (° C.) | −41.0 |
| Vth (volt) | 1.51 |
| Δε | 9.0 |
| Δn | 0.131 |
| η20° C. (mPa · s) | 17.9 |

Example 13

The resulting liquid crystal composition and the physical properties thereof are shown below.

TABLE 15

| | |
|---|---|
| Mix-A | 50.0 |
| 3-Ph—Ph1—Ph3—O1—Ph3—F | 5.0 |
| 3-Cy-Ph1—Ph3—O1—Ph3—OCFFF | 5.0 |
| 3-Pr—Ph1—Ph3—O1—Ph3—F | 5.0 |
| 3-Ph3—O1—Ph—Np3—F | 5.0 |
| 3-Ph3—O1-Cy-Ph3—Ph3—F | 5.0 |
| 3-Ph3—OCFF-Cy-Ph3—Ph3—F | 5.0 |
| 3-Ph3—OCFF-Cy-Ph3—CFFO—Ph3—F | 5.0 |
| 3-Ph3—OCFF—Pr—Ph3—CFFO—Ph3—F | 5.0 |
| 3-Ph3—OCFF-Cy-Ph3—Ph3—OCFFF | 5.0 |
| 3-Ph—Ph3—OCFF-Cy-Ph3—F | 5.0 |
| total | 100.0 |
| Tni(° C.) | 85.7 |
| T-n (° C.) | −45.0 |
| Vth (volt) | 1.10 |
| Δε | 15.6 |
| Δn | 0.117 |
| η20° C. (mPa · s) | 19.8 |

Example 14

The resulting liquid crystal composition and the physical properties thereof are shown below.

TABLE 16

| | |
|---|---|
| Mix-A | 50.0 |
| 3-Ph—Ph3—O1—Ph3—F | 5.0 |
| 3-Cy-Ph1—Ph3—O1—Ph3—F | 5.0 |
| 3-Cy-Ph3—O1—Ph3—Ph—OCFFF | 5.0 |
| 3-Ph—Ph1—Np3—F | 5.0 |
| 3-Ph3—OCFF-Cy-Ph3—OCFFF | 5.0 |
| 3-Ph3—O1-Cy-Ph3—Ph3—F | 5.0 |
| 3-Ph3—OCFF-Cy-Ph3—Ph3—OCFFF | 5.0 |
| 3-Ph3—OCFF-Cy-Pr—Ph3—F | 5.0 |
| 3-Ph3—O1-Cy-Np3—F | 5.0 |
| 3-Ph3—OCFF-Cy-Ph1—Ph3—CFFO—Ph3—F | 5.0 |
| total | 100.0 |
| Tni(° C.) | 87.1 |
| T-n (° C.) | −46.0 |
| Vth (volt) | 1.27 |
| Δε | 12.3 |
| Δn | 0.123 |
| η20° C. (mPa · s) | 17.5 |

Example 15

The resulting liquid crystal composition and the physical properties thereof are shown below.

TABLE 17

| | |
|---|---|
| Mix-A | 50.0 |
| 3-Cy-Ph1—Ph3—O1—Ph3—F | 5.0 |
| 3-Ph—Ph1—Ph3—O1—Ph3—F | 5.0 |
| 3-Cy-Ph3—O1—Ph3—Ph—OCFFF | 5.0 |
| 1d1-Cy-Cy-Ph3—O1—Ph3—F | 5.0 |
| 3-Ph—Ph1—Np3—F | 5.0 |
| 3-Ph3—OCFF-Cy-Ph3—Ph3—OCFFF | 5.0 |
| 3-Ph—Ph3—OCFF-Cy-Ph3—F | 5.0 |
| 3-Pr—Ph3—OCFF-Cy-Ph3—F | 5.0 |
| 3-Pr—Ph3—O1-Cy-Ph3—F | 5.0 |
| 3-Ph3—OCFF-Cy-Pr—Ph3—F | 5.0 |
| total | 100.0 |

TABLE 17-continued

| | |
|---|---|
| Tni(° C.) | 100.0 |
| T-n (° C.) | −48.0 |
| Vth (volt) | 1.38 |
| Δε | 10.8 |
| Δn | 0.115 |
| η20° C. (mPa · s) | 17.9 |

Example 16

The resulting liquid crystal composition and the physical properties thereof are shown below.

TABLE 18

| | |
|---|---|
| Mix-B | 40.0 |
| 3-Cy-Ph3—O1—Ph3—F | 10.0 |
| 3-Cy-Ph3—O1—Ph3—Ph—OCFFF | 10.0 |
| 1d1-Cy-Cy-Ph3—O1—Ph3—F | 10.0 |
| 3-Ph3—OCFF-Cy-Ph3—OCFFF | 10.0 |
| 3-Ph3—OCFF—Pr—Ph3—F | 10.0 |
| 3-Pr—Ph3—O1-Cy-Ph3—F | 10.0 |
| total | 100.0 |
| Tni(° C.) | 74.3 |
| T-n (° C.) | −41.0 |
| Vth (volt) | 1.53 |
| Δε | 8.9 |
| Δn | 0.077 |
| η20° C. (mPa · s) | 9.5 |

Example 17

The resulting liquid crystal composition and the physical properties thereof are shown below.

TABLE 19

| | |
|---|---|
| Mix-B | 45.0 |
| 3-Ph—Ph3—O1—Ph3—F | 5.0 |
| 3-Pr—Ph1—Ph3—O1—Ph3—F | 5.0 |
| 3-Ph3—O1—Ph—Np3—F | 5.0 |
| 3-Ph3—O1-Cy-Ph—OCFFF | 5.0 |
| 3-Ph3—O1-Cy-Ph3—Ph3—F | 5.0 |
| 3-Ph3—OCFF-Cy-Ph3—Ph3—F | 5.0 |
| 3-Ph3—OCFF-Cy-Ph3—CFFO—Ph3—F | 5.0 |
| 3-Ph3—OCFF—Pr—Ph3—CFFO—Ph3—F | 5.0 |
| 3-Ph3—OCFF-Cy-Pr—Ph3—F | 5.0 |
| 3-Ph3—O1-Cy-Np3—F | 5.0 |
| 3-Ph3—OCFF-Cy-Ph1—Ph3—CFFO—Ph3—F | 5.0 |
| total | 100.0 |
| Tni(° C.) | 75.5 |
| T-n (° C.) | −41.0 |
| Vth (volt) | 1.08 |
| Δε | 15.7 |
| Δε | 0.099 |
| η20° C. (mPa · s) | 17.1 |

Example 18

The resulting liquid crystal composition and the physical properties thereof are shown below.

TABLE 20

| | |
|---|---|
| Mix-B | 45.0 |
| 3-Ph3—O1-Cy-Ph3—F | 5.0 |
| 3-Ph3—CFFO—Pr—Ph3—F | 5.0 |
| 3-Ph3—CFFO-Oc-Ph3—F | 5.0 |
| 3-Ph3—CFFO—Ph3—OCFF-Cy-Ph3—F | 5.0 |

TABLE 20-continued

| | |
|---|---|
| 3-Cy-Ph3—CFFO—Pr—Ph3—F | 5.0 |
| 3-Ph3-Cy-Cy-CFFO—Ph3—F | 5.0 |
| 3-Ph3-Cy-Cy-CFFO—Ph—CFFF | 5.0 |
| 3-Pr—Ph3—O1-Cy-Ph3—F | 5.0 |
| 3-Ph3—OCFF-Cy-Ph3—F | 5.0 |
| 3-Cy-Ph3—OCFF-Cy-Ph3—F | 5.0 |
| 3-Cy-Ph3—OCFF-Cy-Ph3—OCFFF | 5.0 |
| total | 100.0 |
| Tni(° C.) | 74.5 |
| T-n (° C.) | −45.0 |
| Vth (volt) | 1.29 |
| Δε | 11.8 |
| Δn | 0.072 |
| η20° C. (mPa · s) | 13.4 |

Example 19

The resulting liquid crystal composition and the physical properties thereof are shown below.

TABLE 21

| | |
|---|---|
| Mix-B | 30.0 |
| 3-Ph3—O1-Cy-Ph3—F | 10.0 |
| 3-Ph3—CFFO—Pr—Ph3—F | 10.0 |
| 3-Ph3—CFFO-Oc-Ph3—F | 5.0 |
| 3-Ph3—OCFF-Cy-Ph3—Ph3—OCH=FF | 5.0 |
| 3-Ph3—CFFO—Ph3—OCFF-Cy-Ph3—F | 10.0 |
| 3-Ph3-Cy-Cy-CFFO—Ph3—F | 5.0 |
| 3-Ph3-Cy-Cy-CFFO—Ph—CFFF | 5.0 |
| 3-Ph3-Cy-Cy-CFFO—Ph3—CFFF | 5.0 |
| 3-Ph3—O1-Cy-Ph3—Ph—OCFFF | 5.0 |
| 3-Ph3—OCFF-Cy-Ph3—Ph—OCFFF | 5.0 |
| 3-Cy-Ph3—OCFF-Cy-Ph3—OCFFF | 5.0 |
| total | 100.0 |
| Tni(° C.) | 74.2 |
| T-n (° C.) | −44.0 |
| Vth (volt) | 1.02 |
| Δε | 17.3 |
| Δn | 0.082 |
| η20° C. (mPa · s) | 18.2 |

Example 20

The resulting liquid crystal composition and the physical properties thereof are shown below.

TABLE 22

| | |
|---|---|
| Mix-B | 35.0 |
| 3-Ph3—CFFO—Pr—Ph3—F | 5.0 |
| 3-Ph3—CFFO-Oc-Ph3—F | 5.0 |
| 3-Ph3—O1-Cy-Ph3—Ph3—OCFFF | 5.0 |
| 3-Ph3—O1-Cy-Ph3—Ph3—OCH=CFF | 5.0 |
| 3-Ph3—CFFO-Oc-Ph3—Ph3—F | 5.0 |
| 3-Ph3—CFFO—Ph3—OCFF-Cy-Ph3—F | 5.0 |
| 3-Cy-Ph3—CFFO—Pr—Ph3—F | 5.0 |
| 3-Pr—Ph3—O1-Cy-Ph3—F | 5.0 |
| 3-Ph3—O1-Cy-Ph3—F | 5.0 |
| 3-Ph3—O1—Pr—Ph3—Ph3—F | 5.0 |
| 3-Ph3—O1—Pr—Ph3—Ph—OCFFF | 5.0 |
| 3-Ph3—OCFF-Cy-Ph3—F | 5.0 |
| 3-Cy-Ph3—OCFF-Cy-Ph3—F | 5.0 |
| total | 100.0 |
| Tni(° C.) | 75.1 |
| T-n (° C.) | −46.0 |

TABLE 22-continued

| | |
|---|---|
| Vth (volt) | 0.98 |
| Δε | 19.3 |
| Δn | 0.084 |
| η20° C. (mPa · s) | 19.5 |

Example 21

The resulting liquid crystal composition and the physical properties thereof are shown below.

TABLE 23

| | |
|---|---|
| Mix-B | 40.0 |
| 3-Ph3—O1-Cy-Ph3—F | 5.0 |
| 3-Ph3—CFFO—Pr—Ph3—F | 5.0 |
| 3-Ph3—CFFO-Oc-Ph3—F | 5.0 |
| 3-Cy-Ph3—CFFO—Pr—Ph3—F | 5.0 |
| 3-Ph3-Cy-Cy-CFFO—Ph3—F | 5.0 |
| 3-Ph3-Cy-Cy-CFFO—Ph—CFFF | 5.0 |
| 3-Ph3-Cy-Cy-CFFO—Ph3—CFFF | 5.0 |
| 3-Pr—Ph3—O1-Cy-Ph3—F | 5.0 |
| 3-Ph3—O1—Pr—Ph3—Ph3—F | 5.0 |
| 3-Ph3—OCFF-Cy-Ph3—F | 5.0 |
| 3-Cy-Ph3—OCFF-Cy-Ph3—F | 5.0 |
| 3-Cy-Ph3—OCFF-Cy-Ph3—OCFFF | 5.0 |
| total | 100.0 |
| Tni(° C.) | 76.9 |
| T-n (° C.) | −48.0 |
| Vth (volt) | 1.25 |
| Δε | 13.1 |
| Δn | 0.072 |
| η20° C. (mPa · s) | 15.0 |

Example 22

The resulting liquid crystal composition and the physical properties thereof are shown below.

TABLE 24

| | |
|---|---|
| Mix-B | 45.0 |
| 3-Ph3—O1-Cy-Ph3—Ph3—OCFFF | 5.0 |
| 3-Ph3—OCFF-Cy-Ph3—Ph3—OCH=FF | 5.0 |
| 3-Ph3-Cy-Cy-CFFO—Ph—CFFF | 5.0 |
| 3-Ph3—O1-Cy-Ph3—Ph3—F | 5.0 |
| 3-Ph3—O1-Cy-Ph3—Ph—OCFFF | 5.0 |
| 3-Ph3—O1—Pr—Ph3—Ph—OCFFF | 5.0 |
| 3-Ph3—OCFF-Cy-Ph3—F | 5.0 |
| 3-Ph3—OCFF-Cy-Ph3—Ph—OCFFF | 5.0 |
| 3-Pr—Ph—Ph3—OCFFF | 5.0 |
| 3-Cy-Ph1—Ph3—O1—Ph3—OCFFF | 5.0 |
| 3-Ph—Ph1—Ph3—CFFO—Ph3—F | 5.0 |
| total | 100.0 |
| Tni(° C.) | 93.8 |
| T-n (° C.) | −45.0 |
| Vth (volt) | 1.18 |
| Δε | 14.4 |
| Δn | 0.097 |
| η20° C. (mPa · s) | 18.8 |

Example 23

The resulting liquid crystal composition and the physical properties thereof are shown below.

TABLE 25

| | |
|---|---|
| Mix-B | 65.0 |
| 3-Ph3—CFFO—Pr—Ph3—F | 5.0 |
| 3-Ph3—CFFO-Oc-Ph3—F | 5.0 |
| 3-Ph3-Cy-Cy-CFFO—Ph3—F | 5.0 |
| 3-Ph3-Cy-Cy-CFFO—Ph—CFFF | 5.0 |
| 3-Ph3—OCFF-Cy-Ph3—F | 5.0 |
| 3-Pr—Ph—Ph3—OCFFF | 5.0 |
| 3-Cy-Ph1—Ph3—O1—Ph3—OCFFF | 5.0 |
| total | 100.0 |
| Tni(° C.) | 74.6 |
| T-n (° C.) | −40.0 |
| Vth (volt) | 1.66 |
| Δε | 7.5 |
| Δn | 0.075 |
| η20° C. (mPa · s) | 10.9 |

Example 24

The resulting liquid crystal composition and the physical properties thereof are shown below.

TABLE 26

| | |
|---|---|
| Mix-A | 60.0 |
| 3-Ph3-O1-Cy-Ph3-Ph3-OCFFF | 5.0 |
| 3-Ph3-O1-Cy-Ph3-Ph3-OCH=CFF | 5.0 |
| 3-Ph3-CFFO-Oc-Ph3-Ph3-F | 5.0 |
| 3-Ph3-OCFF-Cy-Ph3-Ph3-OCH=FF | 5.0 |
| 3-Ph3-O1-Cy-Ph3-Ph3-F | 5.0 |
| 3-Ph3-O1-Cy-Ph3-Ph-OCFFF | 5.0 |
| 3-Ph3-OCFF-Cy-Ph3-Ph-OCFFF | 5.0 |
| 3-Cy-Ph1-Ph3-O1-Ph3-OCFFF | 5.0 |
| total | 100.0 |
| Tni (° C.) | 95.1 |
| T-n (° C.) | −40.0 |
| Vth (volt) | 1.30 |
| Δε | 13.0 |
| Δn | 0.112 |
| η20° C. (mPa · s) | 18.9 |

Example 25

The resulting liquid crystal composition and the physical properties thereof are shown below.

TABLE 27

| | |
|---|---|
| Mix-A | 60.0 |
| 3-Ph3-O1-Cy-Ph3-F | 5.0 |
| 3-Ph3-O1-Cy-Ph3-OCH=CFF | 5.0 |
| 3-Ph3-CFFO-Oc-Ph3-Ph3-F | 5.0 |
| 3-Ph3-CFFO-Ph3-OCFF-Cy-Ph3-F | 5.0 |
| 3-Ph3-O1-Cy-Ph3-Ph3-F | 5.0 |
| 3-Ph3-O1-Pr-Ph3-Ph3-F | 5.0 |
| 3-Ph3-O1-Pr-Ph3-Ph-OCFFF | 5.0 |
| 3-Cy-Ph1-Ph3-O1-Ph3-OCFFF | 5.0 |
| total | 100.0 |
| Tni (° C.) | 79.9 |
| T-n (° C.) | −43.0 |
| Vth (volt) | 1.26 |
| Δε | 12.9 |
| Δn | 0.106 |
| η20° C. (mPa · s) | 17.7 |

Example 26

The resulting liquid crystal composition and the physical properties thereof are shown below.

TABLE 28

| | |
|---|---|
| Mix-B | 40.0 |
| 3-Ph3-OCFF-Cy-Ph3-OCFFF | 10.0 |
| 3-Ph3-OCFF-Pr-Ph3-F | 10.0 |
| 3-Ph3-OCFF-Cy-Ph3-Ph-OCFFF | 5.0 |
| 3-Ph3-OCFF-Cy-Ph3-Ph3-OCFFF | 5.0 |
| 3-Cy-Ph3-OCFF-Cy-Ph3-F | 5.0 |
| 3-Cy-Ph3-O1-Cy-Ph3-F | 5.0 |
| 3-Cy-Ph3-O1-Ph-OCFFF | 10.0 |
| 3-Cy-Pr-Ph3-O1-Ph3-F | 5.0 |
| 0d1-Cy-Ph3-O1-Ph-OCFFF | 5.0 |
| total | 100.0 |
| Tni (° C.) | 72.9 |
| T-n (° C.) | −42.0 |
| Vth (volt) | 1.31 |
| Δε | 10.0 |
| Δn | 0.083 |
| η20° C. (mPa · s) | 8.5 |

Example 27

The resulting liquid crystal composition and the physical properties thereof are shown below.

TABLE 29

| | |
|---|---|
| Mix-B | 55.0 |
| 3-Ph3-O1-Cy-Ph-OCFFF | 5.0 |
| 3-Cy-Ph3-OCFF-Cy-Ph3-F | 10.0 |
| 3-Cy-Ph3-O1-Cy-Ph3-F | 10.0 |
| 3-Cy-Ph3-O1-Ph-OCFFF | 10.0 |
| 3-Pr-Ph3-O1-Ph3-F | 5.0 |
| 3-Cy-Pr-Ph3-O1-Ph3-F | 5.0 |
| total | 100.0 |
| Tni (° C.) | 73.6 |
| T-n (° C.) | −40.0 |
| Vth (volt) | 1.77 |
| Δε | 6.5 |
| Δn | 0.070 |
| η20° C. (mPa · s) | 9.4 |

Example 28

The resulting liquid crystal composition and the physical properties thereof are shown below.

TABLE 30

| | |
|---|---|
| Mix-A | 60.0 |
| 3-Ph3-O1-Cy-Ph3-Ph3-F | 5.0 |
| 3-Ph3-OCFF-Cy-Ph3-Ph3-F | 5.0 |
| 3-Ph3-OCFF-Cy-Ph3-Ph-OCFFF | 5.0 |
| 3-Ph3-OCFF-Cy-Ph3-CFFO-Ph3-F | 5.0 |
| 3-Ph3-OCFF-Cy-Ph3-Ph3-OCFFF | 5.0 |
| 3-Ph3-CFFO-Ph3-OCFF-Cy-Ph3-F | 5.0 |
| 3-Pr-Ph1-Ph3-O1-Ph3-F | 5.0 |
| 3-Ph3-O1-Ph-Np3-F | 5.0 |
| total | 100.0 |
| Tni (° C.) | 83.9 |
| T-n (° C.) | −41.0 |
| Vth (volt) | 1.14 |
| Δε | 13.2 |
| Δn | 0.112 |
| η20° C. (mPa · s) | 17.3 |

Example 29

The resulting liquid crystal composition and the physical properties thereof are shown below.

TABLE 31

| | |
|---|---|
| Mix-A | 55.0 |
| 3-Ph3-OCFF-Cy-Ph3-Ph-OCFFF | 5.0 |
| 3-Ph3-O1-Cy-Np3-F | 5.0 |
| 3-Cy-Ph1-Ph3-O1-Ph3-F | 5.0 |
| 3-Ph-Ph1-Ph3-O1-Ph3-F | 5.0 |
| 3-Ph-Ph1-Ph3-O1-Ph-OCFFF | 5.0 |
| 3-Pr-Ph1-Ph3-O1-Ph3-F | 5.0 |
| 3-Ph1-Np3-F | 5.0 |
| 3-Ph-Ph1-Np3-F | 5.0 |
| 3-Ph3-O1-Ph-Np3-F | 5.0 |
| total | 100.0 |
| Tni (° C.) | 85.9 |
| T-n (° C.) | −43.0 |
| Vth (volt) | 1.43 |
| Δε | 9.5 |
| Δn | 0.136 |
| η20° C. (mPa · s) | 19.2 |

Example 30

The resulting liquid crystal composition and the physical properties thereof are shown below.

TABLE 32

| | |
|---|---|
| Mix-A | 50.0 |
| 3-Ph3-OCFF-Cy-Ph3-Ph-OCFFF | 5.0 |
| 3-Ph3-OCFF-Cy-Ph3-Ph3-OCFFF | 5.0 |
| 3-Cy-Ph3-OCFF-Cy-Ph3-F | 5.0 |
| 3-Cy-Ph3-O1-Cy-Ph3-F | 5.0 |
| 3-Cy-Ph1-Ph3-O1-Ph3-F | 5.0 |
| 3-Ph-Ph1-Ph3-O1-Ph3-F | 5.0 |
| 3-Ph-Ph1-Ph3-O1-Ph-OCFFF | 5.0 |
| 3-Pr-Ph1-Ph3-O1-Ph3-F | 5.0 |
| 3-Cy-Pr-Ph3-O1-Ph3-F | 5.0 |
| 3-Ph-Ph1-Np3-F | 5.0 |
| total | 100.0 |
| Tni (° C.) | 101.9 |
| T-n (° C.) | −45.0 |
| Vth (volt) | 1.43 |
| Δε | 10.6 |
| Δn | 0.120 |
| η20° C. (mPa · s) | 19.2 |

Example 31

The resulting liquid crystal composition and the physical properties thereof are shown below.

TABLE 33

| | |
|---|---|
| Mix-A | 55.0 |
| 3-Ph3-OCFF-Cy-Ph3-OCFFF | 5.0 |
| 3-Ph3-OCFF-Pr-Ph3-F | 5.0 |
| 3-Ph3-O1-Cy-Ph3-Ph3-F | 5.0 |
| 3-Ph3-OCFF-Cy-Ph3-Ph3-F | 5.0 |
| 3-Ph3-OCFF-Cy-Ph3-Ph-OCFFF | 5.0 |
| 3-Ph3-OCFF-Cy-Ph3-CFFO-Ph3-F | 5.0 |
| 3-Ph3-CFFO-Ph3-OCFF-Cy-Ph3-F | 5.0 |
| 3-Ph3-O1-Cy-Np3-F | 5.0 |
| 0d1-Cy-Ph3-O1-Ph-OCFFF | 5.0 |
| total | 100.0 |
| Tni (° C.) | 73.3 |
| T-n (° C.) | −42.0 |
| Vth (volt) | 1.19 |
| Δε | 11.5 |
| Δn | 0.108 |
| η20° C. (mPa · s) | 12.7 |

Example 32

The resulting liquid crystal composition and the physical properties thereof are shown below.

TABLE 34

| | |
|---|---|
| Mix-A | 60.0 |
| 3-Ph3-O1-Cy-Ph-OCFFF | 5.0 |
| 3-Ph3-OCFF-Cy-Ph3-Ph-OCFFF | 8.0 |
| 3-Ph-Ph3-O1-Ph3-F | 5.0 |
| 3-Ph-Ph1-Ph3-O1-Ph-OCFFF | 5.0 |
| 3-Pr-Ph3-O1-Ph3-F | 5.0 |
| 3-Cy-Pr-Ph3-O1-Ph3-F | 7.0 |
| 3-Ph1-Np3-F | 5.0 |
| total | 100.0 |
| Tni (° C.) | 71.2 |
| T-n (° C.) | −40.0 |
| Vth (volt) | 1.58 |
| Δε | 7.4 |
| Δn | 0.107 |
| η20° C. (mPa · s) | 13.6 |

Example 33

The resulting liquid crystal composition and the physical properties thereof are shown below.

TABLE 35

| | |
|---|---|
| Mix-A | 55.0 |
| 3-Ph3-OCFF-Cy-Ph3-OCFFF | 5.0 |
| 3-Ph3-OCFF-Pr-Ph3-F | 5.0 |
| 3-Ph3-OCFF-Cy-Ph3-Ph-OCFFF | 5.0 |
| 3-Ph3-OCFF-Cy-Ph3-CFFO-Ph3-F | 5.0 |
| 3-Ph3-O1-Cy-Np3-F | 5.0 |
| 3-Ph-Ph3-O1-Ph3-F | 5.0 |
| 3-Cy-Ph1-Ph3-O1-Ph3-F | 5.0 |
| 3-Cy-Pr-Ph3-O1-Ph3-F | 5.0 |
| 0d1-Cy-Ph3-O1-Ph-OCFFF | 5.0 |
| total | 100.0 |
| Tni (° C.) | 72.5 |
| T-n (° C.) | −45.0 |
| Vth (volt) | 1.42 |
| Δε | 8.6 |
| Δn | 0.107 |
| η20° C. (mPa · s) | 12.1 |

Example 34

The resulting liquid crystal composition and the physical properties thereof are shown below.

TABLE 36

| | |
|---|---|
| 3-Cy-d-Cy-Cy-1d0 | 5.0 |
| 3-Cy-d-Cy-Cy-2 | 5.0 |
| 3-Pr-Cy-d-Cy-1d0 | 5.0 |
| 3-Pr-Cy-d-Cy-2 | 5.0 |
| 5-Ph-Ph-1 | 5.0 |
| 0d1-Cy-Cy-3 | 10.0 |
| 1d1-Cy-Cy-2 | 10.0 |
| 0d3-Cy-Cy-3 | 5.0 |
| 1d1-Cy-Cy-3 | 5.0 |
| 3-Ph3-O1-Cy-Ph-OCFFF | 10.0 |
| 3-Ph3-OCFF-Pr-Ph3-F | 10.0 |
| 3-Ph3-OCFF-Cy-Ph3-Ph3-F | 5.0 |

TABLE 36-continued

| | |
|---|---|
| 3-Ph3-OCFF-Cy-Ph3-CFFO-Ph3-F | 5.0 |
| 3-Ph3-CFFO-Ph3-OCFF-Cy-Ph3-F | 5.0 |
| 3-Cy-Ph3-OCFF-Cy-Ph3-F | 5.0 |
| 3-Cy-Ph3-O1-Cy-Ph3-F | 5.0 |
| total | 100.0 |
| Tni (° C.) | 80.7 |
| T-n (° C.) | −38.0 |
| Vth (volt) | 1.30 |
| Δε | 10.2 |
| Δn | 0.080 |
| η20° C. (mPa · s) | 10.6 |

Example 35

The resulting liquid crystal composition and the physical properties thereof are shown below.

TABLE 37

| | |
|---|---|
| 3-Cy-d-Cy-Cy-2 | 5.0 |
| 3-Pr-Cy-d-Cy-1d0 | 5.0 |
| 1-Ph-Ph1-Ph-3d0 | 5.0 |
| 5-Ph-Ph-1 | 5.0 |
| 0d1-Cy-Cy-3 | 10.0 |
| 1d1-Cy-Cy-2 | 10.0 |
| 1d1-Cy-Cy-3 | 5.0 |
| 3-Cy-Cy-CFFO-Ph3-F | 5.0 |
| 3-Cy-Ph1-Ph3-CFFO-Ph3-F | 5.0 |
| 3-Ph-Ph-Ph3-CFFO-Ph3-F | 5.0 |
| 3-Ph-Ph1-Ph3-CFFO-Ph3-F | 5.0 |
| 3-Cy-Cy-Ph3-F | 5.0 |
| 3-Cy-Ph-Ph3-F | 5.0 |
| 3-Ph-Ph1-Ph3-F | 5.0 |
| 3-Pr-Cy-CFFO-Ph3-F | 5.0 |
| 3-Pr-Ph1-Ph3-CFFO-Ph3-F | 5.0 |
| 3-Ph3-O1-Cy-Ph-OCFFF | 5.0 |
| 3-Cy-Ph3-O1-Cy-Ph3-F | 5.0 |
| total | 100.0 |
| Tni (° C.) | 84.1 |
| T-n (° C.) | −38.0 |
| Vth (volt) | 1.33 |
| Δε | 10.5 |
| Δn | 0.111 |
| η20° C. (mPa · s) | 17.6 |

Example 36

The resulting liquid crystal composition and the physical properties thereof are shown below.

TABLE 38

| | |
|---|---|
| 3-Cy-d-Cy-Cy-1d0 | 5.0 |
| 3-Pr-Cy-d-Cy-2 | 5.0 |
| 5-Ph-Ph-1 | 5.0 |
| 0d1-Cy-Cy-3 | 10.0 |
| 1d1-Cy-Cy-2 | 10.0 |
| 0d3-Cy-Cy-3 | 10.0 |
| 1d1-Cy-Cy-3 | 10.0 |
| 3-Cy-Cy-CFFO-Ph3-F | 5.0 |
| 3-Cy-Cy-Ph3-F | 5.0 |
| 3-Cy-Ph-Ph3-F | 5.0 |
| 3-Pr-Cy-CFFO-Ph3-F | 5.0 |
| 3-Ph3-O1-Cy-Ph-OCFFF | 5.0 |
| 3-Ph3-OCFF-Pr-Ph3-F | 5.0 |
| 3-Ph3-OCFF-Cy-Ph3-CFFO-Ph3-F | 5.0 |
| 3-Ph3-CFFO-Ph3-OCFF-Cy-Ph3-F | 5.0 |
| 3-Cy-Ph3-O1-Cy-Ph3-F | 5.0 |
| total | 100.0 |
| Tni (° C.) | 74.3 |

TABLE 38-continued

| | |
|---|---|
| T-n (° C.) | −45.0 |
| Vth (volt) | 1.57 |
| Δε | 7.2 |
| Δn | 0.074 |
| η20° C. (mPa · s) | 10.8 |

Example 37

The resulting liquid crystal composition and the physical properties thereof are shown below.

TABLE 39

| | |
|---|---|
| 1-Ph-Ph1-Ph-3d0 | 5.0 |
| 0d1-Cy-Cy-3 | 10.0 |
| 1d1-Cy-Cy-2 | 10.0 |
| 0d3-Cy-Cy-3 | 10.0 |
| 1d1-Cy-Cy-3 | 10.0 |
| 3-Cy-Ph1-Ph3-CFFO-Ph3-F | 5.0 |
| 3-Ph-Ph-Ph3-CFFO-Ph3-F | 5.0 |
| 3-Ph-Ph1-Ph3-CFFO-Ph3-F | 5.0 |
| 3-Ph-Ph1-Ph3-F | 5.0 |
| 3-Pr-Cy-CFFO-Ph3-F | 5.0 |
| 3-Pr-Ph1-Ph3-CFFO-Ph3-F | 5.0 |
| 3-Ph3-OCFF-Pr-Ph3-F | 5.0 |
| 3-Ph3-OCFF-Cy-Ph3-F | 5.0 |
| 3-Ph3-OCFF-Cy-Ph3-CFFO-Ph3-F | 5.0 |
| 3-Ph3-CFFO-Ph3-OCFF-Cy-Ph3-F | 5.0 |
| 3-Cy-Ph3-O1-Cy-Ph3-F | 5.0 |
| total | 100.0 |
| Tni (° C.) | 74.7 |
| T-n (° C.) | −44.0 |
| Vth (volt) | 1.09 |
| Δε | 15.0 |
| Δn | 0.108 |
| η20° C. (mPa · s) | 17.5 |

Example 38

The resulting liquid crystal composition and the physical properties thereof are shown below.

TABLE 40

| | |
|---|---|
| 3-Cy-d-Cy-Cy-1d0 | 5.0 |
| 3-Cy-d-Cy-Cy-2 | 5.0 |
| 1-Ph-Ph1-Ph-3d0 | 5.0 |
| 0d1-Cy-Cy-3 | 10.0 |
| 1d1-Cy-Cy-2 | 15.0 |
| 1d1-Cy-Cy-3 | 15.0 |
| 3-Cy-Ph1-Ph3-CFFO-Ph3-F | 5.0 |
| 3-Ph-Ph-Ph3-CFFO-Ph3-F | 5.0 |
| 3-Ph-Ph1-Ph3-CFFO-Ph3-F | 5.0 |
| 3-Ph-Ph1-Ph3-F | 5.0 |
| 3-Pr-Ph1-Ph3-CFFO-Ph3-F | 5.0 |
| 3-Ph3-OCFF-Pr-Ph3-F | 5.0 |
| 3-Ph3-OCFF-Cy-Ph3-F | 5.0 |
| 3-Ph3-OCFF-Cy-Ph3-CFFO-Ph3-F | 5.0 |
| 3-Ph3-CFFO-Ph3-OCFF-Cy-Ph3-F | 5.0 |
| total | 100.0 |
| Tni (° C.) | 84.9 |
| T-n (° C.) | −44.0 |
| Vth (volt) | 1.20 |
| Δε | 13.6 |
| Δn | 0.110 |
| η20° C. (mPa · s) | 16.6 |

Example 39

The resulting liquid crystal composition and the physical properties thereof are shown below.

TABLE 41

| | |
|---|---|
| 3-Cy-d-Cy-Cy-1d0 | 5.0 |
| 3-Cy-d-Cy-Cy-2 | 5.0 |
| 3-Pr-Cy-d-Cy-1d0 | 5.0 |
| 0d1-Cy-Cy-3 | 5.0 |
| 1d1-Cy-Cy-2 | 10.0 |
| 0d3-Cy-Cy-3 | 10.0 |
| 1d1-Cy-Cy-3 | 10.0 |
| 3-Cy-Cy-CFFO-Ph3-F | 5.0 |
| 3-Cy-Ph1-Ph3-CFFO-Ph3-F | 5.0 |
| 3-Ph-Ph-Ph3-CFFO-Ph3-F | 5.0 |
| 3-Ph-Ph1-Ph3-CFFO-Ph3-F | 5.0 |
| 3-Cy-Cy-Ph3-F | 5.0 |
| 3-Pr-Cy-CFFO-Ph3-F | 5.0 |
| 3-Pr-Ph1-Ph3-CFFO-Ph3-F | 5.0 |
| 3-Ph3-OCFF-Cy-Ph3-Ph3-F | 5.0 |
| 3-Cy-Ph3-OCFF-Cy-Ph3-F | 5.0 |
| 3-Cy-Ph3-O1-Cy-Ph3-F | 5.0 |
| total | 100.0 |
| Tni (° C.) | 103.3 |
| T-n (° C.) | −45.0 |
| Vth (volt) | 1.32 |
| Δε | 11.4 |
| Δn | 0.088 |
| η20° C. (mPa · s) | 17.7 |

Example 40

The resulting liquid crystal composition and the physical properties thereof are shown below.

TABLE 42

| | |
|---|---|
| 3-Cy-d-Cy-Cy-1d0 | 5.0 |
| 0d1-Cy-Cy-3 | 20.0 |
| 1d1-Cy-Cy-2 | 5.0 |
| 0d3-Cy-Cy-3 | 10.0 |
| 1d1-Cy-Cy-3 | 10.0 |
| 3-Cy-Cy-CFFO-Ph3-F | 5.0 |
| 3-Ph-Ph-Ph3-CFFO-Ph3-F | 8.0 |
| 3-Ph-Ph1-Ph3-CFFO-Ph3-F | 5.0 |
| 3-Cy-Cy-Ph3-F | 5.0 |
| 3-Pr-Ph1-Ph3-CFFO-Ph3-F | 7.0 |
| 3-Ph3-OCFF-Cy-Ph3-F | 5.0 |
| 3-Cy-Ph3-OCFF-Cy-Ph3-F | 7.0 |
| 3-Cy-Ph3-O1-Cy-Ph3-F | 8.0 |
| total | 100.0 |
| Tni (° C.) | 89.2 |
| T-n (° C.) | −41.0 |
| Vth (volt) | 1.28 |
| Δε | 11.5 |
| Δn | 0.087 |
| η20° C. (mPa · s) | 15.9 |

Example 41

The resulting liquid crystal composition and the physical properties thereof are shown below.

TABLE 43

| | |
|---|---|
| 3-Cy-d-Cy-Cy-1d0 | 5.0 |
| 3-Pr-Cy-d-Cy-2 | 5.0 |
| 0d1-Cy-Cy-3 | 10.0 |
| 1d1-Cy-Cy-2 | 10.0 |
| 0d3-Cy-Cy-3 | 10.0 |
| 1d1-Cy-Cy-3 | 10.0 |
| 3-Cy-Ph1-Ph3-CFFO-Ph3-F | 5.0 |
| 3-Cy-Cy-Ph3-F | 5.0 |
| 3-Cy-Ph-Ph3-F | 5.0 |
| 3-Ph-Ph1-Ph3-F | 5.0 |
| 3-Pr-Cy-CFFO-Ph3-F | 5.0 |
| 3-Ph3-O1-Cy-Ph-OCFFF | 5.0 |
| 3-Ph3-OCFF-Pr-Ph3-F | 5.0 |
| 3-Ph3-OCFF-Cy-Ph3-Ph3-F | 5.0 |
| 3-Ph3-OCFF-Cy-Ph3-CFFO-Ph3-F | 5.0 |
| 3-Ph3-CFFO-Ph3-OCFF-Cy-Ph3-F | 5.0 |
| total | 100.0 |
| Tni (° C.) | 74.1 |
| T-n (° C.) | −48.0 |
| Vth (volt) | 1.23 |
| Δε | 11.3 |
| Δn | 0.083 |
| η20° C. (mPa · s) | 13.1 |

Example 42

The resulting liquid crystal composition and the physical properties thereof are shown below.

TABLE 44

| | |
|---|---|
| 0d1-Cy-Cy-3 | 10.0 |
| 1d1-Cy-Cy-1d1 | 10.0 |
| 0d3-Cy-Cy-3d0 | 10.0 |
| 3-Cy-Cy-2 | 5.0 |
| 3-Cy-Cy-O2 | 5.0 |
| 3-Cy-Cy-O2d0 | 5.0 |
| 3-Cy-Cy-CFFO-Ph3-F | 10.0 |
| 3-Cy-Ph1-Ph3-CFFO-Ph3-F | 5.0 |
| 3-Ph-Ph1-Ph3-CFFO-Ph3-F | 5.0 |
| 3-Ph3-OCFF-Cy-Ph3-OCFFF | 5.0 |
| 3-Ph3-OCFF-Pr-Ph3-F | 5.0 |
| 3-Ph3-OCFF-Cy-Ph3-F | 5.0 |
| 3-Ph3-OCFF-Cy-Ph3-CFFO-Ph3-F | 5.0 |
| 3-Ph3-CFFO-Ph3-OCFF-Cy-Ph3-F | 5.0 |
| 3-Cy-Ph3-OCFF-Cy-Ph3-F | 5.0 |
| 3-Cy-Ph3-O1-Cy-Ph3-F | 5.0 |
| total | 100.0 |
| Tni (° C.) | 72.7 |
| T-n (° C.) | −40.0 |
| Vth (volt) | 1.13 |
| Δε | 13.3 |
| Δn | 0.083 |
| η20° C. (mPa · s) | 13.0 |

Example 43

The resulting liquid crystal composition and the physical properties thereof are shown below.

TABLE 45

| | |
|---|---|
| 0d1-Cy-Cy-3 | 10.0 |
| 1d1-Cy-Cy-1d1 | 10.0 |
| 3-Cy-d-Cy-3 | 5.0 |
| 3-Cy-d-Cy-5 | 5.0 |
| 3-Cy-d-Cy-1d0 | 5.0 |
| 1d1-Cy-d-Cy-1d0 | 5.0 |
| 3-Cy-Cy-CFFO-Ph3-F | 5.0 |
| 3-Cy-Ph1-Ph3-CFFO-Ph3-F | 5.0 |
| 3-Ph-Ph1-Ph3-CFFO-Ph3-F | 5.0 |
| 3-Pr-Ph-Ph3-OCFFF | 5.0 |
| 3-Cy-Ph-Ph3-F | 5.0 |
| 3-Pr-Cy-CFFO-Ph3-F | 5.0 |
| 3-Pr-Ph1-Ph3-CFFO-Ph3-F | 5.0 |
| 3-Ph3-O1-Cy-Ph-OCFFF | 5.0 |
| 3-Ph3-OCFF-Cy-Ph3-OCFFF | 5.0 |
| 3-Ph3-OCFF-Pr-Ph3-F | 5.0 |
| 3-Cy-Ph3-OCFF-Cy-Ph3-F | 5.0 |
| 3-Cy-Ph3-O1-Cy-Ph3-F | 5.0 |
| total | 100.0 |

TABLE 45-continued

| | |
|---|---|
| Tni (° C.) | 72.2 |
| T-n (° C.) | −40.0 |
| Vth (volt) | 1.19 |
| Δε | 11.1 |
| Δn | 0.091 |
| η20° C. (mPa · s) | 13.0 |

Example 44

The resulting liquid crystal composition and the physical properties thereof are shown below.

TABLE 46

| | |
|---|---|
| 0d1-Cy-Cy-3 | 5.0 |
| 1d1-Cy-Cy-1d1 | 10.0 |
| 0d3-Cy-Cy-3d0 | 5.0 |
| 3-Cy-Cy-O2 | 5.0 |
| 3-Cy-d-Cy-3 | 10.0 |
| 3-Cy-d-Cy-5 | 5.0 |
| 3-Cy-d-Cy-1d0 | 5.0 |
| 1d1-Cy-d-Cy-1d0 | 5.0 |
| 3-Ph3-OCFF-Cy-Ph3-OCFFF | 7.0 |
| 3-Ph3-OCFF-Pr-Ph3-F | 8.0 |
| 3-Ph3-OCFF-Cy-Ph3-Ph3-F | 8.0 |
| 3-Ph3-OCFF-Cy-Ph3-CFFO-Ph3-F | 5.0 |
| 3-Ph3-CFFO-Ph3-OCFF-Cy-Ph3-F | 7.0 |
| 3-Cy-Ph3-OCFF-Cy-Ph3-F | 7.0 |
| 3-Cy-Ph3-O1-Cy-Ph3-F | 8.0 |
| total | 100.0 |
| Tni (° C.) | 72.3 |
| T-n (° C.) | −38.0 |
| Vth (volt) | 1.13 |
| Δε | 12.5 |
| Δn | 0.079 |
| η20° C. (mPa · s) | 10.3 |

Example 45

The resulting liquid crystal composition and the physical properties thereof are shown below.

TABLE 47

| | |
|---|---|
| 0d1-Cy-Cy-3 | 10.0 |
| 1d1-Cy-Cy-1d1 | 10.0 |
| 3-Cy-d-Cy-5 | 10.0 |
| 3-Cy-d-Cy-1d0 | 10.0 |
| 1d1-Cy-d-Cy-1d0 | 10.0 |
| 3-Cy-Cy-CFFO-Ph3-F | 5.0 |
| 3-Cy-Ph1-Ph3-CFFO-Ph3-F | 5.0 |
| 3-Ph-Ph1-Ph3-CFFO-Ph3-F | 5.0 |
| 3-Pr-Ph-Ph3-OCFFF | 5.0 |
| 3-Pr-Cy-CFFO-Ph3-F | 5.0 |
| 3-Pr-Ph1-Ph3-CFFO-Ph3-F | 5.0 |
| 3-Ph3-OCFF-Cy-Ph3-Ph3-F | 5.0 |
| 3-Ph3-CFFO-Ph3-OCFF-Cy-Ph3-F | 5.0 |
| 3-Cy-Ph3-OCFF-Cy-Ph3-F | 5.0 |
| 3-Cy-Ph3-O1-Cy-Ph3-F | 5.0 |
| total | 100.0 |
| Tni (° C.) | 80.1 |
| T-n (° C.) | −44.0 |
| Vth (volt) | 1.16 |
| Δε | 12.4 |
| Δn | 0.088 |
| η20° C. (mPa · s) | 15.5 |

Example 46

The resulting liquid crystal composition and the physical properties thereof are shown below.

TABLE 48

| | |
|---|---|
| 0d1-Cy-Cy-3 | 10.0 |
| 1d1-Cy-Cy-1d1 | 10.0 |
| 3-Cy-Cy-2 | 5.0 |
| 3-Cy-Cy-O2 | 5.0 |
| 3-Cy-d-Cy-3 | 5.0 |
| 3-Cy-d-Cy-5 | 5.0 |
| 1d1-Cy-d-Cy-1d0 | 5.0 |
| 3-Cy-Ph1-Ph3-CFFO-Ph3-F | 5.0 |
| 3-Ph-Ph1-Ph3-CFFO-Ph3-F | 5.0 |
| 3-Pr-Ph-Ph3-OCFFF | 5.0 |
| 3-Pr-Cy-CFFO-Ph3-F | 5.0 |
| 3-Ph3-OCFF-Pr-Ph3-F | 5.0 |
| 3-Ph3-OCFF-Cy-Ph3-F | 5.0 |
| 3-Ph3-OCFF-Cy-Ph3-CFFO-Ph3-F | 5.0 |
| 3-Ph3-CFFO-Ph3-OCFF-Cy-Ph3-F | 5.0 |
| 3-Cy-Ph3-OCFF-Cy-Ph3-F | 7.0 |
| 3-Cy-Ph3-O1-Cy-Ph3-F | 8.0 |
| total | 100.0 |
| Tni (° C.) | 74.6 |
| T-n (° C.) | −41.0 |
| Vth (volt) | 1.13 |
| Δε | 13.8 |
| Δn | 0.084 |
| η20° C. (mPa · s) | 14.6 |

Example 47

The resulting liquid crystal composition and the physical properties thereof are shown below.

TABLE 49

| | |
|---|---|
| 0d1-Cy-Cy-3 | 5.0 |
| 1d1-Cy-Cy-3 | 10.0 |
| 3-Cy-d-Cy-3 | 5.0 |
| 3-Pr-Cy-1d0 | 5.0 |
| 3-Pr-d-Cy-3 | 5.0 |
| 3-Pr-d-Cy-1d0 | 5.0 |
| 3-Cy-Ph-O2 | 5.0 |
| 0d1-Cy-Cy-Ph-1 | 5.0 |
| 3-Cy-Cy-Ph-1 | 5.0 |
| 3-Ph3-O1-Cy-Ph-OCFFF | 5.0 |
| 3-Ph3-OCFF-Cy-Ph3-OCFFF | 5.0 |
| 3-Ph3-OCFF-Pr-Ph3-F | 5.0 |
| 3-Ph3-OCFF-Cy-Ph3-Ph3-F | 7.0 |
| 3-Ph3-OCFF-Cy-Ph3-CFFO-Ph3-F | 5.0 |
| 3-Ph3-CFFO-Ph3-OCFF-Cy-Ph3-F | 7.0 |
| 3-Cy-Ph3-OCFF-Cy-Ph3-F | 8.0 |
| 3-Cy-Ph3-O1-Cy-Ph3-F | 8.0 |
| total | 100.0 |
| Tni (° C.) | 73.3 |
| T-n (° C.) | −39.0 |
| Vth (volt) | 1.16 |
| Δε | 12.0 |
| Δn | 0.081 |
| η20° C. (mPa · s) | 11.8 |

Example 48

The resulting liquid crystal composition and the physical properties thereof are shown below.

TABLE 50

| | |
|---|---|
| 0d1-Cy-Cy-3 | 100 |
| 1d1-Cy-Cy-3 | 10.0 |
| 3-Cy-d-Cy-3 | 5.0 |
| 3-Pr-Cy-1d0 | 5.0 |
| 3-Pr-d-Cy-3 | 5.0 |
| 3-Pr-d-Cy-1d0 | 5.0 |
| 3-Cy-Ph-O2 | 5.0 |

TABLE 50-continued

| | |
|---|---|
| 0d1-Cy-Ph-O4 | 5.0 |
| 3-Cy-Cy-CFFO-Ph3-F | 5.0 |
| 3-Cy-Ph1-Ph3-CFFO-Ph3-F | 5.0 |
| 3-Ph-Ph1-Ph3-CFFO-Ph3-F | 5.0 |
| 3-Pr-Ph-Ph3-OCFFF | 5.0 |
| 3-Pr-Cy-CFFO-Ph3-F | 5.0 |
| 3-Pr-Ph1-Ph3-CFFO-Ph3-F | 5.0 |
| 3-Ph3-OCFF-Cy-Ph3-Ph3-F | 5.0 |
| 3-Cy-Ph3-OCFF-Cy-Ph3-F | 7.0 |
| 3-Cy-Ph3-O1-Cy-Ph3-F | 8.0 |
| total | 100.0 |
| Tni (° C.) | 71.9 |
| T-n (° C.) | −41.0 |
| Vth (volt) | 1.20 |
| Δε | 11.2 |
| Δn | 0.083 |
| η20° C. (mPa · s) | 15.9 |

Example 49

The resulting liquid crystal composition and the physical properties thereof are shown below.

TABLE 51

| | |
|---|---|
| 0d1-Cy-Cy-3 | 10.0 |
| 1d1-Cy-Cy-3 | 10.0 |
| 3-Cy-d-Cy-3 | 10.0 |
| 3-Pr-d-Cy-3 | 10.0 |
| 0d1-Cy-Cy-Ph-1 | 5.0 |
| 3-Cy-Cy-Ph-1 | 5.0 |
| 3-Cy-Cy-CFFO-Ph3-F | 5.0 |
| 3-Pr-Ph-Ph3-OCFFF | 5.0 |
| 3-Cy-Ph-Ph3-F | 5.0 |
| 3-Pr-Cy-CFFO-Ph3-F | 5.0 |
| 3-Ph3-OCFF-Cy-Ph3-OCFFF | 5.0 |
| 3-Ph3-OCFF-Pr-Ph3-F | 5.0 |
| 3-Ph3-OCFF-Cy-Ph3-CFFO-Ph3-F | 5.0 |
| 3-Ph3-CFFO-Ph3-OCFF-Cy-Ph3-F | 5.0 |
| 3-Cy-Ph3-OCFF-Cy-Ph3-F | 5.0 |
| 3-Cy-Ph3-O1-Cy-Ph3-F | 5.0 |
| total | 100.0 |
| Tni (° C.) | 76.3 |
| T-n (° C.) | −44.0 |
| Vth (volt) | 1.25 |
| Δε | 9.6 |
| Δn | 0.078 |
| η20° C. (mPa · s) | 12.3 |

Example 50

The resulting liquid crystal composition and the physical properties thereof are shown below.

TABLE 52

| | |
|---|---|
| 1d1-Cy-Cy-3 | 10.0 |
| 3-Cy-d-Cy-3 | 10.0 |
| 3-Pr-d-Cy-3 | 10.0 |
| 3-Cy-Ph-O2 | 5.0 |
| 3-Cy-Cy-Ph-1 | 5.0 |
| 3-Cy-Cy-CFFO-Ph3-F | 5.0 |
| 3-Cy-Ph1-Ph3-CFFO-Ph3-F | 5.0 |
| 3-Ph-Ph1-Ph3-CFFO-Ph3-F | 5.0 |
| 3-Pr-Ph-Ph3-OCFFF | 5.0 |
| 3-Cy-Ph-Ph3-F | 5.0 |
| 3-Pr-Cy-CFFO-Ph3-F | 5.0 |
| 3-Ph3-OCFF-Cy-Ph3-OCFFF | 5.0 |
| 3-Ph3-OCFF-Pr-Ph3-F | 5.0 |
| 3-Ph3-OCFF-Cy-Ph3-Ph3-F | 5.0 |
| 3-Ph3-OCFF-Cy-Ph3-CFFO-Ph3-F | 5.0 |
| 3-Ph3-CFFO-Ph3-OCFF-Cy-Ph3-F | 5.0 |
| 3-Cy-Ph3-OCFF-Cy-Ph3-F | 5.0 |
| total | 100.0 |
| Tni (° C.) | 74.0 |
| T-n (° C.) | −44.0 |
| Vth (volt) | 1.18 |
| Δε | 14.0 |
| Δn | 0.093 |
| η20° C. (mPa · s) | 15.7 |

Example 51

The resulting liquid crystal composition and the physical properties thereof are shown below.

TABLE 53

| | |
|---|---|
| 0d1-Cy-Cy-3 | 10.0 |
| 1d1-Cy-Cy-2 | 10.0 |
| 0d3-Cy-Cy-3 | 10.0 |
| 1d1-Cy-Cy-3 | 10.0 |
| 3-Cy-d-Cy-3 | 10.0 |
| 3-Cy-d-Cy-1d1 | 10.0 |
| 3-Pr-Cy-2 | 5.0 |
| 3-Pr-Cy-1d0 | 5.0 |
| 3-Pr-d-Cy-3d0 | 5.0 |
| 3-Ph-Ph1-Ph3-CFFO-Ph3-F | 5.0 |
| 3-Pr-Ph1-Ph3-CFFO-Ph3-F | 5.0 |
| 3-Ph3-OCFF-Cy-Ph3-Ph3-F | 5.0 |
| 3-Cy-Ph3-OCFF-Cy-Ph3-F | 5.0 |
| 3-Cy-Ph3-O1-Cy-Ph3-F | 5.0 |
| total | 100.0 |
| Tni (° C.) | 71.1 |
| T-n (° C.) | −39.0 |
| Vth (volt) | 1.61 |
| Δε | 6.9 |
| Δn | 0.070 |
| η20° C. (mPa · s) | 9.7 |

Example 52

The resulting liquid crystal composition and the physical properties thereof are shown below.

TABLE 54

| | |
|---|---|
| 0d1-Cy-Cy-3 | 10.0 |
| 1d1-Cy-Cy-2 | 10.0 |
| 0d3-Cy-Cy-3 | 10.0 |
| 1d1-Cy-Cy-3 | 10.0 |
| 3-Cy-d-Cy-1d1 | 10.0 |
| 3-Pr-d-Cy-3d0 | 10.0 |
| 3-Cy-Cy-Ph-1 | 5.0 |
| 3-Ph3-OCFF-Cy-Ph3-OCFFF | 5.0 |
| 3-Ph3-OCFF-Pr-Ph3-F | 5.0 |
| 3-Ph3-OCFF-Cy-Ph3-Ph3-F | 5.0 |
| 3-Ph3-OCFF-Cy-Ph3-CFFO-Ph3-F | 5.0 |
| 3-Ph3-CFFO-Ph3-OCFF-Cy-Ph3-F | 5.0 |
| 3-Cy-Ph3-OCFF-Cy-Ph3-F | 5.0 |
| 3-Cy-Ph3-O1-Cy-Ph3-F | 5.0 |
| total | 100.0 |
| Tni (° C.) | 72.4 |
| T-n (° C.) | −40.0 |
| Vth (volt) | 1.38 |
| Δε | 9.1 |
| Δn | 0.074 |
| η20° C. (mPa · s) | 9.4 |

Example 53

The resulting liquid crystal composition and the physical properties thereof are shown below.

TABLE 55

| | |
|---|---|
| 0d1-Cy-Cy-3 | 10.0 |
| 0d3-Cy-Cy-3 | 10.0 |
| 1d1-Cy-Cy-3 | 10.0 |
| 3-Pr-Cy-2 | 10.0 |
| 3-Cy-Cy-Ph-1 | 5.0 |
| 1-Ph-Ph1-Ph-3d0 | 5.0 |
| 3-Cy-Ph1-Ph3-CFFO-Ph3-F | 5.0 |
| 3-Ph-Ph1-Ph3-CFFO-Ph3-F | 5.0 |
| 3-Pr-Ph-Ph3-OCFFF | 5.0 |
| 3-Pr-Ph1-Ph3-CFFO-Ph3-F | 5.0 |
| 3-Ph3-O1-Cy-Ph-OCFFF | 5.0 |
| 3-Ph3-OCFF-Cy-Ph3-Ph3-F | 5.0 |
| 3-Ph3-OCFF-Cy-Ph3-CFFO-Ph3-F | 5.0 |
| 3-Ph3-CFFO-Ph3-OCFF-Cy-Ph3-F | 5.0 |
| 3-Cy-Ph3-OCFF-Cy-Ph3-F | 5.0 |
| 3-Cy-Ph3-O1-Cy-Ph3-F | 5.0 |
| total | 100.0 |
| Tni (° C.) | 76.3 |
| T-n (° C.) | −45.0 |
| Vth (volt) | 1.11 |
| Δε | 13.5 |
| Δn | 0.096 |
| η20° C. (mPa·s) | 16.4 |

Example 54

The resulting liquid crystal composition and the physical properties thereof are shown below.

TABLE 56

| | |
|---|---|
| 1d1-Cy-Cy-2 | 10.0 |
| 3-Cy-d-Cy-3 | 10.0 |
| 3-Cy-d-Cy-1d1 | 10.0 |
| 3-Pr-Cy-1d0 | 10.0 |
| 3-Pr-d-Cy-3d0 | 10.0 |
| 3-Cy-Cy-Ph-1 | 5.0 |
| 1-Ph-Ph1-Ph-3d0 | 5.0 |
| 3-Cy-Cy-CFFO-Ph3-F | 5.0 |
| 3-Cy-Ph-Ph3-F | 5.0 |
| 3-Pr-Cy-CFFO-Ph3-F | 5.0 |
| 3-Ph3-OCFF-Cy-Ph3-OCFFF | 5.0 |
| 3-Ph3-OCFF-Pr-Ph3-F | 5.0 |
| 3-Ph3-OCFF-Cy-Ph3-Ph3-F | 5.0 |
| 3-Cy-Ph3-OCFF-Cy-Ph3-F | 5.0 |
| 3-Cy-Ph3-O1-Cy-Ph3-F | 5.0 |
| total | 100.0 |
| Tni (° C.) | 77.5 |
| T-n (° C.) | −45.0 |
| Vth (volt) | 1.58 |
| Δε | 7.1 |
| Δn | 0.083 |
| η20° C. (mPa·s) | 10.6 |

Example 55

The resulting liquid crystal composition and the physical properties thereof are shown below.

TABLE 57

| | |
|---|---|
| 0d3-Cy-Cy-3 | 10.0 |
| 1d1-Cy-Cy-3 | 10.0 |
| 3-Cy-d-Cy-1d1 | 10.0 |
| 3-Pr-d-Cy-3d0 | 10.0 |

TABLE 57-continued

| | |
|---|---|
| 1-Ph-Ph1-Ph-3d0 | 5.0 |
| 3-Cy-Cy-CFFO-Ph3-F | 5.0 |
| 3-Cy-Ph1-Ph3-CFFO-Ph3-F | 5.0 |
| 3-Pr-Ph-Ph3-OCFFF | 5.0 |
| 3-Cy-Ph-Ph3-F | 5.0 |
| 3-Pr-Cy-CFFO-Ph3-F | 5.0 |
| 3-Pr-Ph1-Ph3-CFFO-Ph3-F | 5.0 |
| 3-Ph3-O1-Cy-Ph-OCFFF | 5.0 |
| 3-Ph3-OCFF-Cy-Ph3-OCFFF | 5.0 |
| 3-Ph3-OCFF-Pr-Ph3-F | 5.0 |
| 3-Ph3-OCFF-Cy-Ph3-CFFO-Ph3-F | 5.0 |
| 3-Ph3-CFFO-Ph3-OCFF-Cy-Ph3-F | 5.0 |
| total | 100.0 |
| Tni (° C.) | 71.2 |
| T-n (° C.) | −44.0 |
| Vth (volt) | 1.28 |
| Δε | 11.5 |
| Δn | 0.098 |
| η20° C. (mPa·s) | 13.4 |

Example 56

The resulting liquid crystal composition and the physical properties thereof are shown below.

TABLE 58

| | |
|---|---|
| 0d1-Cy-Cy-3 | 5.0 |
| 1d1-Cy-Cy-2 | 5.0 |
| 0d3-Cy-Cy-3 | 5.0 |
| 1d1-Cy-Cy-3 | 5.0 |
| 3-Cy-Cy-Ph-1 | 5.0 |
| 3-Cy-Cy-CFFO-Ph3-F | 5.0 |
| 3-Cy-Ph1-Ph3-CFFO-Ph3-F | 5.0 |
| 3-Ph-Ph1-Ph3-CFFO-Ph3-F | 5.0 |
| 3-Pr-Ph-Ph3-OCFFF | 5.0 |
| 3-Cy-Ph-Ph3-F | 5.0 |
| 3-Pr-Cy-CFFO-Ph3-F | 5.0 |
| 3-Pr-Ph1-Ph3-CFFO-Ph3-F | 5.0 |
| 3-Ph3-O1-Cy-Ph-OCFFF | 5.0 |
| 3-Ph3-OCFF-Cy-Ph3-OCFFF | 5.0 |
| 3-Ph3-OCFF-Pr-Ph3-F | 5.0 |
| 3-Ph3-OCFF-Cy-Ph3-Ph3-F | 5.0 |
| 3-Ph3-OCFF-Cy-Ph3-CFFO-Ph3-F | 5.0 |
| 3-Ph3-CFFO-Ph3-OCFF-Cy-Ph3-F | 5.0 |
| 3-Cy-Ph3-OCFF-Cy-Ph3-F | 5.0 |
| 3-Cy-Ph3-O1-Cy-Ph3-F | 5.0 |
| total | 100.0 |
| Tni (° C.) | 74.8 |
| T-n (° C.) | −48.0 |
| Vth (volt) | 1.01 |
| Δε | 16.9 |
| Δn | 0.097 |
| η20° C. (mPa·s) | 18.1 |

Example 57

The resulting liquid crystal composition and the physical properties thereof are shown below.

TABLE 59

| | |
|---|---|
| 0d1-Cy-Cy-3 | 10.0 |
| 1d1-Cy-Cy-2 | 10.0 |
| 3-Cy-d-Cy-3 | 10.0 |
| 3-Cy-d-Cy-1d1 | 10.0 |
| 3-Cy-Ph1-Ph3-CFFO-Ph3-F | 7.0 |
| 3-Ph-Ph1-Ph3-CFFO-Ph3-F | 8.0 |
| 3-Pr-Ph-Ph3-OCFFF | 5.0 |
| 3-Pr-Ph1-Ph3-CFFO-Ph3-F | 7.0 |
| 3-Ph3-OCFF-Pr-Ph3-F | 2.0 |

TABLE 59-continued

| | |
|---|---|
| 3-Ph3-OCFF-Cy-Ph3-Ph3-F | 8.0 |
| 3-Ph3-OCFF-Cy-Ph3-CFFO-Ph3-F | 8.0 |
| 3-Ph3-CFFO-Ph3-OCFF-Cy-Ph3-F | 8.0 |
| 3-Cy-Ph3-OCFF-Cy-Ph3-F | 5.0 |
| 3-Cy-Ph3-O1-Cy-Ph3-F | 2.0 |
| total | 100.0 |
| Tni (° C.) | 72.8 |
| T-n (° C.) | −41.0 |
| Vth (volt) | 0.97 |
| Δε | 18.5 |
| Δn | 0.098 |
| η20° C. (mPa · s) | 18.4 |

Example 58

The resulting liquid crystal composition and the physical properties thereof are shown below.

TABLE 60

| | |
|---|---|
| 0d1-Cy-Cy-3 | 10.0 |
| 1d1-Cy-Cy-2 | 10.0 |
| 1d1-Cy-Cy-3 | 12.0 |
| 3-Cy-d-Cy-3 | 10.0 |
| 3-Cy-d-Cy-1d1 | 13.0 |
| 3-Cy-Cy-Ph-1 | 5.0 |
| 3-Cy-Cy-CFFO-Ph3-F | 5.0 |
| 3-Ph-Ph1-Ph3-CFFO-Ph3-F | 5.0 |
| 3-Cy-Ph-Ph3-F | 5.0 |
| 3-Pr-Cy-CFFO-Ph3-F | 5.0 |
| 3-Ph3-OCFF-Cy-Ph3-OCFFF | 5.0 |
| 3-Ph3-OCFF-Cy-Ph3-Ph3-F | 5.0 |
| 3-Ph3-OCFF-Cy-Ph3-CFFO-Ph3-F | 5.0 |
| 3-Ph3-CFFO-Ph3-OCFF-Cy-Ph3-F | 5.0 |
| total | 100.0 |
| Tni (° C.) | 73.0 |
| T-n (° C.) | −48.0 |
| Vth (volt) | 1.24 |
| Δε | 10.0 |
| Δn | 0.080 |
| η20° C. (mPa · s) | 11.6 |

Example 59

The resulting liquid crystal composition and the physical properties thereof are shown below.

TABLE 61

| | |
|---|---|
| Mix-B | 35.0 |
| 3-Ph3-CFFO-Pr-Ph3-F | 5.0 |
| 3-Ph3-CFFO-Oc-Ph3-F | 5.0 |
| 3-Ph3-O1-Cy-Ph3-Ph3-OCFFF | 5.0 |
| 3-Ph3-O1-Cy-Ph3-Ph3-OCH=CFF | 5.0 |
| 3-Ph3-O1-Oc-Ph-Ph3-F | 5.0 |
| 3-Ph3-CFFO-Ph3-OCFF-Cy-Ph3-F | 5.0 |
| 3-Cy-Ph3-CFFO-Pr-Ph3-F | 5.0 |
| 3-Pr-Ph3-O1-Cy-Ph3-F | 5.0 |
| 3-Ph3-O1-Cy-Ph3-Ph3-F | 5.0 |
| 3-Ph3-O1-Pr-Ph3-Ph3-F | 5.0 |
| 3-Ph3-O1-Pr-Ph3-Ph-OCFFF | 5.0 |
| 3-Ph3-OCFF-Cy-Ph3-F | 5.0 |
| 3-Cy-Ph3-OCFF-Cy-Ph3-F | 5.0 |
| total | 100.0 |
| Tni (° C.) | 75.9 |
| T-n (° C.) | −46.0 |
| Vth (volt) | 0.98 |

TABLE 61-continued

| | |
|---|---|
| Δε | 18.9 |
| Δn | 0.086 |
| η20° C. (mPa · s) | 19.5 |

Example 60

The resulting liquid crystal composition and the physical properties thereof are shown below.

TABLE 62

| | |
|---|---|
| Mix-A | 60.0 |
| 3-Ph3-O1-Cy-Ph3-Ph3-OCFFF | 5.0 |
| 3-Ph3-O1-Cy-Ph3-Ph3-OCH=CFF | 5.0 |
| 3-Ph3-O1-Oc-Ph-Ph3-F | 5.0 |
| 3-Ph3-OCFF-Cy-Ph3-Ph3-OCH=FF | 5.0 |
| 3-Ph3-O1-Cy-Ph3-Ph3-F | 5.0 |
| 3-Ph3-O1-Cy-Ph3-Ph-OCFFF | 5.0 |
| 3-Ph3-OCFF-Cy-Ph3-Ph-OCFFF | 5.0 |
| 3-Cy-Ph1-Ph3-O1-Ph3-OCFFF | 5.0 |
| total | 100.0 |
| Tni (° C.) | 95.9 |
| T-n (° C.) | −40.0 |
| Vth (volt) | 1.30 |
| Δε | 12.7 |
| Δn | 0.115 |
| η20° C. (mPa · s) | 18.9 |

Example 61

The resulting liquid crystal composition and the physical properties thereof are shown below.

TABLE 63

| | |
|---|---|
| Mix-A | 60.0 |
| 3-Ph3-O1-Cy-Ph3-F | 5.0 |
| 3-Ph3-O1-Cy-Ph3-Ph3-OCH=CFF | 5.0 |
| 3-Ph3-O1-Oc-Ph-Ph3-F | 5.0 |
| 3-Ph3-CFFO-Ph3-OCFF-Cy-Ph3-F | 5.0 |
| 3-Ph3-O1-Cy-Ph3-Ph3-F | 5.0 |
| 3-Ph3-O1-Pr-Ph3-Ph3-F | 5.0 |
| 3-Ph3-O1-Pr-Ph3-Ph-OCFFF | 5.0 |
| 3-Cy-Ph1-Ph3-O1-Ph3-OCFFF | 5.0 |
| total | 100.0 |
| Tni (° C.) | 80.7 |
| T-n (° C.) | −43.0 |
| Vth (volt) | 1.26 |
| Δε | 12.6 |
| Δn | 0.109 |
| η20° C. (mPa · s) | 17.7 |

Example 62

The resulting liquid crystal composition and the physical properties thereof are shown below.

TABLE 64

| | |
|---|---|
| Mix-A | 50.0 |
| 3-Ph3-O1-Cy-Ph-OCFFF | 10.0 |
| 3-Ph3-O1-Oc-Ph1-Ph3-F | 5.0 |
| 3-Ph3-OCFF-Cy-Ph3-Ph3-F | 5.0 |
| 3-Ph3-OCFF-Cy-Ph3-CFFO-Ph3-F | 5.0 |

85

TABLE 64-continued

| | |
|---|---|
| 3-Ph3-OCFF-Pr-Ph3-CFFO-Ph3-F | 5.0 |
| 3-Ph3-OCFF-Cy-Ph3-Ph3-OCFFF | 5.0 |
| 3-Pr-Ph3-OCFF-Cy-Ph3-F | 5.0 |
| 3-Pr-Ph3-O1-Cy-Ph3-F | 5.0 |
| 3-Ph3-O1-Cy-Np3-F | 5.0 |
| total | 100.0 |
| Tni (° C.) | 75.2 |
| T-n (° C.) | −42.0 |
| Vth (volt) | 1.15 |
| Δε | 13.6 |
| Δn | 0.105 |
| η20° C. (mPa · s) | 15.5 |

Example 63

The resulting liquid crystal composition and the physical properties thereof are shown below.

TABLE 65

| | |
|---|---|
| Mix-A | 45.0 |
| 3-Ph-Ph1-Ph3-F | 5.0 |
| 3-Pr-Ph1-Ph3-CFFO-Ph3-F | 5.0 |
| 3-Ph3-OCFF-Cy-Ph3-OCFFF | 5.0 |
| 3-Ph3-O1-Oc-Ph3-Ph3-F | 7.0 |
| 3-Ph3-OCFF-Cy-Ph3-Ph3-F | 8.0 |
| 3-Ph3-OCFF-Cy-Ph3-CFFO-Ph3-F | 5.0 |
| 3-Ph3-OCFF-Pr-Ph3-OFFO-Ph3-F | 5.0 |
| 3-Ph3-OCFF-Cy-Ph3-Ph3-OCFFF | 5.0 |
| 3-Ph-Ph3-OCFF-Cy-Ph3-F | 5.0 |
| 3-Pr-Ph3-OCFF-Cy-Ph3-F | 5.0 |
| total | 100.0 |
| Tni (° C.) | 81.5 |
| T-n (° C.) | −41.0 |
| Vth (volt) | 1.04 |
| Δε | 17.6 |
| Δn | 0.114 |
| η20° C. (mPa · s) | 18.4 |

Example 64

The resulting liquid crystal composition and the physical properties thereof are shown below.

TABLE 66

| | |
|---|---|
| Mix-A | 60.0 |
| 3-Ph3-O1-Cy-Ph3-Ph3-OCFFF | 5.0 |
| 3-Ph1-O1-Cy-Ph3-Ph3-OCH=CFF | 5.0 |
| 3-Ph3-CFFO-Oc-Ph-Ph3-F | 5.0 |
| 3-Ph3-OCFF-Cy-Ph3-Ph3-OCH=FF | 5.0 |
| 3-Ph3-O1-Cy-Ph3-Ph3-F | 5.0 |
| 3-Ph3-O1-Cy-Ph3-Ph-OCFFF | 5.0 |
| 3-Ph3-OCFF-Cy-Ph3-Ph-OCFFF | 5.0 |
| 3-Cy-Ph1-Ph3-O1-Ph3-OCFFF | 5.0 |
| total | 100.0 |
| Tni (° C.) | 95.9 |
| T-n (° C.) | −40.0 |
| Vth (volt) | 1.30 |
| Δε | 12.7 |
| Δn | 0.115 |
| η20° C. (mPa · s) | 18.9 |

Example 65

The resulting liquid crystal composition and the physical properties thereof are shown below.

86

TABLE 67

| | |
|---|---|
| Mix-A | 60.0 |
| 3-Ph3-O1-Cy-Ph3-F | 5.0 |
| 3-Ph3-O1-Cy-Ph3-Ph3-OCH=CFF | 5.0 |
| 3-Ph3-CFFO-Oc-Ph1-Ph3-F | 5.0 |
| 3-Ph3-CFFO-Ph3-OCFF-Cy-Ph3-F | 5.0 |
| 3-Ph3-O1-Cy-Ph3-Ph3-F | 5.0 |
| 3-Ph3-O1-Pr-Ph3-Ph3-F | 5.0 |
| 3-Ph3-O1-Pr-Ph3-Ph-OCFFF | 5.0 |
| 3-Cy-Ph1-Ph3-O1-Ph3-OCFFF | 5.0 |
| total | 100.0 |
| Tni (° C.) | 80.7 |
| T-n (° C.) | −43.0 |
| Vth (volt) | 1.26 |
| Δε | 12.6 |
| Δn | 0.109 |
| η20° C. (mPa · s) | 17.7 |

Example 66

The physical property $\gamma_1$ of the liquid crystal compositions according to the present invention at 20° C. is shown below. These results show that the $\gamma_1$ of the liquid crystal compositions according to the present invention was relative low for the magnitude of the dielectric anisotropy (Δε), demonstrating the superiority of the combinations according to the present invention.

$\gamma_1$ of Example 9: 46 mPa·s
$\gamma_1$ of Example 11: 53 mPa·s
$\gamma_1$ of Example 20: 87 mPa·s
$\gamma_1$ of Example 28: 81 mPa·s
$\gamma_1$ of Example 34: 50 mPa·s
$\gamma_1$ of Example 44: 47 mPa·s
$\gamma_1$ of Example 47: 58 mPa·s
$\gamma_1$ of Example 56: 84 mPa·s

Examples 67 and 68

Empty IPS cells were fabricated using a first substrate having a pair of transparent electrodes forming a comb-shaped electrode configuration and a second substrate having no electrode configuration. Vertical alignment films were formed on both substrates, and the gap distance therebetween was 4.0 microns. Liquid crystal display devices were fabricated by injecting the liquid crystal compositions of Examples 46 and 50 into the empty cells and were tested for their electro-optical characteristics.

The polymerizable compound represented by formula (PC-1)-3-1 was added to the liquid crystal compositions of the same examples and was homogeneously dissolved to obtain polymerizable liquid crystal compositions.

[Chem. 41]

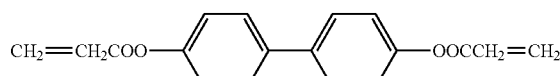

The resulting polymerizable liquid crystal compositions were injected into empty IPS cells fabricated as described above. The resulting liquid crystal cells were irradiated with UV radiation from a high-pressure mercury lamp through a filter capable of blocking UV radiation at 300 nm or less while applying a rectangular wave of 1.8 V at a frequency of 1 KHz. The polymerizable compound in the polymerizable liquid crystal compositions was polymerized by performing irradiation for 600 seconds while adjusting the irradiation intensity at the cell surfaces to 20 mW/cm² to obtain vertical-alignment liquid crystal display devices. These display devices were tested for their electro-optical characteristics. The results are shown in the following table.

TABLE 68

|  | Ex-46 | | Ex-50 | |
| --- | --- | --- | --- | --- |
| LC monomer | — IPS | 0.5% PSA-IPS | — IPS | 1.0% PSA-IPS |
| Vth | 1.20 | 1.22 | 1.22 | 1.25 |
| τ on | 6.5 | 4.8 | 6.5 | 4.9 |
| τ off | 15.6 | 5.2 | 16.3 | 5.4 |

The resulting liquid crystal display devices were much faster than those fabricated using liquid crystal compositions alone.

The invention claimed is:

1. A liquid crystal composition having a positive dielectric anisotropy, the liquid crystal composition comprising at least one compound represented by general formula (LC0):

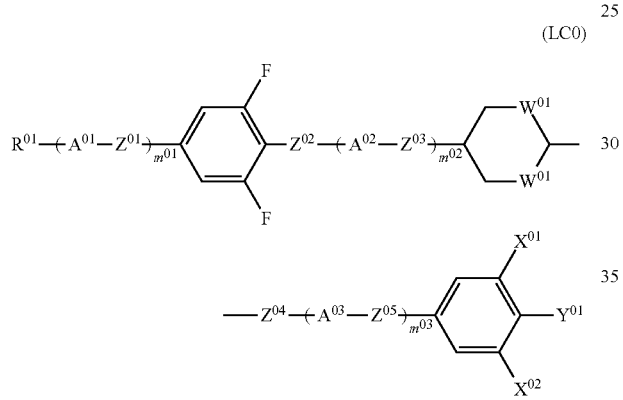
(LC0)

wherein
  $R^{01}$ is an alkyl group of 1 to 15 carbon atoms, wherein at least one —CH$_2$— of the alkyl group is optionally replaced by —O—, —CH=CH—, —CO—, —COO—, —COO—, —CF$_2$O— or —OCF$_2$— such that no oxygen atoms are directly adjacent to each other, and at least one hydrogen atom of the alkyl group is optionally replaced by halogen;
  $A^{01}$ to $A^{03}$ are each independently any of the following structures:

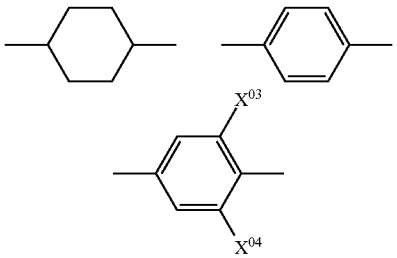

wherein at least one —CH$_2$— of the cyclohexane ring is optionally replaced by —O— such that no oxygen atoms are directly adjacent to each other, at least one —CH= of each benzene ring is optionally replaced by —N= such that no nitrogen atoms are directly adjacent to each other, and $X^{03}$ and $X^{04}$ are each independently —H, —Cl, —F, —CF$_3$, or —OCF$_3$;
  $X^{01}$ and $X^{02}$ are each independently hydrogen or fluorine;
  $Y^{01}$ is —Cl, —F, —OCHF$_2$, —CF$_3$, —OCF$_3$, or a fluorinated alkyl, alkoxy, alkenyl, or alkenyloxy group of 2 to 5 carbon atoms;
  $Z^{01}$ to $Z^{05}$ are each independently a single bond, —CH=CH—, —CH$_2$CH$_2$—, —(CH$_2$)$_4$—, —OCH$_2$—, —CH$_2$O—, —OCF$_2$—, or —CF$_2$O—, wherein at least one of $Z^{01}$ to $Z^{05}$ present is —OCH$_2$—, —OCF$_2$—, or —CF$_2$O—;
  $W^{01}$ and $W^{02}$ are each independently —CH$_2$— or —O—; and
  $m^{01}$ to $m^{03}$ are each independently an integer of 0 to 2, $m^{01}+m^{02}+m^{03}$ is 0, 1, or 2, and a plurality of $A^{01}$, $A^{02}$, $A^{03}$, $Z^{01}$, $Z^{03}$, and/or $Z^{05}$, if present, may be the same or different.

2. The liquid crystal composition according to claim 1, wherein the compound represented by general formula (LC0) is a compound represented by any of general formulas (LC0-1) to (LC0-59) and (LC0-68) to (LC0-74):

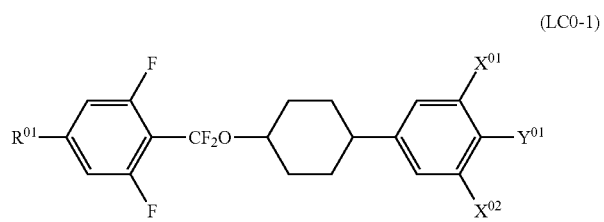
(LC0-1)

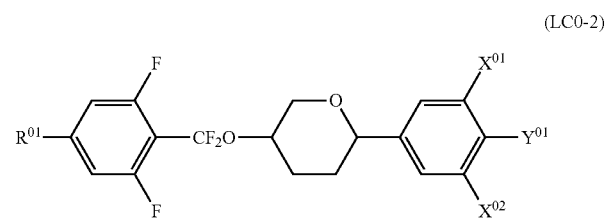
(LC0-2)

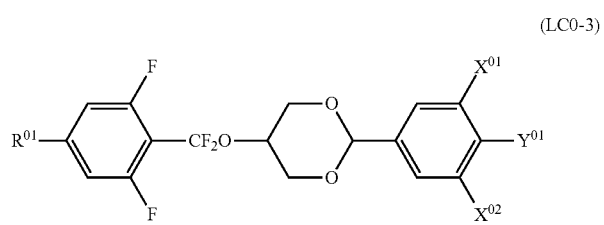
(LC0-3)

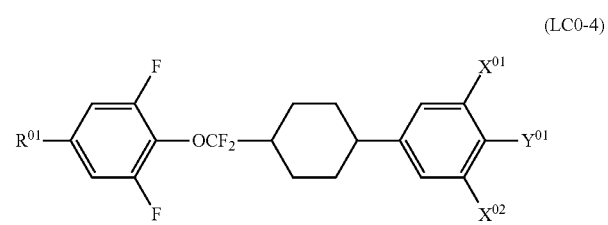
(LC0-4)

(LC0-5) 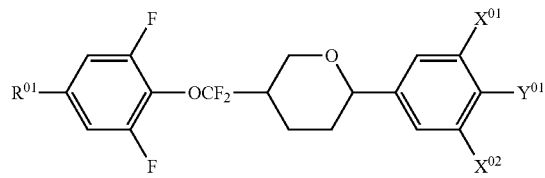
(LC0-6) 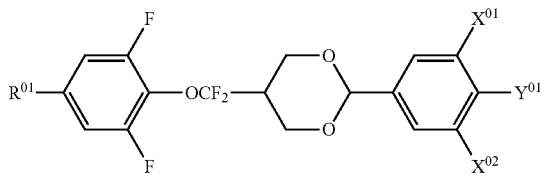
(LC0-7) 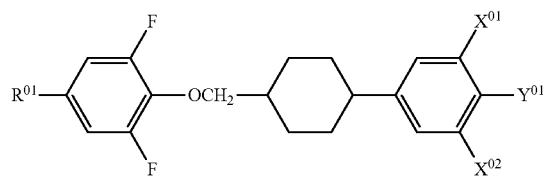
(LC0-8) 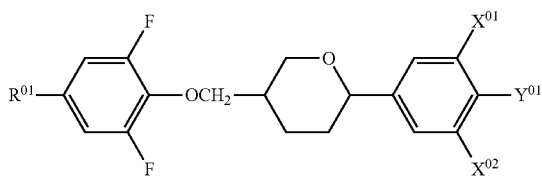
(LC0-9) 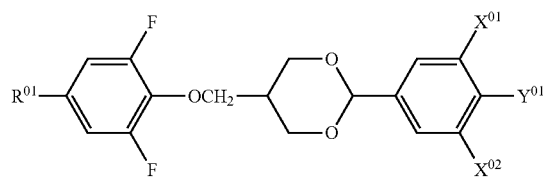
(LC0-10) 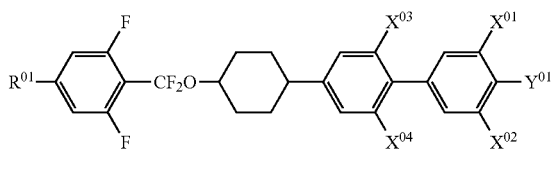
(LC0-11) 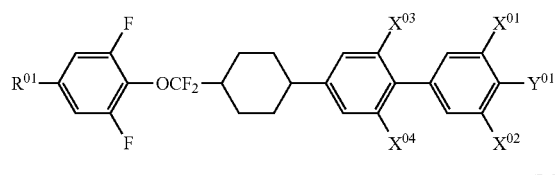
(LC0-12) 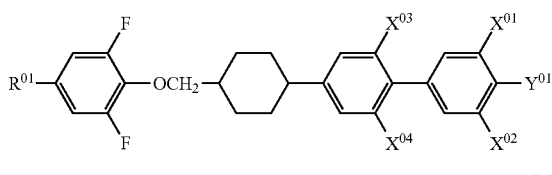
(LC0-13) 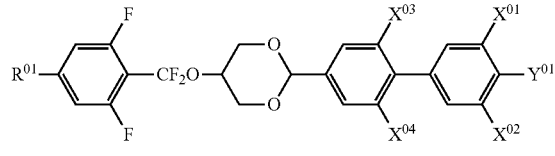
(LC0-14) 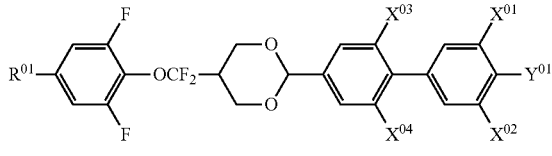
(LC0-15) 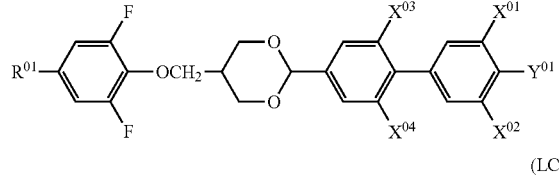
(LC0-16) 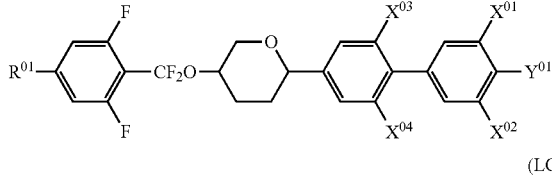
(LC0-17) 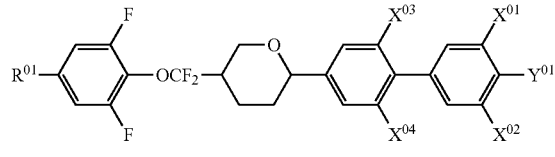
(LC0-18) 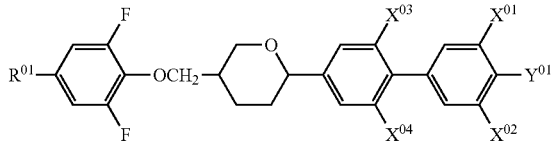
(LC0-19) 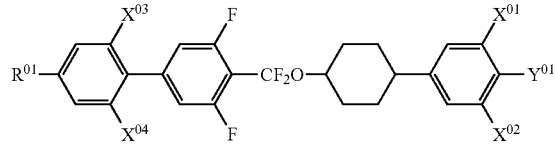
(LC0-20) 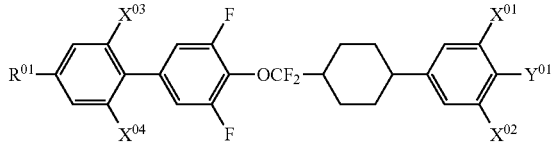

(LC0-21) 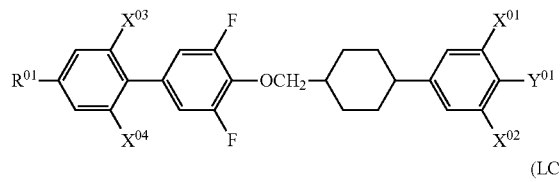
(LC0-22) 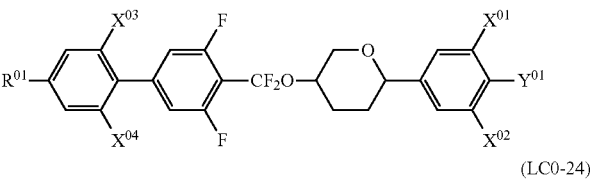
(LC0-23) 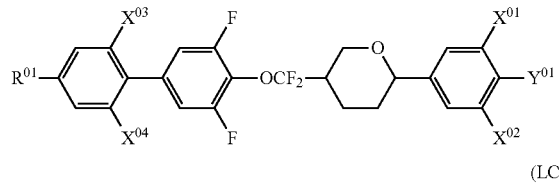
(LC0-24) 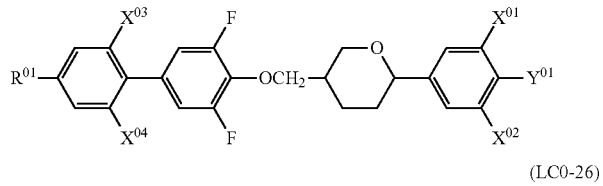
(LC0-25) 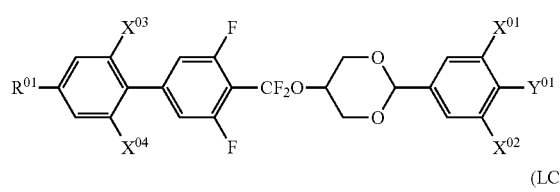
(LC0-26) 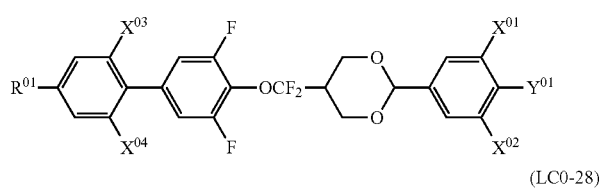
(LC0-27) 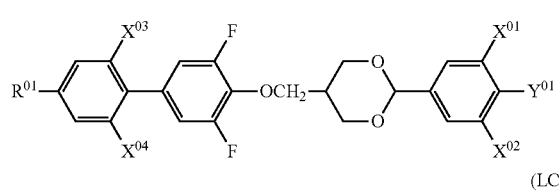
(LC0-28) 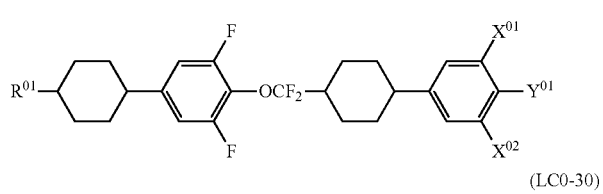
(LC0-29) 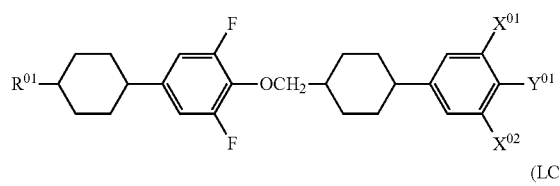
(LC0-30) 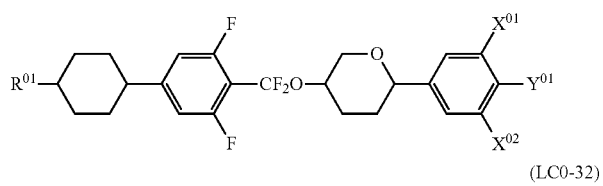
(LC0-31) 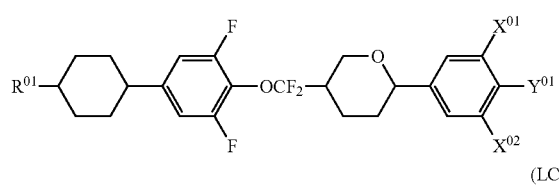
(LC0-32) 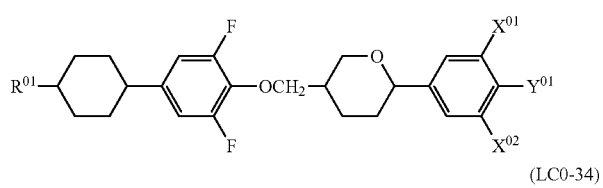
(LC0-33) 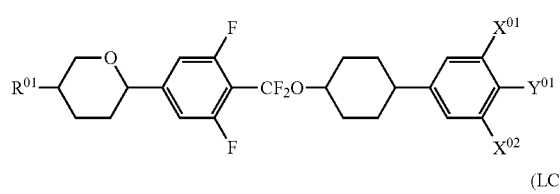
(LC0-34) 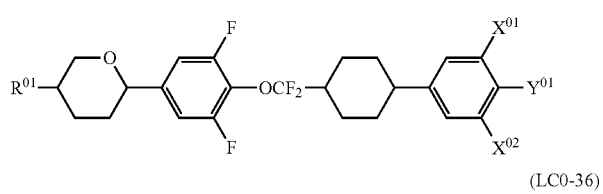
(LC0-35) 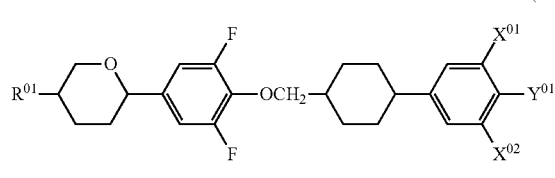
(LC0-36) 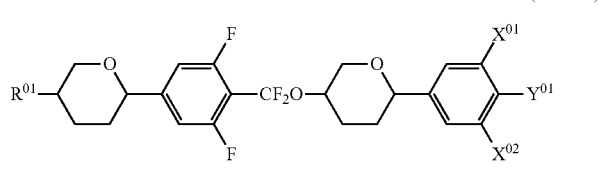
(LC0-37) 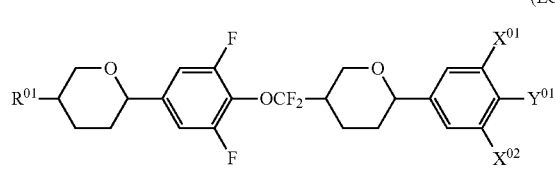

-continued
(LC0-39) 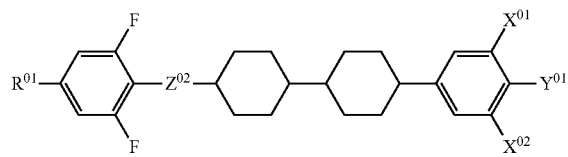
(LC0-40) 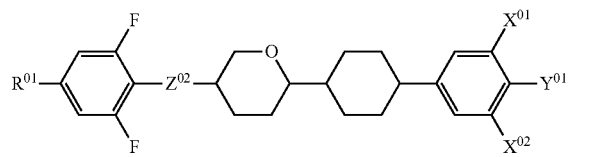
(LC0-41) 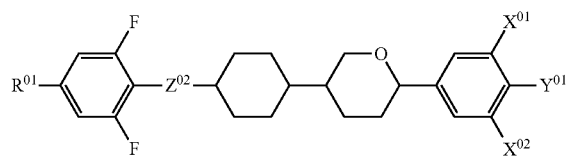
(LC0-42) 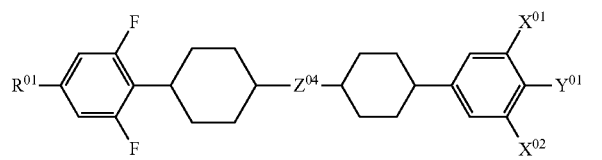
(LC0-43) 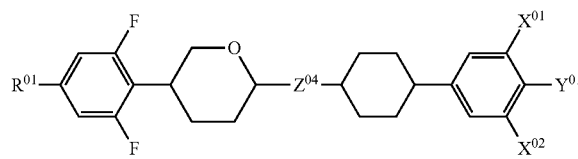
(LC0-44) 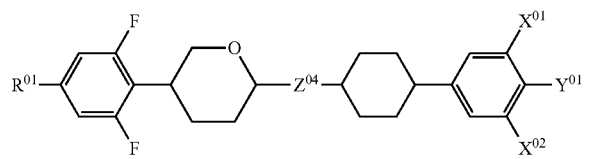
(LC0-45) 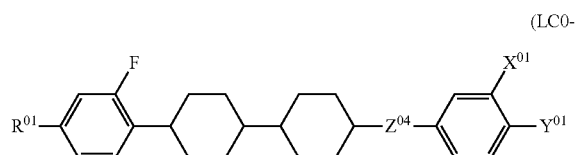
(LC0-46) 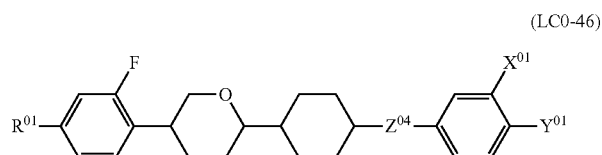
(LC0-47) 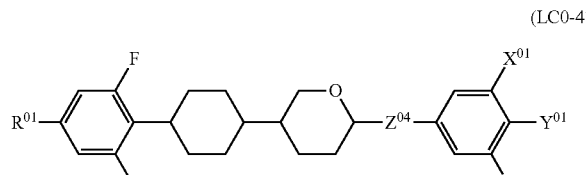
(LC0-48) 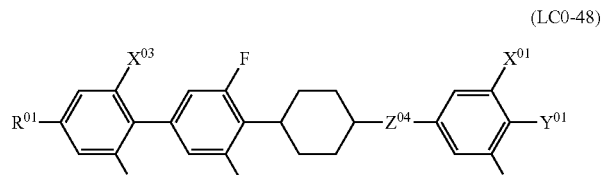
(LC0-49) 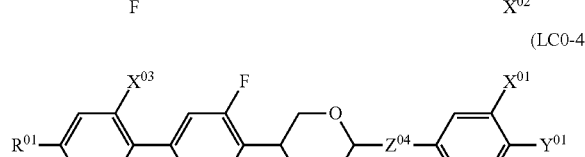
(LC0-50) 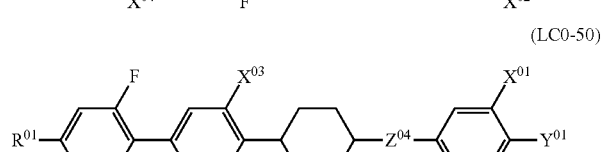
(LC0-51) 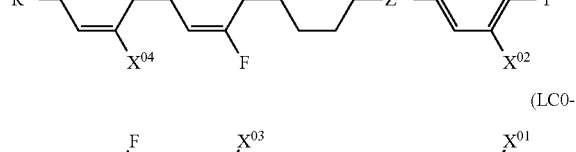
(LC0-52) 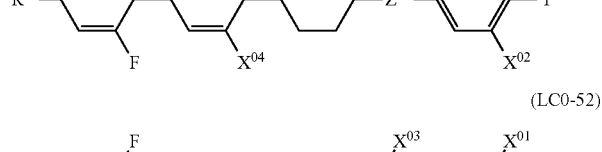
(LC0-53) 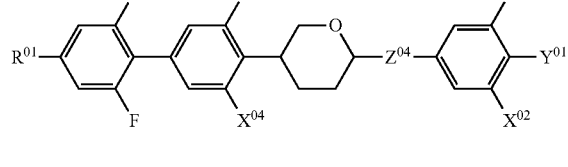
(LC0-54) 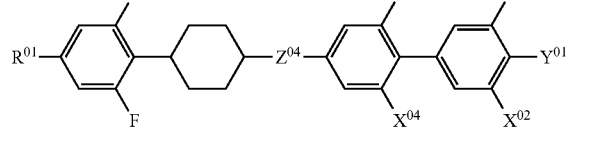

-continued
(LC0-55)
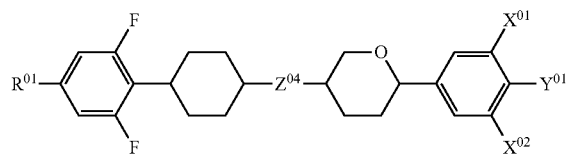
(LC0-56)
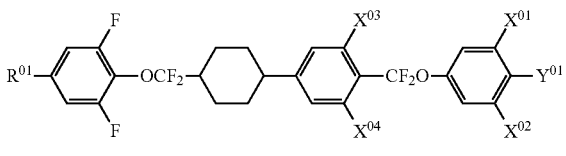
(LC0-57)
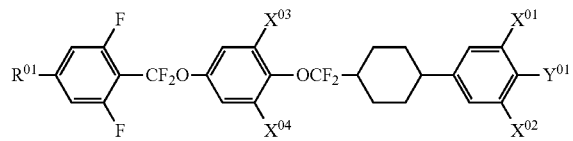
(LC0-58)
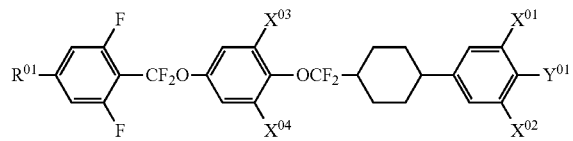
(LC0-59)
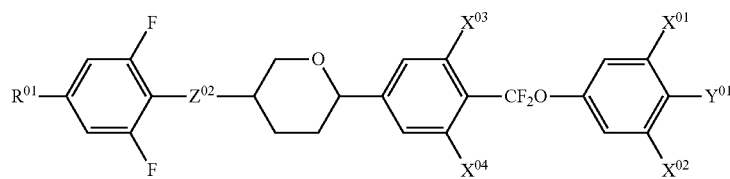
(LC0-68)
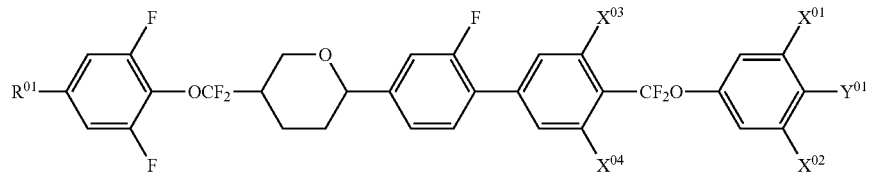
(LC0-70)
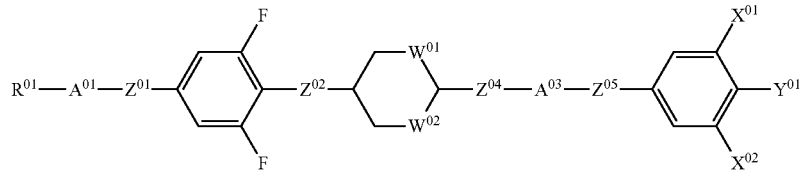
(LC0-71)
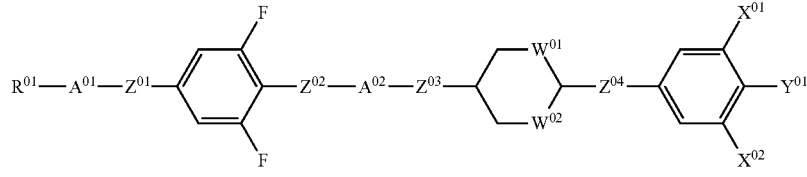
(LC0-72)
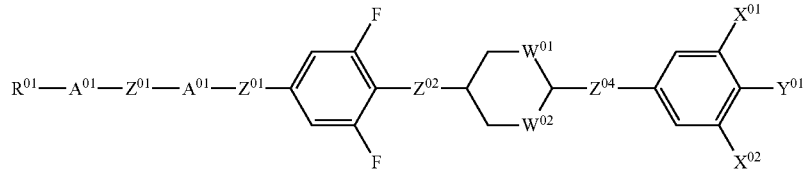
(LC0-74)
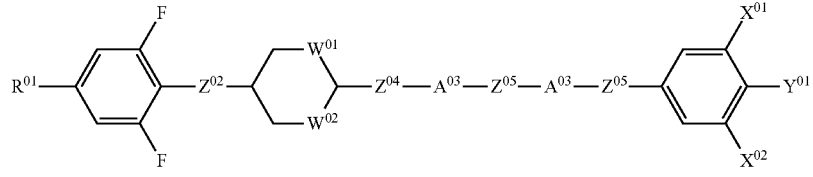

-continued

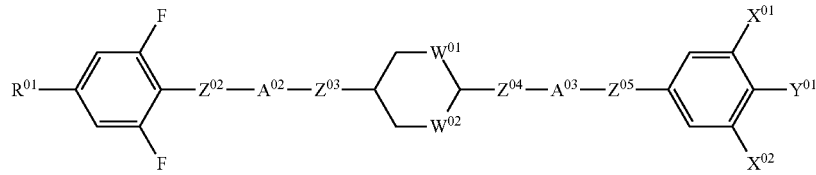
(LC0-69)

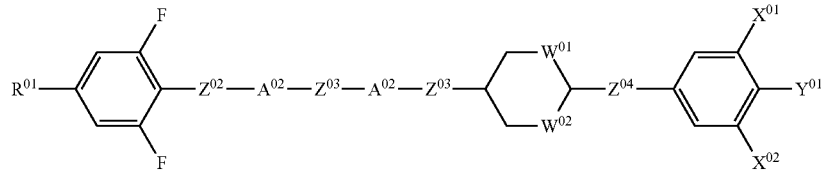
(LC0-73)

wherein $R^{01}$, $A^{01}$ to $A^{03}$, $Z^{01}$ to $Z^{05}$, $X^{01}$ to $X^{04}$, $W^{01}$, $X^{02}$, and $Y^{01}$ are as defined in claim 1.

3. The liquid crystal composition according to claim 2, wherein the liquid crystal composition comprising the compound represented by general formula (LC0) satisfies at least one of the following conditions:

comprising a compound represented by any of general formulas (LC0-2) to (LC0-9) in an amount of at most 40% by mass;

comprising a compound represented by any of general formulas (LC0-10) to (LC0-18) in an amount of at most 60% by mass;

comprising a compound represented by any of general formulas (LC0-28) to (LC0-38) in an amount of at most 60% by mass;

comprising a compound represented by any of general formulas (LC0-48) to (LC0-51) in an amount of at most 30% by mass;

comprising a compound represented by any of general formulas (LC0-52) and (LC0-53) in an amount of at most 40% by mass;

comprising a compound represented by any of general formulas (LC0-56) to (LC0-59) in an amount of at most 50% by mass;

comprising a compound represented by any of general formulas (LC0-60) to (LC0-67) in an amount of at most 20% by mass; and comprising a compound represented by any of general formulas (LC0-68) to (LC0-74) in an amount of at most 15% by mass.

4. The liquid crystal composition according to claim 2, wherein the compound represented by general formula (LC0) is a compound represented by any of general formulas (LC0-2) to (LC0-5), (LC0-7), (LC0-11) to (LC0-15), (LC0-17), (LC0-18), (LC0-20), (LC0-28) to (LC0-30), (LC0-34), (LC0-35), (LC0-39), (LC0-41), (LC0-45), (LC0-46), (LC0-56) to (LC0-61), (LC0-68), and (LC0-74).

5. The liquid crystal composition according to claim 1, wherein the compound represented by general formula (LC0) is any of the following compounds:

a compound wherein $Z^{01}$ is present and is —OCH$_2$—, —OCF$_2$—, or —CF$_2$O—;

a compound wherein $Z^{02}$ is —OCH$_2$—, —OCF$_2$—, or —CF$_2$O—;

a compound wherein $Z^{03}$ is present and is —OCH$_2$—, —OCF$_2$—, or —CF$_2$O—;

a compound wherein $Z^{04}$ is —OCH$_2$—, —OCF$_2$—, or —CF$_2$O—;

a compound wherein $Z^{05}$ is present and is —OCH$_2$—, —OCF$_2$—, or —CF$_2$O—;

a compound wherein both $W^{01}$ and $W^{02}$ are —CH$_2$—;
a compound wherein one of $W^{01}$ and $W^{02}$ is —O—;
a compound wherein both $W^{01}$ and $W^{02}$ are —O—;
a compound wherein $m^{01}+m^{02}+m^{03}$ is 0;
a compound wherein $m^{01}$ is 0, $m^{02}$ is 0, and $m^{03}$ is 1;
a compound wherein $m^{01}$ is 0, $m^{02}$ is 1, and $m^{03}$ is 0;
a compound wherein $m^{01}$ is 1, $m^{02}$ is 0, and $m^{03}$ is 0;
a compound wherein $m^{01}$ is 1, $m^{02}$ is 0, and $m^{03}$ is 1;
a compound wherein $m^{01}$ is 1, $m^{02}$ is 1, and $m^{03}$ is 0;
a compound wherein $m^{01}$ is 0, $m^{02}$ is 1, and $m^{03}$ is 1;
a compound wherein $m^{01}$ is 2, one $Z^{01}$ is —OCH$_2$—, —OCF$_2$—, or —CF$_2$O—, and another $Z^{01}$ is a single bond;
a compound wherein $m^{02}$ is 1 or 2, one of $Z^{02}$ and $Z^{03}$ is —OCH$_2$—, —OCF$_2$—, or —CF$_2$O—, and the remainder is a single bond; and
a compound wherein $m^{03}$ is 1 or 2, one of $Z^{04}$ and $Z^{05}$ is —OCH$_2$—, —OCF$_2$—, or —CF$_2$O—, and the remainder is a single bond.

6. The liquid crystal composition according to claim 1, further comprising at least one compound selected from the group consisting of compounds represented by general formulas (LC1) to (LC5):

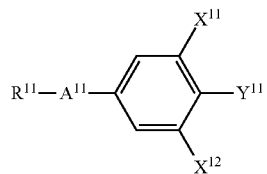
(LC1)

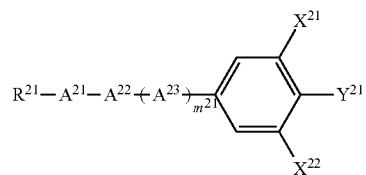
(OC2)

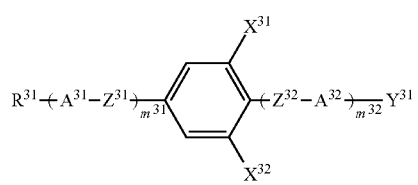
(OC3)

-continued

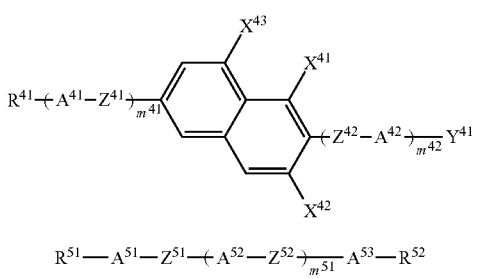
(LC4)

$$R^{51}-A^{51}-Z^{51}+\!\!\!\left(A^{52}-Z^{52}\right)_{\overline{m51}}A^{53}-R^{52} \quad (LC5)$$

wherein $R^{11}$ to $R^{41}$ are each independently an alkyl group of 1 to 15 carbon atoms, wherein at least one —$CH_2$— of the alkyl group is optionally replaced by —O—, —CH=CH—, —CO—, —OCO—, —COO—, —C≡C—, —$CF_2O$—, or —$OCF_2$— such that no oxygen atoms are directly adjacent to each other, and at least one hydrogen atom of the alkyl group is optionally replaced by halogen; $R^{51}$ and $R^{52}$ are each independently an alkyl group of 1 to 15 carbon atoms, wherein at least one —$CH_2$— of the alkyl group is optionally replaced by —O—, —CH=CH—, —CO—, —COO—, —COO—, or —C≡C— such that no oxygen atoms are directly adjacent to each other; if $A^{51}$ or $A^{53}$, described later, is a cyclohexane ring, $R^{51}$ or $R^{52}$ may be —$OCF_3$, —$CF_3$, —OCF=$CF_2$, or —OCH=$CF_2$; $A^{11}$ to $A^{42}$ are each independently any of the following structures:

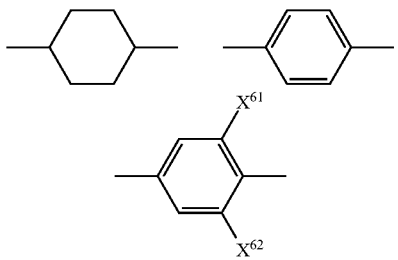

wherein at least one —$CH_2$— of the cyclohexane ring is optionally replaced by —O— such that no oxygen atoms are directly adjacent to each other, at least one —CH= of each benzene ring is optionally replaced by —N= such that no nitrogen atoms are directly adjacent to each other, and $X^{61}$ and $X^{62}$ are each independently —H, —Cl, —F, —$CF_3$, or —$OCF_3$; $A^{51}$ to $A^{53}$ are each independently any of the following structures:

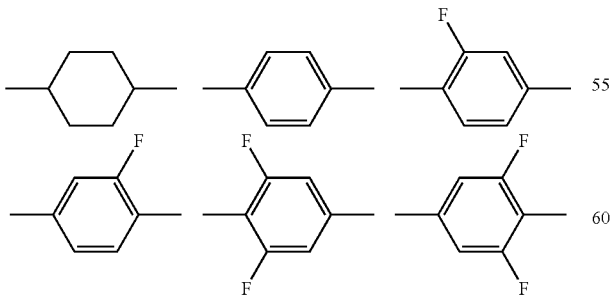

wherein at least one —$CH_2CH_2$— of the cyclohexane ring is optionally replaced by —CH=CH—, —$CF_2O$—, or —$OCF_2$—, and at least one —CH= of each benzene ring is optionally replaced by —N= such that no nitrogen atoms are directly adjacent to each other); $X^{11}$ to $X^{43}$ are each independently —H, —Cl, —F, —$CF_3$, or —$OCF_3$; $Y^{11}$ to $Y^{41}$ are —Cl, —F, —$CF_3$, —$OCF_3$, —$CF_2CF_3$, —$CHFCF_3$, —$OCF_2CF_3$, —$OCHFCF_3$, or —OCF=$CF_2$; $Z^{31}$ to $Z^{42}$ are each independently a single bond, —CH=CH—, —C≡C—, —$CH_2CH_2$—, —$(CH_2)_4$—, —$OCH_2$—, —$CH_2O$—, —$OCF_2$—, or —$CF_2O$—, wherein at least one of $Z^{31}$ and $Z^{32}$ present is not a single bond; $Z^{51}$ and $Z^{52}$ are each independently a single bond, —CH=CH—, —C≡C—, —$CH_2CH_2$—, —$(CH_2)_4$—, —$OCH_2$—, —$CH_2O$—, —$OCF_2$—, or —$CF_2O$—; $m^{11}$ to $m^{51}$ are each independently an integer of 0 to 3; $m^{31}+m^{32}$ and $m^{41}+m^{42}$ are each independently 1, 2, 3, or 4; and a plurality of $A^{23}$, $A^{31}$, $A^{32}$, $A^{41}$, $A^{42}$, $A^{52}$, $Z^{31}$, $Z^{32}$, $Z^{41}$, $Z^{42}$, and/or $Z^{52}$, if present, may be the same or different, with the proviso that compounds represented by general formula (LC0) are excluded.

7. The liquid crystal composition according to claim 6, wherein the liquid crystal composition comprises at least one compound represented by general formula (LC0) wherein $R^{01}$ is an alkyl group of 1 to 5 carbon atoms or an alkenyl group of 2 to 5 carbon atoms and $Y^{01}$ is —Cl, —F, —$OCHF_2$, —$CF_3$, —$OCF_3$, —$CF_2CF_3$, —$CHFCF_3$, —$OCF_2CF_3$, —$OCHFCF_3$, —OCF=$CF_2$, or —OCH=$CF_2$ in a total amount of at most 70% by mass.

8. The liquid crystal composition according to claim 6, wherein the liquid crystal composition comprises at least one compound represented by general formula (LC0) and satisfies at least one of the following conditions:

comprising a compound represented by general formula (LC1) in an amount of at most 20% by mass;

comprising a compound represented by general formula (LC2) in an amount of at most 40% by mass;

comprising a compound represented by general formula (LC3) in an amount of at most 50% by mass;

comprising a compound represented by general formula (LC4) in an amount of at most 60% by mass; and comprising a compound represented by general formula (LC5) in an amount of at most 75% by mass.

9. The liquid crystal composition according to claim 6, wherein the compound represented by general formula (LC4) is a compound selected from the group consisting of compounds represented by general formulas (LC4-1) to (LC4-32):

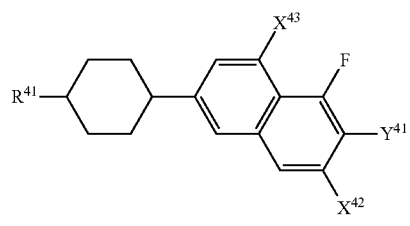
(LC-4-1)

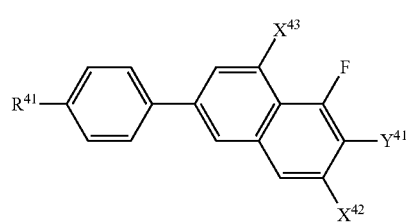
(LC-4-2)

(LC-4-3)
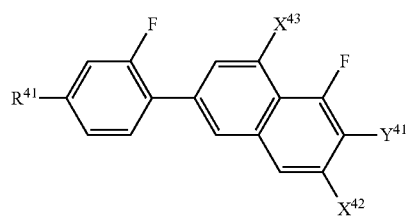
(LC-4-4)
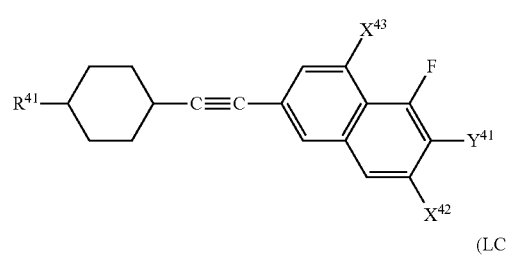
(LC-4-5)
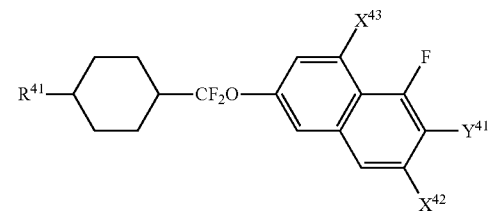
(LC-4-6)
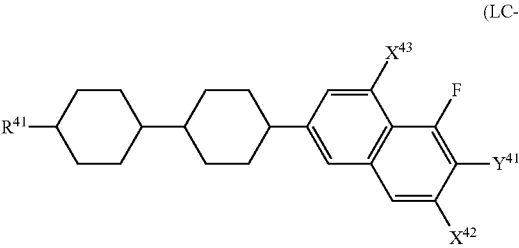
(LC-4-7)
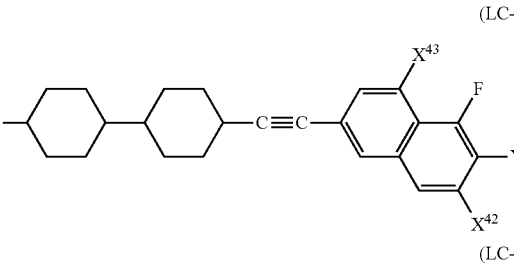
(LC-4-8)
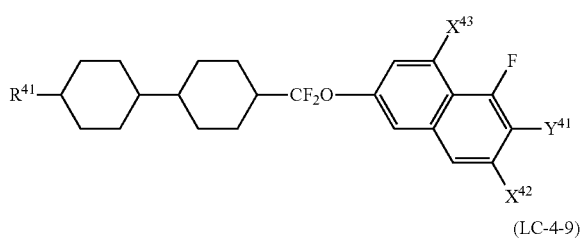
(LC-4-9)
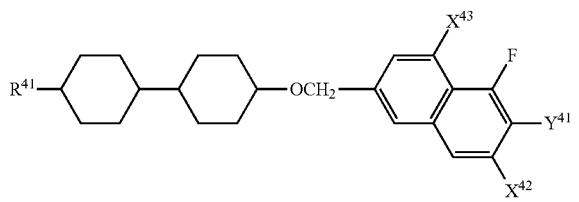
(LC-4-10)
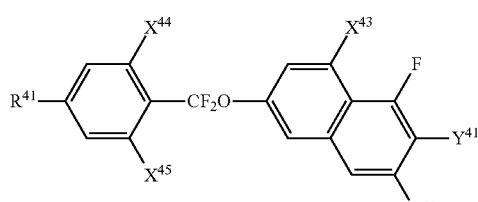
(LC-4-11)
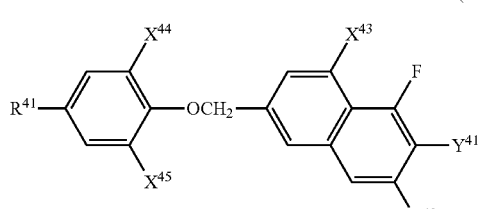
(LC-4-12)
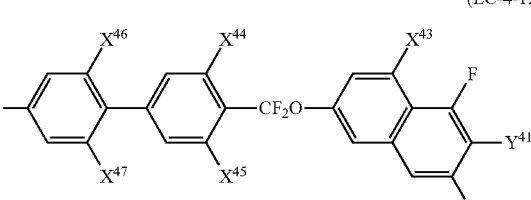
(LC-4-13)
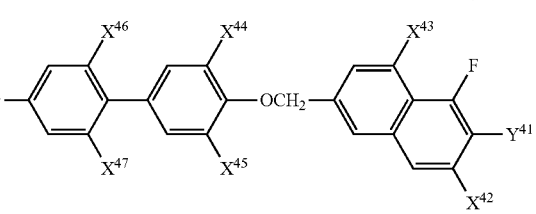
(LC-4-14)
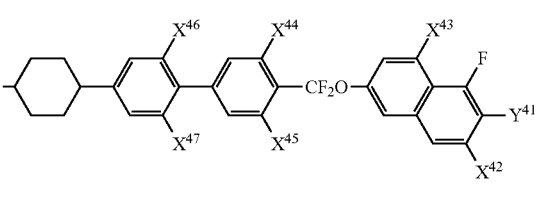
(LC-4-15)
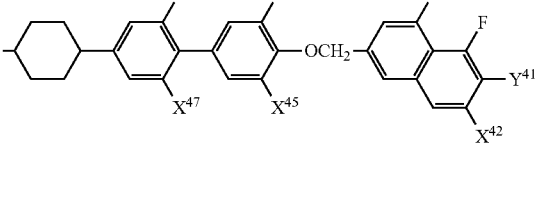
(LC-4-16)
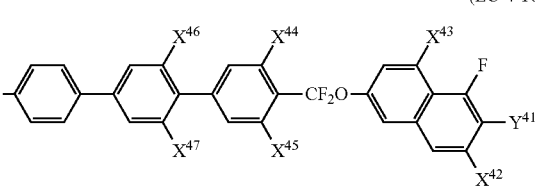

(LC-4-17)
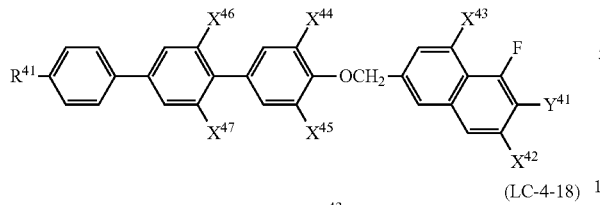
(LC-4-18)
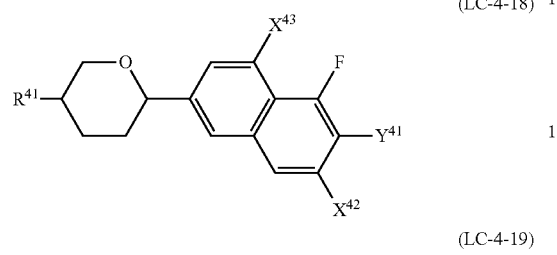
(LC-4-19)
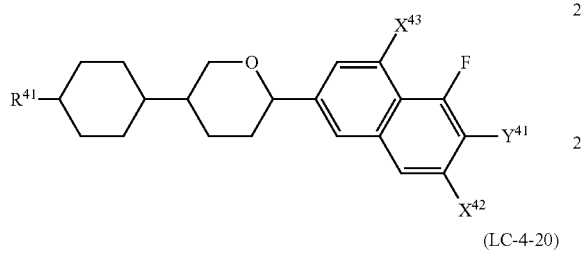
(LC-4-20)
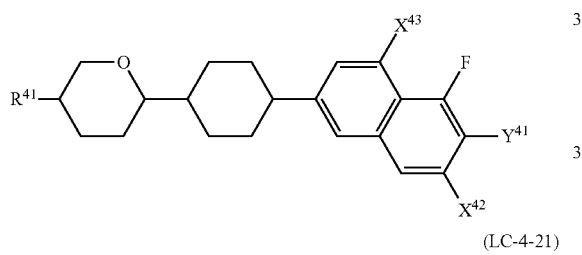
(LC-4-21)
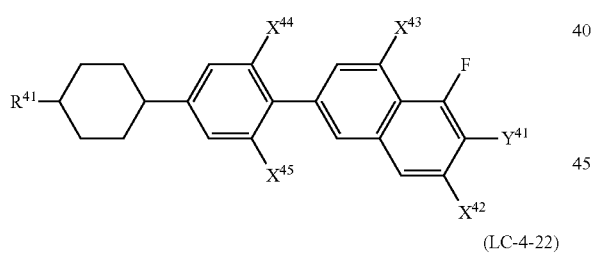
(LC-4-22)
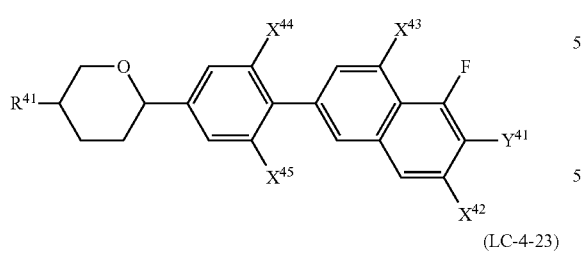
(LC-4-23)
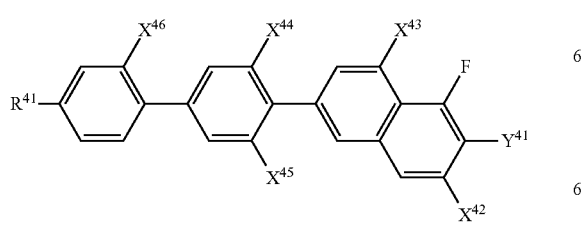
(LC-4-24)
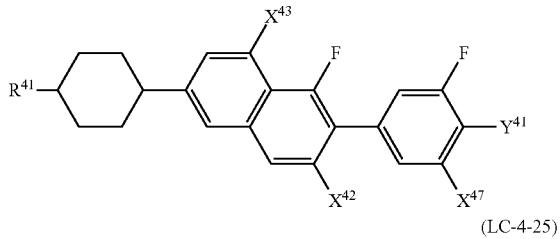
(LC-4-25)
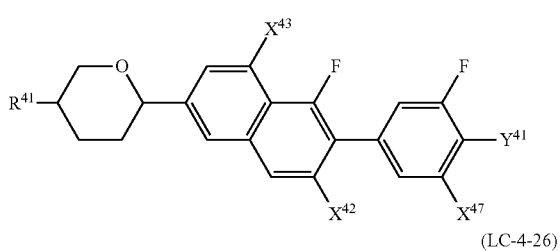
(LC-4-26)
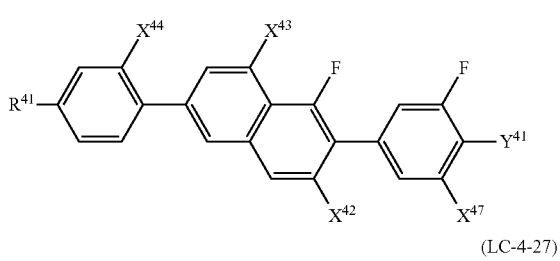
(LC-4-27)
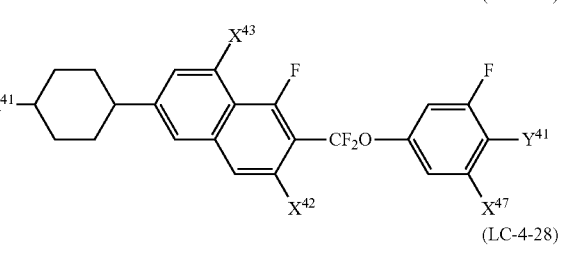
(LC-4-28)
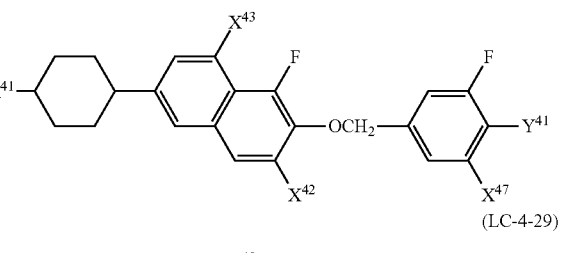
(LC-4-29)
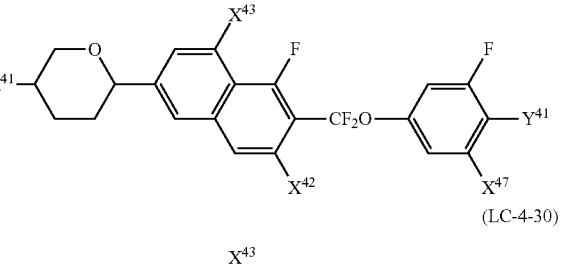
(LC-4-30)
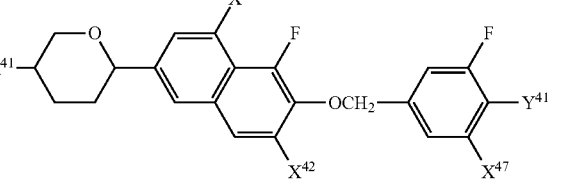

-continued (LC-4-31)
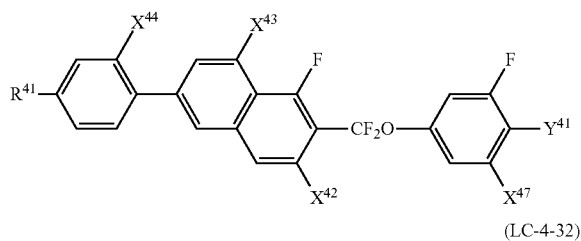

(LC-4-32)
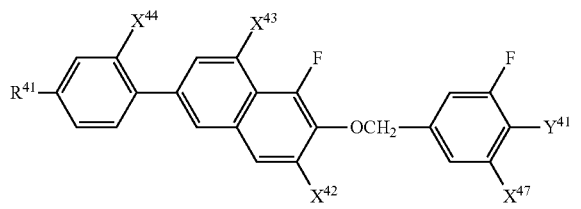

wherein $X^{44}$, $X^{45}$, $X^{46}$, and $X^{47}$ are each independently H, Cl, F, $CF_3$, or $OCF_3$; and $X^{42}$, $X^{43}$, $R^{41}$, and $Y^{41}$ are as defined in claim 6.

10. The liquid crystal composition according to claim 6, wherein the compound represented by general formula (LC5) is a compound represented by any of general formulas (LC5-1) to (LC5-26):

(LC5-1)
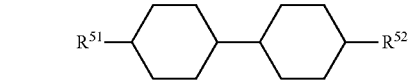

(LC5-2)
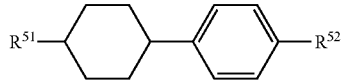

(LC5-3)
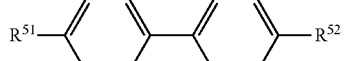

(LC5-4)
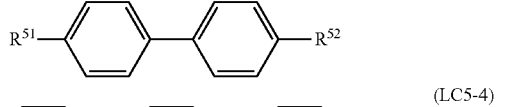

(LC5-5)

(LC5-6)

(LC5-7)
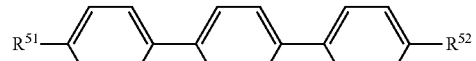

(LC5-8)
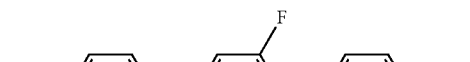

-continued (LC5-9)
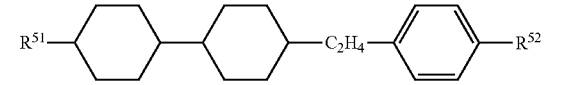

(LC5-10)
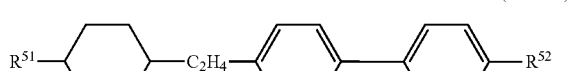

(LC5-11)
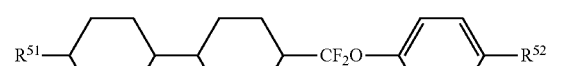

(LC5-12)
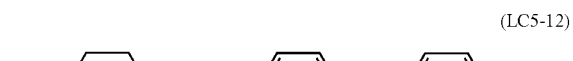

(LC5-13)
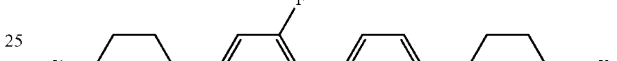

(LC5-14)
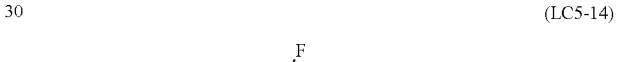

(LC5-15)
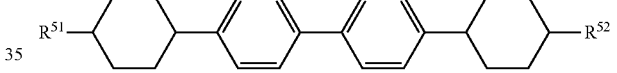

(LC5-16)
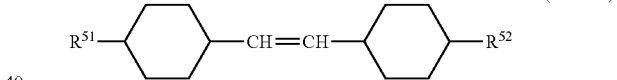

(LC5-17)
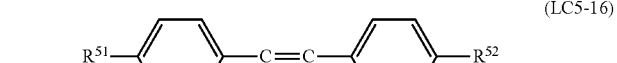

(LC5-18)

(LC5-19)
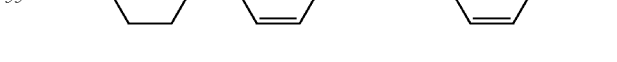

107
-continued
(LC5-20)
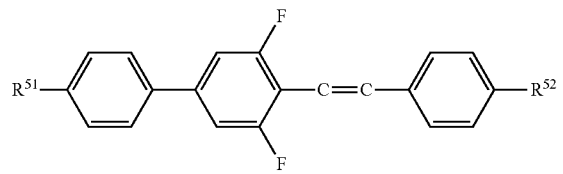
(LC5-21)
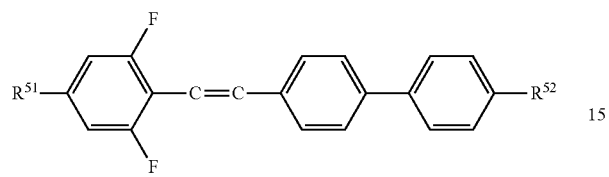
(LC5-22)
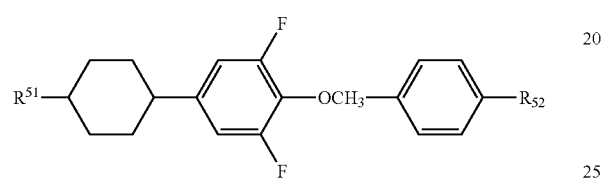
(LC5-23)
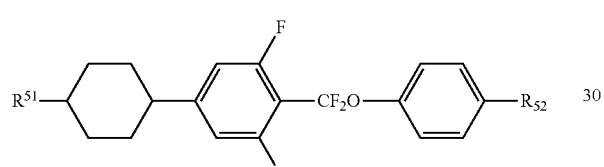
(LC5-24)
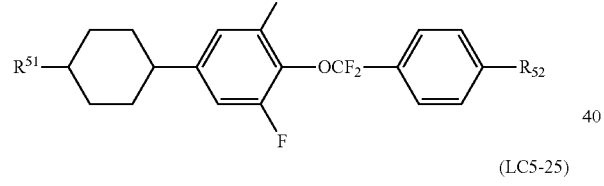
(LC5-25)
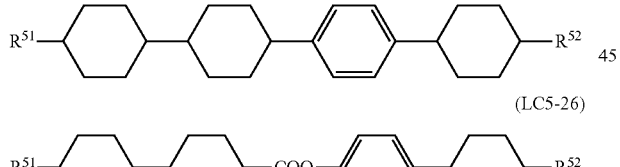
(LC5-26)
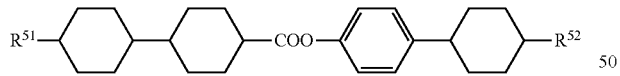
wherein $R^{51}$ and $R^{52}$ are as defined in claim 6.
11. The liquid crystal composition according to claim 6, wherein the compound represented by general formula (LC5) is any of the following compounds and is present in a total amount of at most 80% by mass:
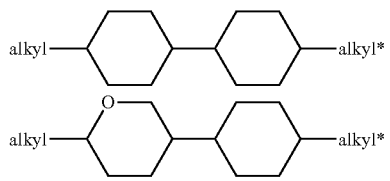
108
-continued
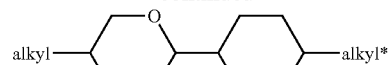
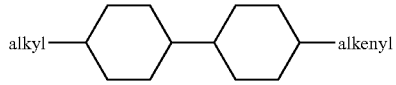
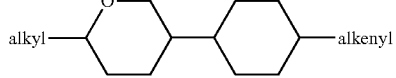
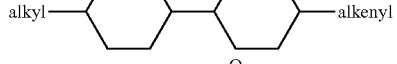
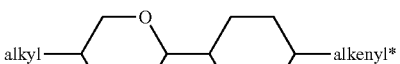
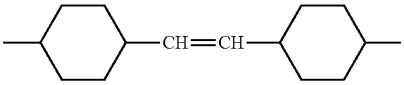
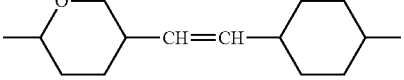
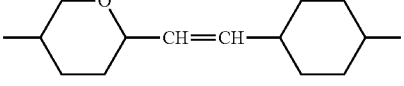
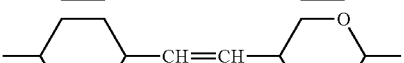
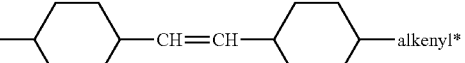
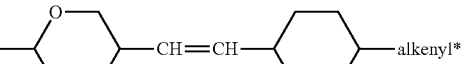
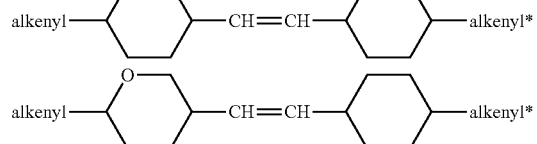

-continued

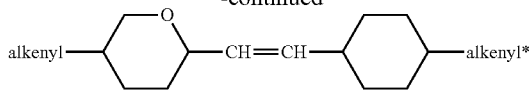

wherein alkyl and alkyl* are each independently an alkyl or alkoxy group of 1 to 5 carbon atoms; and alkenyl and alkenyl* are each independently an alkenyl or alkenyloxy group of 2 to 5 carbon atoms having the following formula.

12. The liquid crystal composition according to claim 6, wherein the liquid crystal composition comprises at least one compound selected from the group consisting of compounds represented by general formulas (LC1) to (LC4) wherein $R^{11}$ to $R^{41}$ are an alkenyl group of 2 to 5 carbon atoms.

13. The liquid crystal composition according to claim 6, wherein the liquid crystal composition comprises at least one compound selected from the group consisting of compounds represented by general formula (LC1) wherein $A^{11}$ is tetrahydropyran-2,5-diyl, compounds represented by general formula (LC2) wherein at least one of $A^{21}$ to $A^{23}$ present is tetrahydropyran-2,5-diyl, compounds represented by general formula (LC3) wherein at least one of $A^{31}$ and $A^{32}$ present is tetrahydropyran-2,5-diyl, compounds represented by general formula (LC4) wherein at least one of $A^{41}$ and $A^{42}$ present is tetrahydropyran-2,5-diyl, and compounds represented by general formula (LC5) wherein at least one of $A^{51}$ to $A^{53}$ present is tetrahydropyran-2,5-diyl.

14. The liquid crystal composition according to claim 6, wherein the liquid crystal composition comprises at least one compound selected from the group consisting of compounds represented by general formula (LC3) wherein at least one of $Z^{31}$ and $Z^{32}$ present is —CF$_2$O— or —OCH$_2$—, compounds represented by general formula (LC4) wherein at least one of $Z^{41}$ and $Z^{42}$ present is —CF$_2$O— or —OCH$_2$—, and compounds represented by general formula (LC5) wherein at least one of $Z^{51}$ and $Z^{52}$ present is —CF$_2$O— or —OCH$_2$—.

15. The liquid crystal composition according to claim 6, wherein the compound represented by general formula (LC5) is present in an amount of 30% to 70% by mass, and the liquid crystal composition has a viscosity η of 20 mPa·s or less at 20° C.

16. The liquid crystal composition according to claim 6, wherein the compound represented by general formula (LC2) is a compound represented by any of general formulas (LC2-1) to (LC2-14):

(LC2-1)
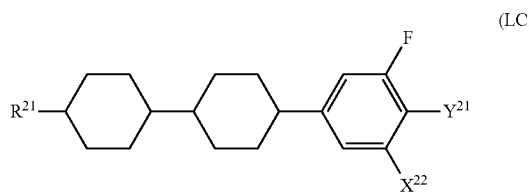

(LC2-2)
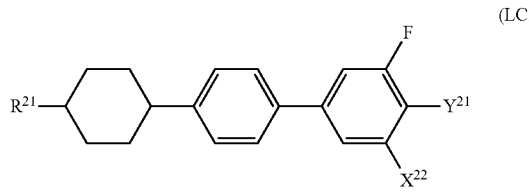

(LC2-3)
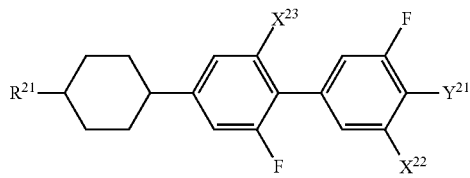

(LC2-4)
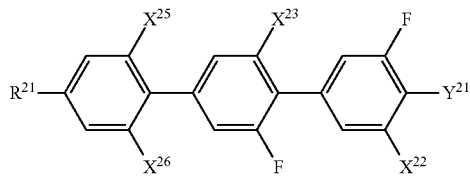

(LC2-5)
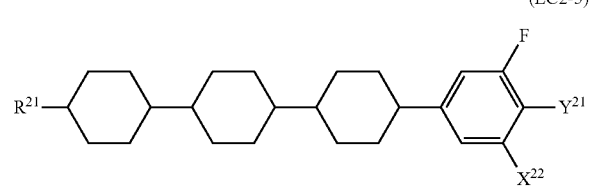

(LC2-6)
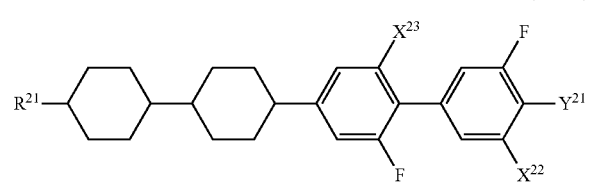

(LC2-7)
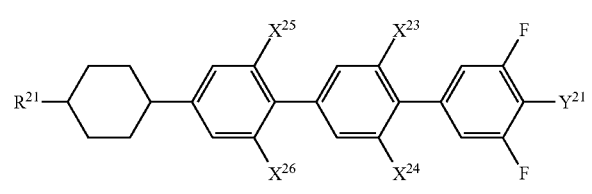

(LC2-8)
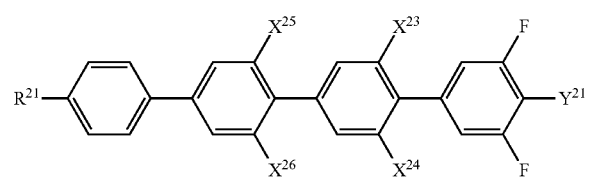

(LC2-9)
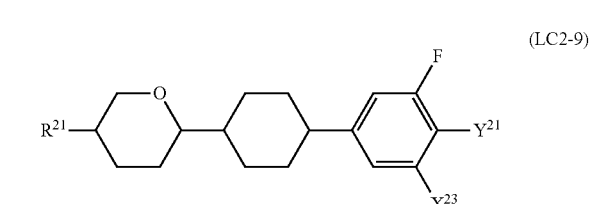

(LC2-10)
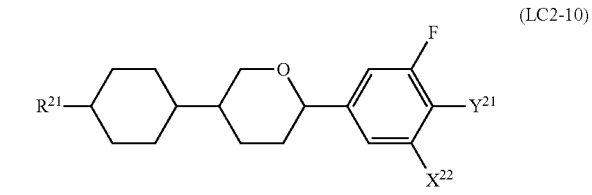

-continued

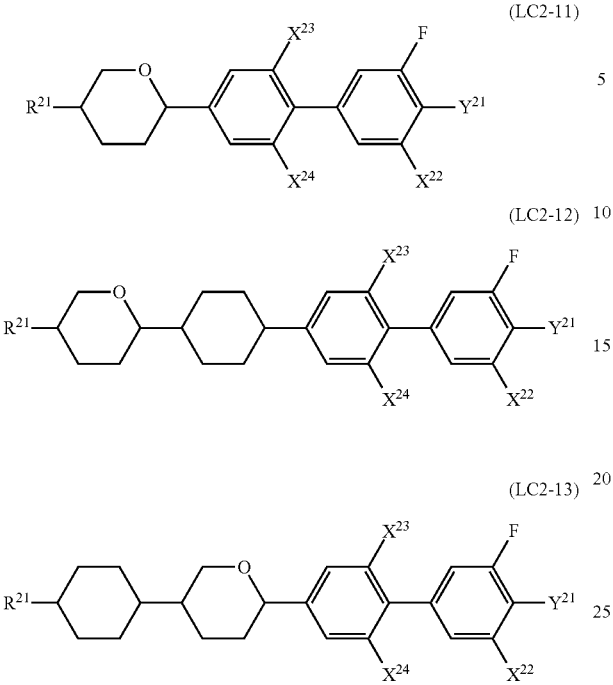

(LC2-11)
(LC2-12)
(LC2-13)
(LC2-14)

wherein $X^{23}$, $X^{24}$, $X^{25}$, and $X^{26}$ are each independently hydrogen, Cl, F, $CF_3$, or $OCF_3$; and $X^{22}$, $R^{21}$, and $Y^{21}$ are as defined in claim 6.

17. The liquid crystal composition according to claim 6, wherein the compound represented by general formula (LC3) is a compound selected from the group consisting of compounds represented by general formulas (LC3-1) to (LC3-32) and/or the group consisting of compounds represented by general formulas (LC3-O-1) to (LC3-O-97):

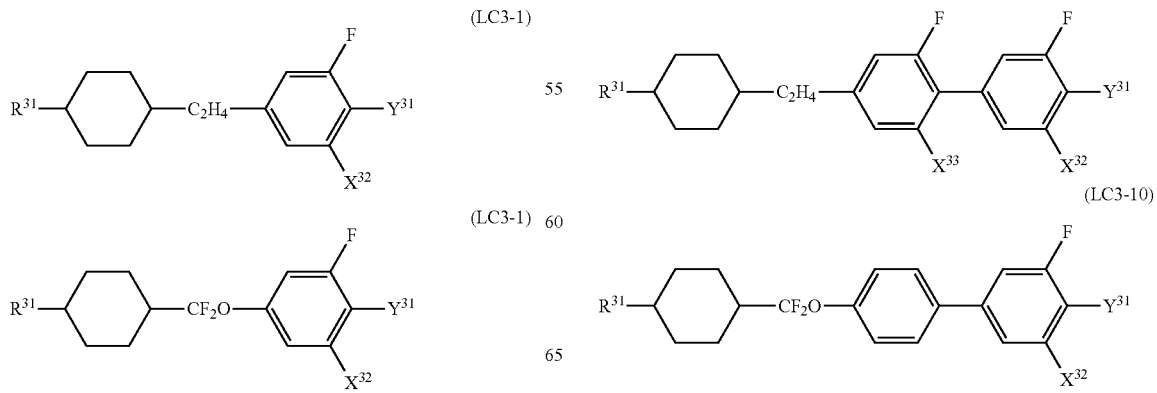

(LC3-1)
(LC3-1)

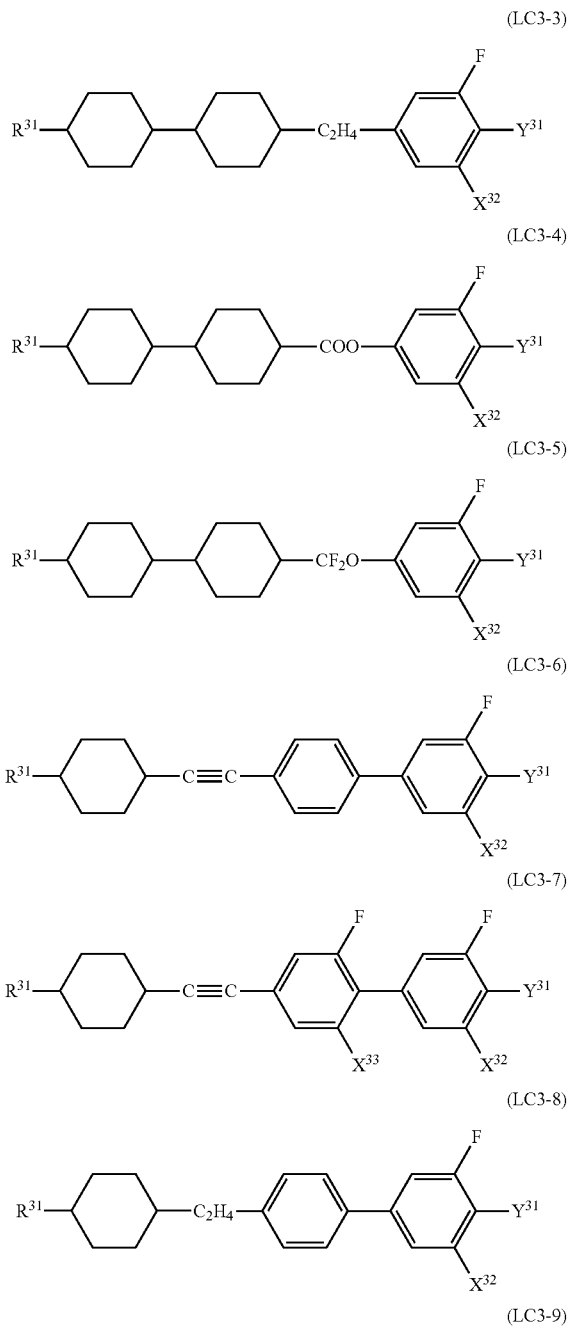

(LC3-3)
(LC3-4)
(LC3-5)
(LC3-6)
(LC3-7)
(LC3-8)
(LC3-9)
(LC3-10)

(LC3-11)
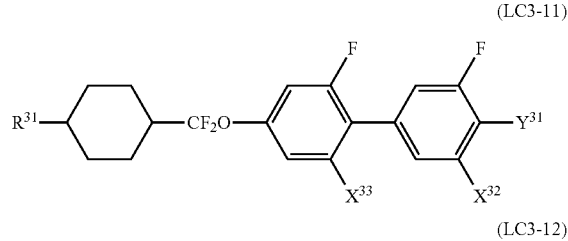
(LC3-12)
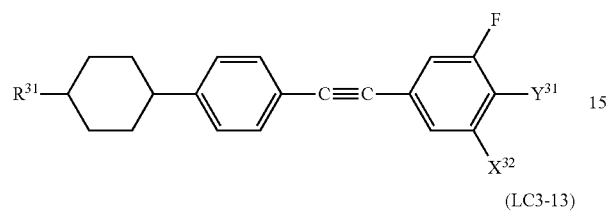
(LC3-13)
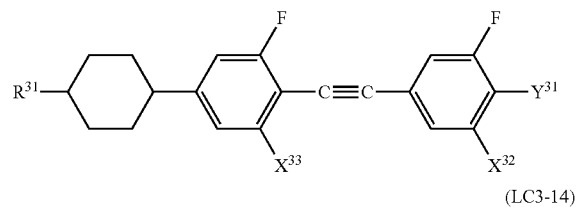
(LC3-14)
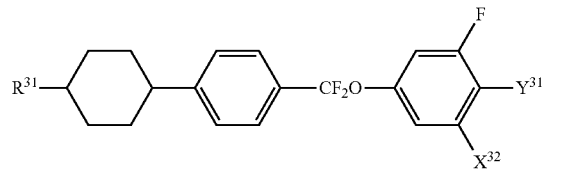
(LC3-15)
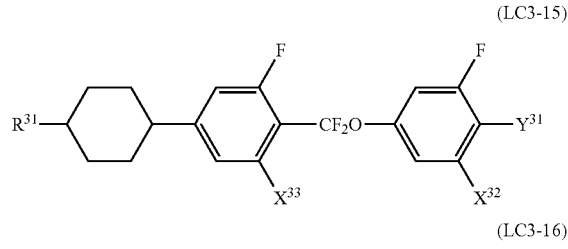
(LC3-16)
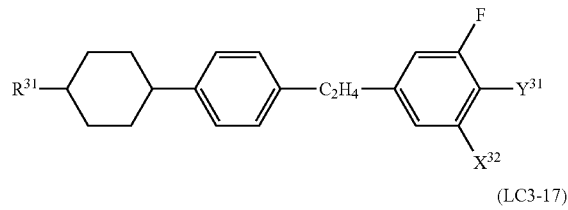
(LC3-17)
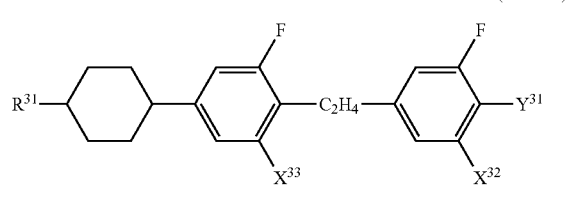
(LC3-18)
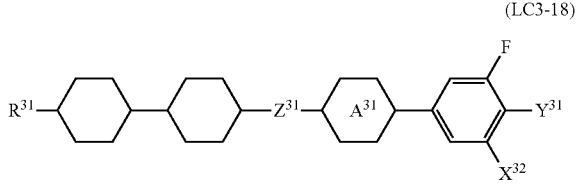
(LC3-19)
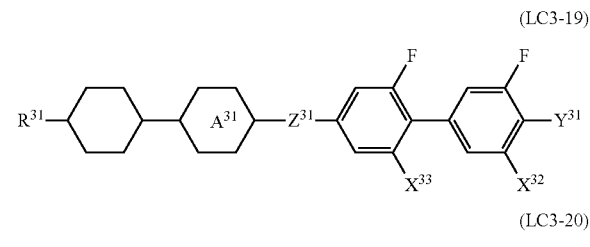
(LC3-20)
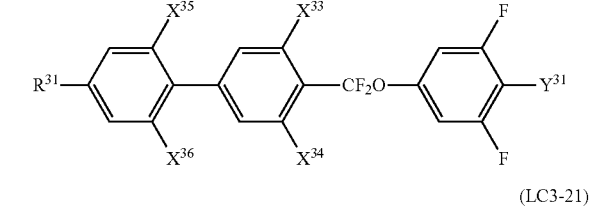
(LC3-21)
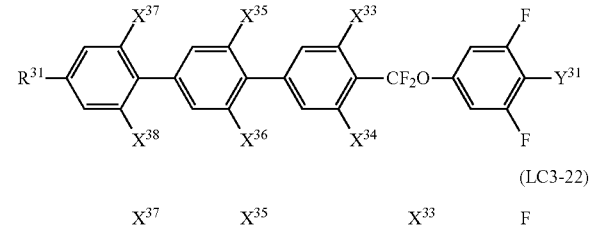
(LC3-22)
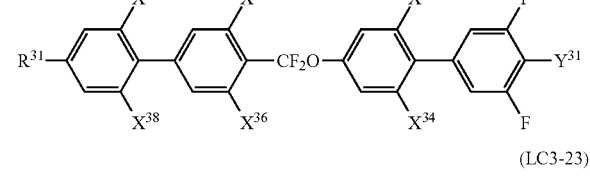
(LC3-23)
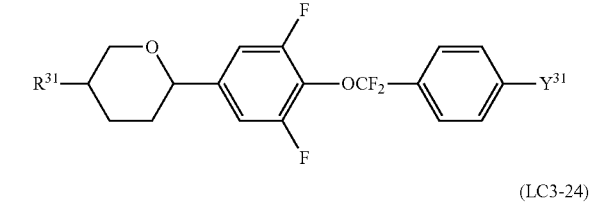
(LC3-24)
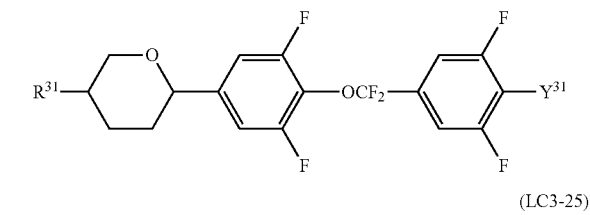
(LC3-25)
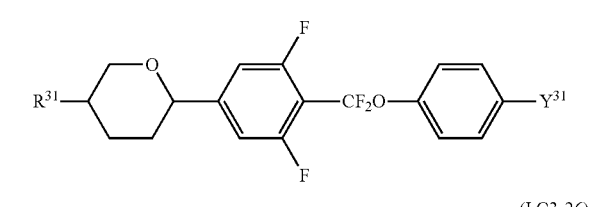
(LC3-26)
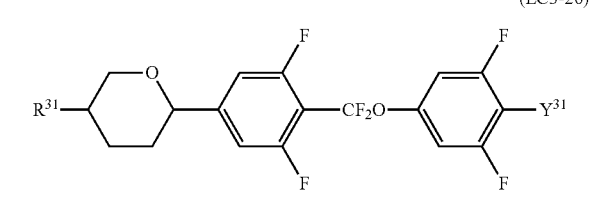

-continued (LC3-27)

(LC3-28)

(LC3-29)

(LC3-30)

(LC3-31)

(LC3-32)

(LC3-0-1)

(LC3-0-2)

(LC3-0-3)

-continued (LC3-0-4)

(LC3-0-5)

(LC3-0-6)

(LC3-0-7)

(LC3-0-8)

(LC3-0-9)

(LC3-0-10)

(LC3-0-11)

-continued
(LC3-0-12)
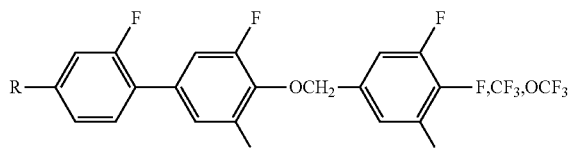
(LC3-0-13)
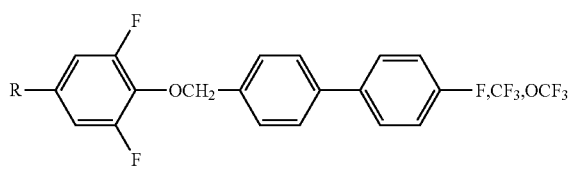
(LC3-0-14)
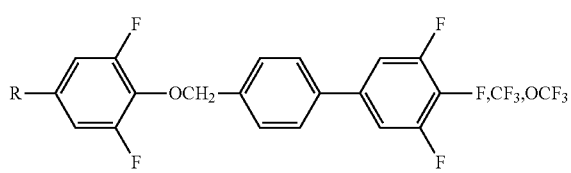
(LC3-0-15)
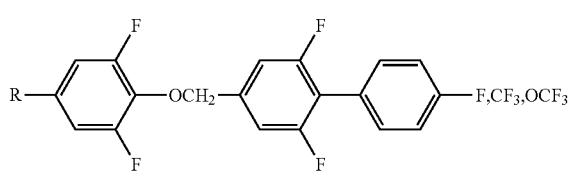
(LC3-0-16)
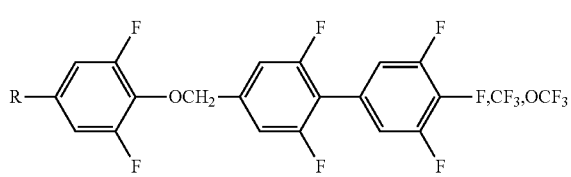
(LC3-0-17)
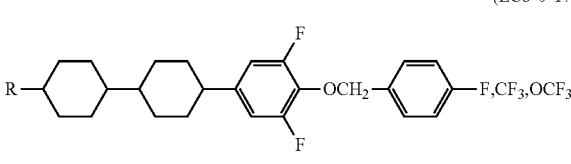
(LC3-0-18)
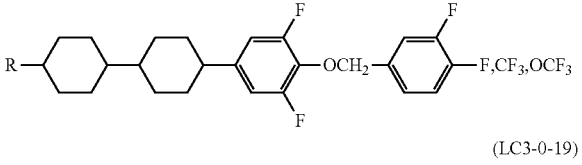
(LC3-0-19)
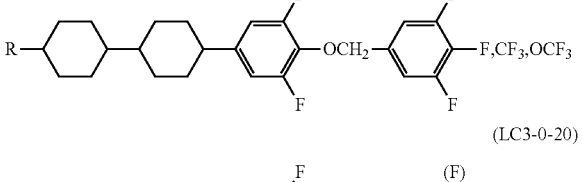
(LC3-0-20)
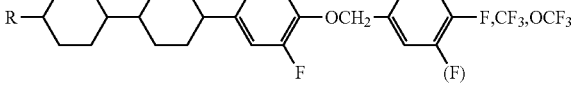
-continued
(LC3-0-21)
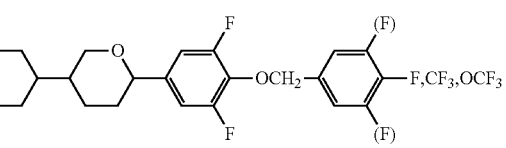
(LC3-0-22)
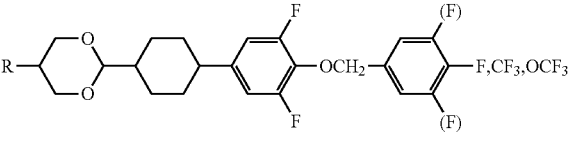
(LC3-0-23)
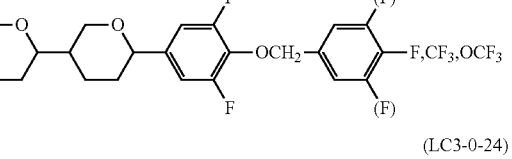
(LC3-0-24)
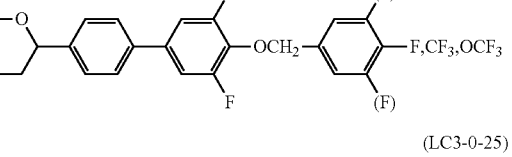
(LC3-0-25)
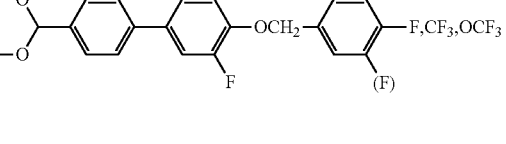
(LC3-0-26)
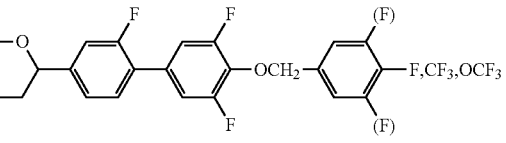
(LC3-0-27)
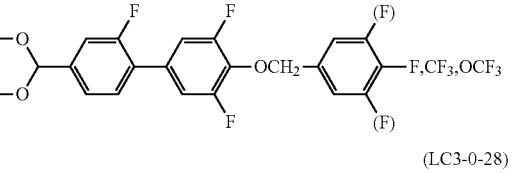
(LC3-0-28)
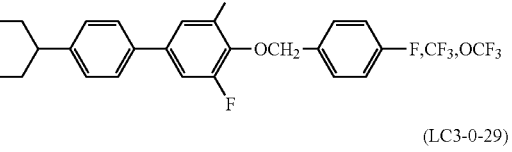
(LC3-0-29)
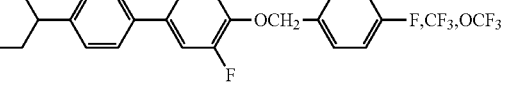

(LC3-0-30)
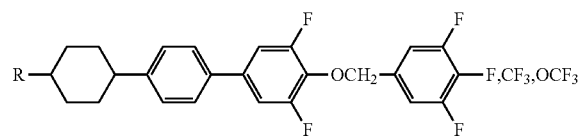
(LC3-0-31)
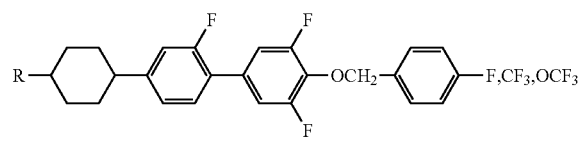
(LC3-0-32)
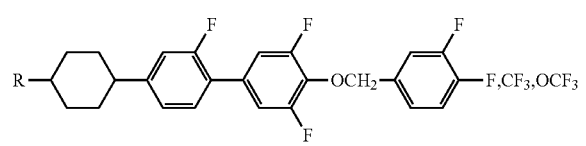
(LC3-0-33)
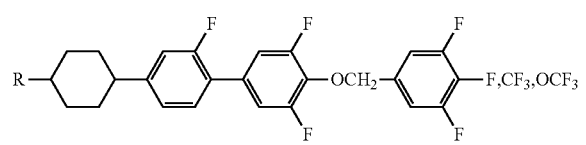
(LC3-0-34)
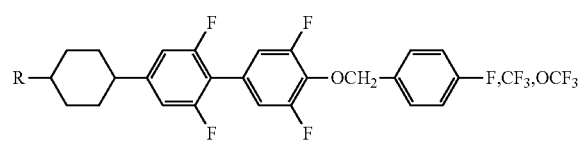
(LC3-0-35)
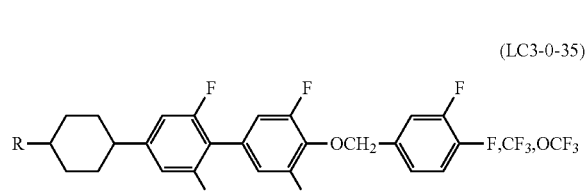
(LC3-0-36)
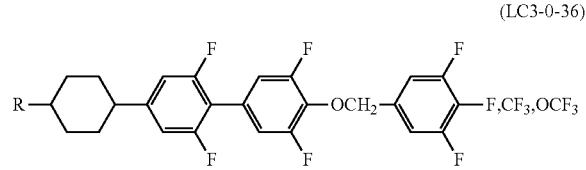
(LC3-0-37)
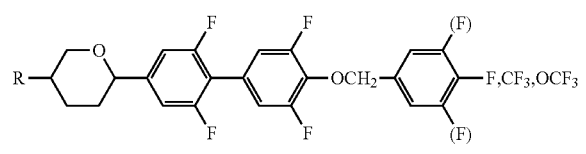
(LC3-0-38)
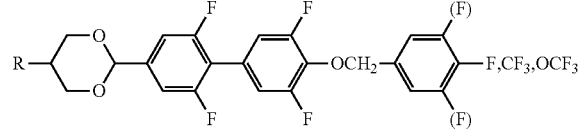
(LC3-0-39)
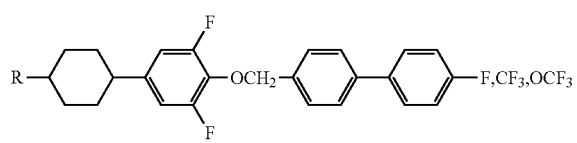
(LC3-0-40)
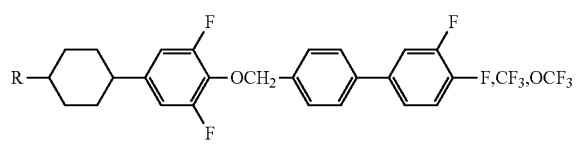
(LC3-0-41)
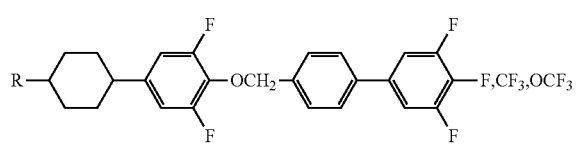
(LC3-0-42)
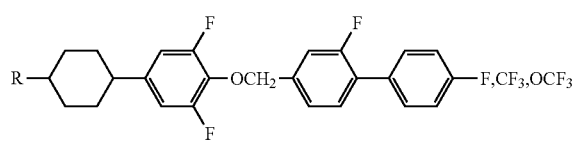
(LC3-0-43)
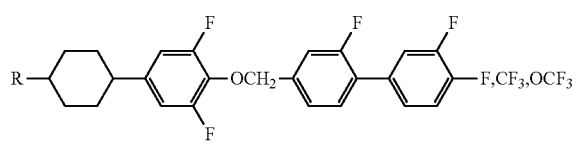
(LC3-0-44)
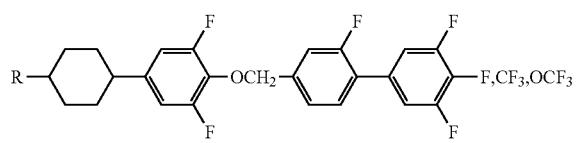
(LC3-0-45)
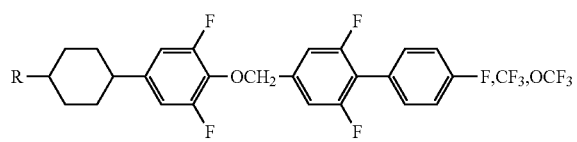
(LC3-0-46)
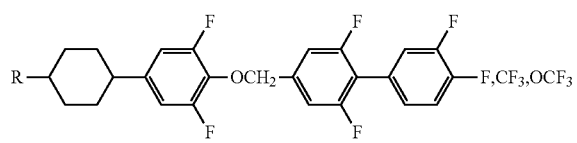
(LC3-0-47)
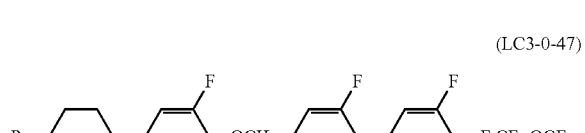

(LC3-0-48)
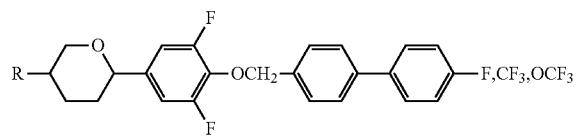
(LC3-0-49)
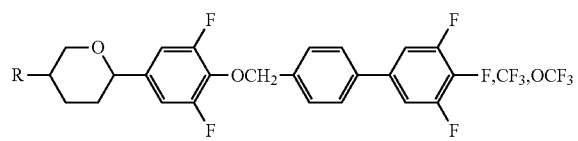
(LC3-0-50)
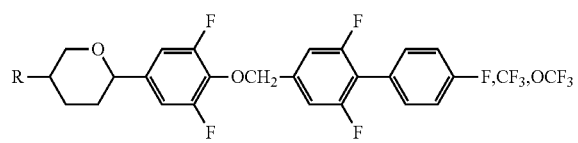
(LC3-0-51)
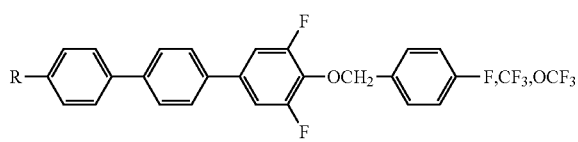
(LC3-0-52)
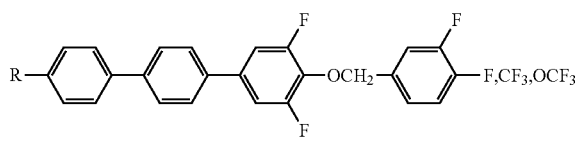
(LC3-0-53)
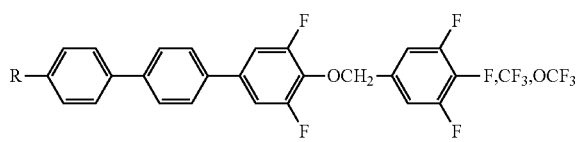
(LC3-0-54)
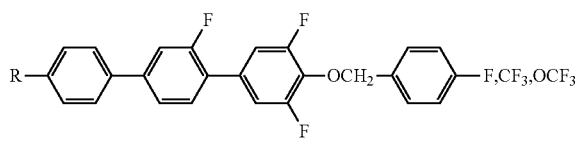
(LC3-0-55)
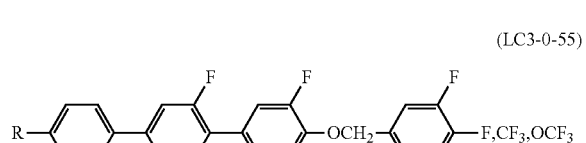
(LC3-0-56)
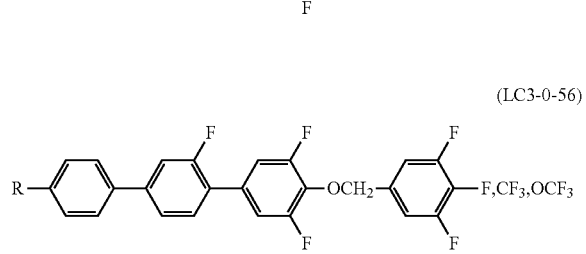
(LC3-0-57)
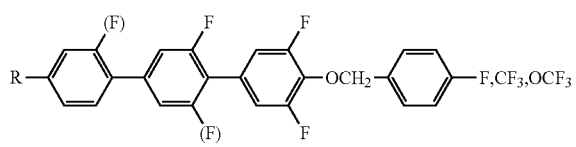
(LC3-0-58)
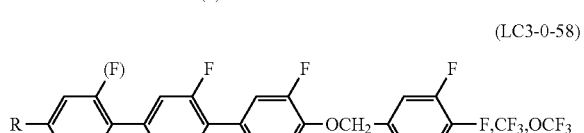
(LC3-0-59)
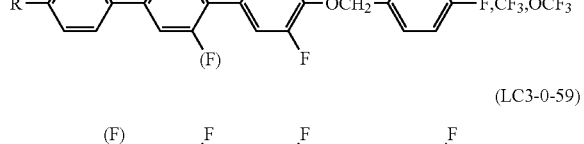
(LC3-0-60)
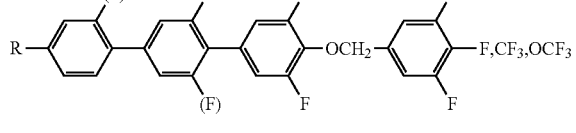
(LC3-0-61)
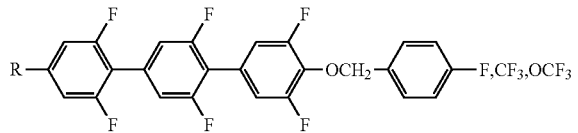
(LC3-0-62)
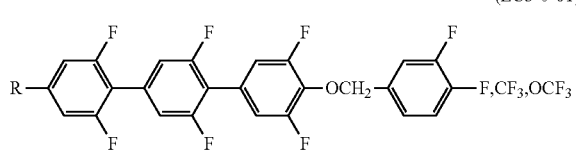
(LC3-0-63)
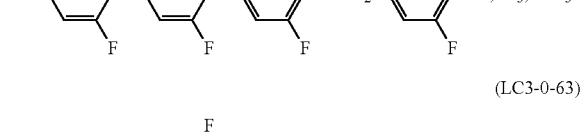
(LC3-0-64)
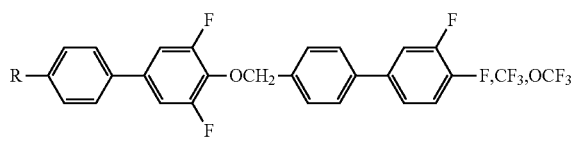
(LC3-0-65)
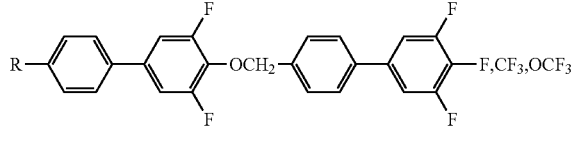

(LC3-0-66)
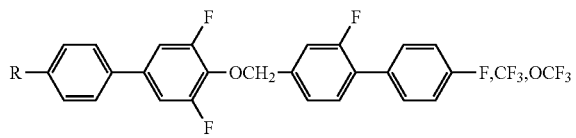
(LC3-0-67)
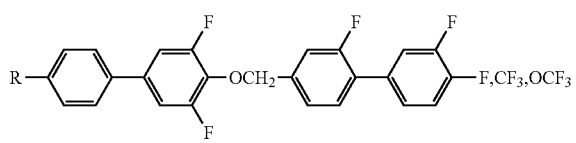
(LC3-0-68)
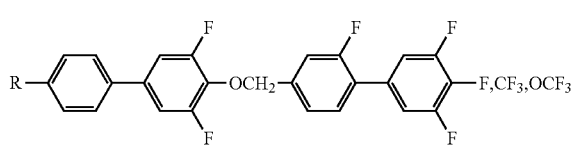
(LC3-0-69)
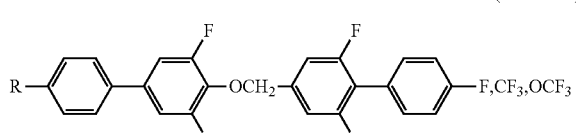
(LC3-0-70)
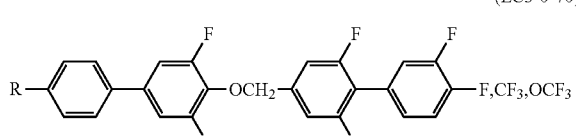
(LC3-0-71)
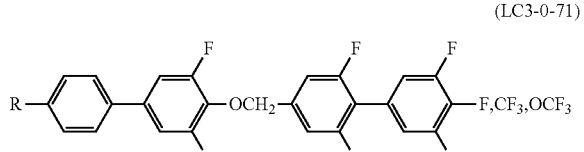
(LC3-0-72)
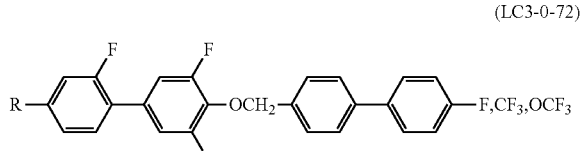
(LC3-0-73)
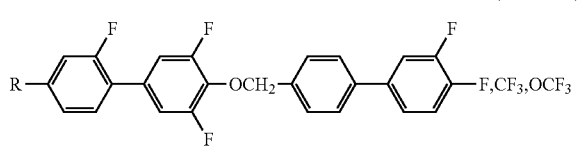
(LC3-0-74)
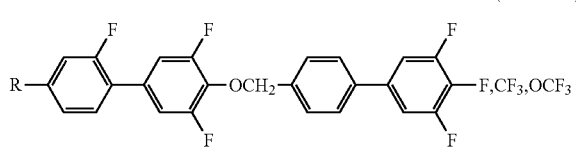
(LC3-0-75)
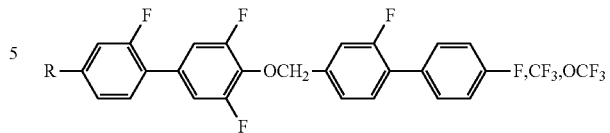
(LC3-0-76)
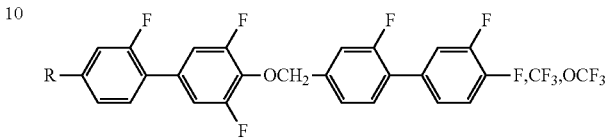
(LC3-0-77)
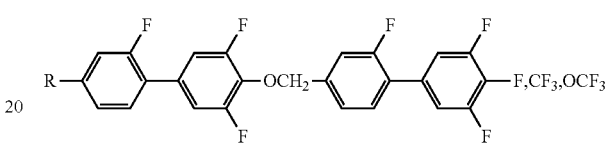
(LC3-0-78)
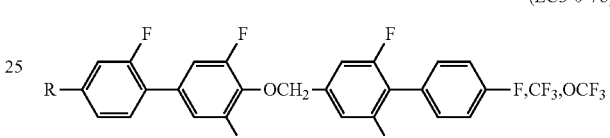
(LC3-0-79)
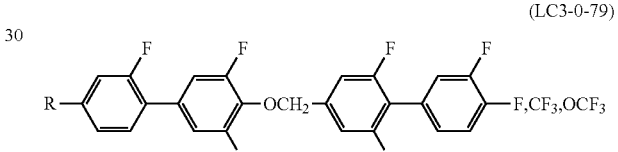
(LC3-0-80)
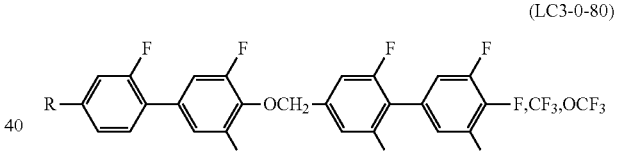
(LC3-0-81)
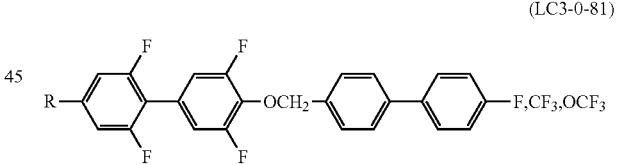
(LC3-0-82)
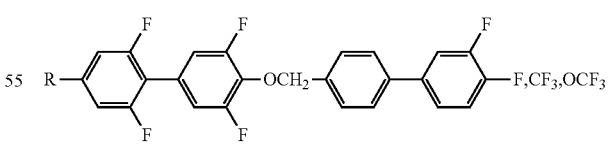
(LC3-0-83)
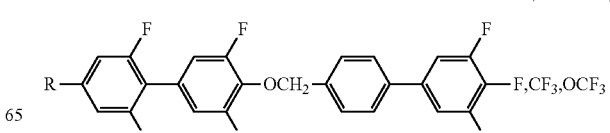

-continued (LC3-0-84)
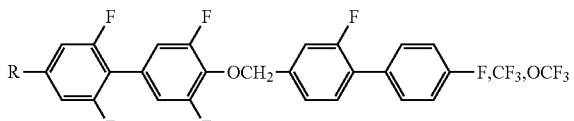

(LC3-0-85)
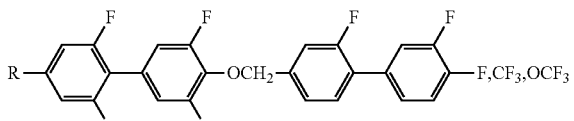

(LC3-0-86)
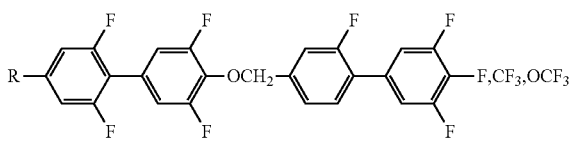

(LC3-0-87)
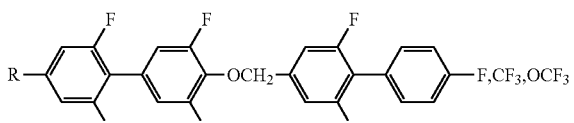

(LC3-0-88)
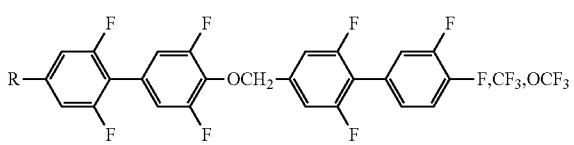

(LC3-0-89)
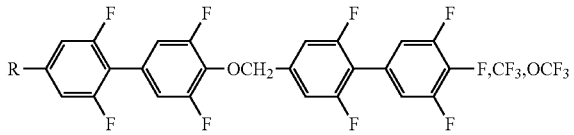

wherein R is as defined for $R^{31}$ in general formula (LC3); $X^{33}$, $X^{34}$, $X^{35}$, $X^{36}$, $X^{37}$, and $X^{38}$ are each independently H, Cl, F, $CF_3$, or $OCF_3$; $X^{32}$, $R^{31}$, $A^{31}$, $Y^{31}$, and $Z^{31}$ are as defined in claim 6; and F, $CF_3$, $OCF_3$, is —F, —$CF_3$, or —$OCF_3$.

18. The liquid crystal composition according to claim 1, further comprising at least one optically active compound.

19. The liquid crystal composition according to claim 1, further comprising at least one polymerizable compound.

20. The liquid crystal composition according to claim 1, further comprising at least one antioxidant.

21. The liquid crystal composition according to claim 1, further comprising at least one UV absorber.

22. A liquid crystal display device comprising the liquid crystal composition according to claim 1.

23. The liquid crystal display device according to claim 22, further comprising an alignment layer aligning liquid crystal molecules on a surface in contact with the liquid crystal molecules in a parallel, tilted, or perpendicular direction, the alignment layer being an alignment film comprising at least one compound selected from the group consisting of polyimides (PI), polyamides, chalcones, cinnamates, and cinnamoyl compounds.

24. The liquid crystal display device according to claim 23, wherein the alignment layer further comprises a polymerizable liquid crystal compound and/or a polymerizable non-liquid-crystal compound.

25. The liquid crystal display device according to claim 24, wherein the alignment layer in contact with the liquid crystal composition is an alignment film formed by photoalignment.

26. The liquid crystal display device according to claim 24, wherein the alignment layer in contact with the liquid crystal composition is an alignment film formed by photoalignment.

27. An active-matrix liquid crystal display device comprising the liquid crystal composition according to claim 1.

28. A TN, OCB, ECB, IPS, or VA-IPS liquid crystal display device comprising the liquid crystal composition according to claim 1.

29. A polymer-stabilized TN, OCB, ECB, IPS, or VA-IPS liquid crystal display device comprising the liquid crystal composition according to claim 19, wherein the polymerizable compound present in the liquid crystal composition is polymerized with or without application of voltage.

* * * * *